United States Patent
Lee

(10) Patent No.: US 8,597,958 B2
(45) Date of Patent: *Dec. 3, 2013

(54) IL1RL-1 AS A CARDIOVASCULAR DISEASE MARKER AND THERAPEUTIC TARGET

(75) Inventor: Richard T. Lee, Weston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 19 days.

This patent is subject to a terminal disclaimer.

(21) Appl. No.: 13/150,749

(22) Filed: Jun. 1, 2011

(65) Prior Publication Data

US 2011/0250703 A1    Oct. 13, 2011

Related U.S. Application Data

(63) Continuation of application No. 12/614,970, filed on Nov. 9, 2009, now Pat. No. 7,989,210, which is a continuation of application No. 10/435,482, filed on May 9, 2003, now Pat. No. 7,670,769.

(60) Provisional application No. 60/379,173, filed on May 9, 2002.

(51) Int. Cl.
*G01N 33/53* (2006.01)
*C12Q 1/68* (2006.01)
*A61K 45/00* (2006.01)

(52) U.S. Cl.
USPC .............. 436/501; 436/86; 435/7.1; 424/85.2

(58) Field of Classification Search
None
See application file for complete search history.

(56) References Cited

U.S. PATENT DOCUMENTS

| | | | |
|---|---|---|---|
| 5,217,899 | A | 6/1993 | Shapiro et al. |
| 5,348,879 | A | 9/1994 | Shapiro et al. |
| 5,786,163 | A | 7/1998 | Hall |
| 6,040,147 | A | 3/2000 | Ridker et al. |
| 6,288,218 | B1 | 9/2001 | Levinson |
| 6,323,334 | B1 | 11/2001 | Kingsbury et al. |
| 7,087,396 | B2 | 8/2006 | Tominaga et al. |
| 7,432,060 | B2 | 10/2008 | Lee |
| 7,655,415 | B2 | 2/2010 | Lee |
| 7,670,769 | B2 | 3/2010 | Lee |
| 7,985,558 | B2 | 7/2011 | Lee |
| 7,989,210 | B2 | 8/2011 | Lee |
| 7,998,683 | B2 | 8/2011 | Snider et al. |
| 8,090,562 | B2 | 1/2012 | Snider et al. |
| 2002/0072674 | A1 | 6/2002 | Criton et al. |

(Continued)

FOREIGN PATENT DOCUMENTS

| | | |
|---|---|---|
| WO | 98/07754 | 2/1998 |
| WO | 98/38311 | 9/1998 |

(Continued)

OTHER PUBLICATIONS

Oshikawa et al., (Am J Respir Crit Care Med. Apr. 1, 2002; 165(7): 1005-9).*

(Continued)

*Primary Examiner* — Cherie M Stanfield
(74) *Attorney, Agent, or Firm* — Fish & Richardson P.C.

(57) ABSTRACT

This invention pertains to methods and compositions for the diagnosis and treatment of cardiovascular conditions. More specifically, the invention relates to isolated molecules that can be used to diagnose and/or treat cardiovascular conditions including cardiac hypertrophy, myocardial infarction, stroke, arteriosclerosis, and heart failure.

33 Claims, 10 Drawing Sheets

(56) References Cited

U.S. PATENT DOCUMENTS

| | | | |
|---|---|---|---|
| 2003/0124624 | A1 | 7/2003 | Tominaga et al. |
| 2004/0048286 | A1 | 3/2004 | Lee |
| 2005/0130136 | A1 | 6/2005 | Lee |
| 2005/0203046 | A1 | 9/2005 | Schmitz et al. |
| 2006/0216755 | A1 | 9/2006 | Lee |
| 2007/0042978 | A1 | 2/2007 | Girard et al. |
| 2008/0003199 | A1 | 1/2008 | Lee |
| 2009/0192078 | A1 | 7/2009 | Lee |
| 2009/0305265 | A1 | 12/2009 | Snider et al. |
| 2010/0009356 | A1 | 1/2010 | Snider et al. |
| 2010/0055683 | A1 | 3/2010 | Snider et al. |
| 2010/0159607 | A1 | 6/2010 | Lee |
| 2011/0053170 | A1 | 3/2011 | Snider et al. |
| 2011/0256635 | A1 | 10/2011 | Snider |
| 2011/0262941 | A1 | 10/2011 | Snider et al. |
| 2011/0280887 | A1 | 11/2011 | Lee |
| 2012/0040381 | A1 | 2/2012 | Snider et al. |
| 2012/0065897 | A1 | 3/2012 | Snider et al. |
| 2012/0276551 | A1 | 11/2012 | Snider |
| 2013/0071404 | A1 | 3/2013 | Snider et al. |

FOREIGN PATENT DOCUMENTS

| | | |
|---|---|---|
| WO | 99/34217 | 7/1999 |
| WO | 00/35951 | 6/2000 |
| WO | 00/35473 | 11/2000 |
| WO | 00/73498 | 12/2000 |
| WO | 01/70817 | 9/2001 |
| WO | 02/38794 | 5/2002 |
| WO | 03/094856 | 11/2003 |
| WO | 2004/056868 | 7/2004 |
| WO | 2007/127749 | 11/2007 |

OTHER PUBLICATIONS

U.S. Appl. No. 13/782,326, filed Mar. 1, 2013, Snider.
U.S. Appl. No. 13/787,137, filed Mar. 6, 2013, Snider et al.
U.S. Appl. No. 13/788,276, filed Mar. 7, 2013, Lee.
U.S. Appl. No. 13/788,922, filed Mar. 7, 2013, Lee.
U.S. Appl. No. 13/787,975, filed Mar. 7, 2013, Snider et al.
U.S. Appl. No. 13/789,941, filed Mar. 8, 2013, Lee.
U.S. Appl. No. 13/897,249, filed May 17, 2013, Snider et al.
Albert et al., Prospective study of C-reactive protein, homocysteine, and plasma lipid levels as predictors of sudden cardiac death. Circulation. Jun. 4, 2002;105(22):2595-9. Auer et al, "C-reactive protein and coronary artery disease," Jpn Heart J., 43(6):607-619 (2002).
Amendment filed in Response on Jan. 18, 2007 for U.S. Appl. No. 10/435,482.
Amendment filed in Response on Dec. 23, 2005 for U.S. Appl. No. 10/024,607.
Amendment filed in Response on May 30, 2006 for U.S. Appl. No. 10/024,607.
Anwaruddin et al., "Renal function, congestive heart failure, and amino-terminal pro-brain natriuretic peptide measurement: results from the ProBNP Investigation of Dyspnea in the Emergency Department (PRIDE) Study," J. Am. Coll. Cardiol., 47(1):91-97 (2006).
Auer et al, "C-reactive protein and coronary artery disease," Jpn Heart J., 43(6):607-619 (2002).
Aukrust et al., "Cytokine network in congestive heart failure secondary to ischemic or idiopathic dilated cardiomyopathy," Am J Cardiol., 83(3):376-382 (1999).
Baggish et al., "A validated clinical and biochemical score for the diagnosis of acute heart failure: The ProBNP Investigation of Dyspnea in the Emergency Department (PRIDE) Acute Heart Failure Score," Am. Heart J. 151:48-54 (2006).
Baumgarten et al., "Cytokines as emerging targets in the treatment of heart failure," Trends Cardiovasc Med., 10(5):216-223 (2000).
Belch et al., "Oxygen free radicals and congestive heart failure," Br Heart J., 65(5):245-248 (1991).
Blum et al., "Pathophysiological role of cytokines in congestive heart failure," Annu. Rev. Med., 52:15-27 (2001) (abstract).
Boisot et al., "Serial Sampling of ST2 Predicts 90-Day Mortality Following Destabilized Heart Failure," Journal of Cardiac Failure, 14:732-738 (2008).
Brint et al., "ST2 is an inhibitor of interleukin 1 receptor and Toll-like receptor 4 signaling and maintains endotoxin tolerance," Nat. Immunol., 5(4):373-379 (2004).
Brown, "Techniques for Mechanical Stimulation of cells in vitro: a review," Journal of Biomechanics, 33:3-14 (2000).
Bruneau, "Selective changes in natriuretic peptide and early response gene expression in isolated rat atria following stimulation by stretch or endothelin-1," Cardiovasc. Res., 28(10):1519-1525 (1994).
Brunner et al., "Increased levels of soluble ST2 protein and IgG1 production in patients with sepsis and trauma," Intensive Care Med., 30(7):1468-1473 (2004).
Carter et al., "Regulation of ST2L expression of T helper (Th) type 2 cells," Eur. J. Immunol , 31(10):2979-2985 (2001). (Abstract Only).
Chan et al., "Human IL-18 receptor and ST2L are stable and selective markers for the respective type 1 and type 2 circulating lymphocytes," J Immunol., 167(3):1238-1244 (2001). (abstract).
Cheng et al., Mechanical strain tightly controls fibroblast growth factor-2 release from cultured human vascular smooth muscle cells. Circ Res. Jan. 1997;80(1):28-36. (Abstract).
Conklin, B "B-type Natriuretic Peptide: A New Measurement to Distinguish Cardiac From Pulmonary Causes of Acute Dyspenea," Journal of Emergency Nursing, 31(1):73-75 (2005) (20060-0006EP Search).
Coyle et al., "Crucial role of the interleukin 1 receptor family member T1/ST2 in T helper cell type 2-mediated lung mucosal immune responses," J Exp Med., 190(7):895-902 (1999).
Dale et al., Genomics, 57:177-179 (1999).
De Keulenaer et al., "Identification of IEX-1 as a biomechanically controlled nuclear factor-kappaB target gene that inhibits cardiomyocyte hypertrophy," Circ Res., 90(6):690-696 (2002).
EP 03728848.7 Dec. 15, 2005 Supplementary European Search Report.
Feldman et al., "C-reactive protein is an independent predictor of mortality in women with HIV-1 infection," J. Acquir. Immune Defic. Syndr., 32(2):210-214 (2003). (abstract).
Feng et al., "Transcriptional profile of mechanically induced genes in human vascular smooth muscle cells," Circ Res., 85(12):1118-23 (1999).
Figal et al., "Usefulness of NTproBNP in the emergency management of patients with severe syspnea and an uncertain heart failure diagnosis," Revista Española de Cardiología, 58(10):1155-1161 (2005). (20060-0006EP Search).
Forssmann et al., "The heart is the center of a new endocrine, paracrine, and neuroendocrine system," Arch. Histol. Cytol., 52 Suppl:293-315 (1989). (Abstract).
Frangogiannis et al., "Resident cardiac mast cells degranulate and release preformed TNF-alpha, initiating the cytokine cascade in experimental canine myocardial ischemia/reperfusion," Circulation., 98(7):699-710 (1998).
Galvani et al., "Prognostic influence of elevated values of cardiac troponin I in patients with unstable angina," Circulation, 95(8):2053-2059 (1997). (Abstract).
GenBank Acc. No. NM_003856 (PRI Nov. 18, 2007).
GenBank Acc. No. NM_016232 (PRI Nov. 18, 2007).
GenBank Acc. No. NP_003847 (PRI Nov. 18, 2007).
GenBank Acc. No. NP_057316 (PRI Nov. 18, 2007).
GenBank Submission; NIH/NCBI; Accession No. AB022176 (PRI Sep. 15, 2007).
GenBank Submission; NIH/NCBI; Accession No. AB024518 (PRI Mar. 10, 1999).
GenBank Submission; NIH/NCBI; Accession No. AL117622 (printed Sep. 25, 2007) (2 pages).
GenBank Submission; NIH/NCBI; Accession No. D12763 (PRI Jan. 23, 2003).
GenBank Submission; NIH/NCBI; Accession No. E07714 (PAT Nov. 4, 2005).
GenBank Submission; NIH/NCBI; Accession No. E07716 (PAT Nov. 4, 2005).
GenBank Submission; NIH/NCBI; Accession No. E08652 (PAT Nov. 4, 2005).

(56) References Cited

OTHER PUBLICATIONS

GenBank Submission; NIH/NCBI; Accession No. U04317 (printed Aug. 23, 2000) (2 pages).
GenBank Submission; NIH/NCBI; Accession No. U04319 (printed Aug. 23, 2000) (2 pages.).
GenBank Submission; NIH/NCBI; Accession No. X60184 (printed Sep. 25, 2007) (5 pages).
Goetze et al., "B-type natriuretic peptide and its precursor in cardiac venous blood from failing hearts," European Journal of Heart Failure, 7(1):69-74 (2005). (20060-0006EP Search).
Goldstein, Am J Cardiol, Dec. 1981; 48(6):1147-54. (Abstract Only).
Gutstein et al., Role of inositol 1,4,5-trisphosphate receptors in regulating apoptotic signaling and heart failure. Heart Vessels. 1997;Suppl 12:53-7.
Gwechenberger et al., Cardiac myocytes produce interleukin-6 in culture and in viable border zone of reperfused infarctions. Circulation. Feb. 2, 1999;99(4):546-51.
Hanyu T, et al. Urinary Thrombomodulin in Patients with Rheumatoid Arthritis: Relationship to Disease Subset. 1999; 18:385-9.
Heeschen et al., Predictive value of C-reactive protein and troponin T in patients with unstable angina: a comparative analysis. CAPTURE Investigators. Chimeric c7E3 AntiPlatelet Therapy in Unstable angina Refractory to standard treatment trial. J Am Coll Cardiol. May 2000;35(6):1535-42. Abstract Only.
Hirota et al., Loss of a gp130 cardiac muscle cell survival pathway is a critical event in the onset of heart failure during biomechanical stress. Cell. Apr. 16, 1999;97(2):189-98.
Interview Summary mailed Nov. 23, 2005 for U.S. Appl. No. 10/024,607.
IPER as issued in PCT/US01/46816 on Aug. 12, 2004.
ISR as issued in PCT/US01/46816 on May 9, 2003.
Iwahana et al., Different promoter usage and multiple transcription initiation sites of the interleukin-1 receptor-related human ST2 gene in UT-7 and TM12 cells. Eur J Biochem. Sep. 1999;264(2):397-406.
Izakov et al., Cooperative effects due to calcium binding by troponin and their consequences for contraction and relaxation of cardiac muscle under various conditions of mechanical loading. Circ Res. Nov. 1991;69(5):1171-84.
Januzzi et al., "Measurement of the Interleukin Family Member ST2 in Patients with Acute Dyspnea: Results from the PRIDE (Pro-Brain Natriuretic Peptide Investigation of Dyspnea in the Emergency Department) Study," J. Am. Coll. Cardiol., 50:607-613 (2007).
Januzzi et al., "NT-proBNP testing for diagnosis and short-term prognosis in acute destabilized heart failure: an international pooled analysis of 1256 patients: the International Collaborative of NT-proBNP Study," Eur. Heart J., 27(3):330-337 (2006).
Januzzi et al., "The N-terminal Pro-BNP investigation of dyspnea in the emergency department (PRIDE) study," Am. J. Cardiol., 95(8):948-954 (2005).
Januzzi et al., "The value of soluble ST2 measurement for the diagnostic and prognostic evaluation of patients with acute dyspnea," Circulation, 114(18):721 (2006) (abstract).
Januzzi et al., "Utility of amino-terminal pro-brain natriuretic Peptide testing for prediction of 1-year mortality in patients with dyspnea treated in the emergency department," Arch. Intern. Med., 166(3):315-320 (2006).
Joyce et al., Two inhibitors of pro-inflammatory cytokine release, interleukin-10 and interleukin-4, have contrasting effects on release of soluble p75 tumor necrosis factor receptor by cultured monocytes. Eur J Immunol. Nov. 1994;24(11):2699-705.
Kakkar et al., "The IL-33/ST2 pathway: Therapeutic target and novel biomarker," Nature Reviews Drug Discovery, 7(10):827-840 (2008) (20060-0004EP Search).
Kida et al., Pathophysiological role of natriuretic peptides. Rinsho Byori. Aug. 1989;37(8):875-82. Abstract Only.
Kumar et al., "ST2/T1 protein functionally binds to two secreted proteins from Balb/c 3T3 and human umbilical vein endothelial cells but does not bind interleukin 1," J. Biol. Chem., 270(46):27905-27913 (1995).
Kumar et al., Expression of ST2, an interleukin-1 receptor homologue, is induced by proinflammatory stimuli. Biochem Biophys Res Commun. Jun. 27, 1997;235(3):474-8.
Kuroiwa et al., "Construction of ELISA system to quantify human ST2 protein in sera of patients. Hybridoma," 19(2):151-159 (2000).
Kuroiwa K, et al., Identification of Human ST2 Protein in the Sera of Patients with Autoimmune Diseases. Biochemical and Biophysical Research Communications 2001; 284:1104-8.
Laine et al., Effect of ryanodine on atrial natriuretic peptide secretion by contracting and quiescent rat atrium. Pflugers Arch. Feb. 1994;426(3-4):276-83.
Lammerding et al., Mechanotransduction in cardiac myocytes. Ann N Y Acad Sci. May 2004;1015:53-70.
Lee et al., "Novel markers for heart failure diagnosis and prognosis," Curr Opin Cardiol, 20(3):201-210 (2005).
Leyva et al., European Heart J., 19:1814-1822 (1998).
Lohning et al., "T1/ST2 is preferentially expressed on murine Th2 cells, independent of interleukin 4, interleukin 5, and interleukin 10, and important for Th2 effector function," Proc. Natl. Acad. Sci. U.S.A., 95(12):6930-6935 (1998).
MacGowan et al., Circulating interleukin-6 in severe heart failure. Am J Cardiol. Apr. 15, 1997;79(8):1128-31.
MacKenna et al., Role of mechanical factors in modulating cardiac fibroblast function and extracellular matrix synthesis. Cardiovasc Res. May 2000;46(2):257-63.
Maisel et al., "Bedside B-Type Natriuretic Peptide in the Emergency Diagnosis of Heart Failure With Reduced or Preserved Ejection Fraction," J. Am. Coll. Cardiol., 41:2010-7i (2003).
Maisel et al., "Rapid measurement of B-type natriuretic peptide in the emergency diagnosis of heart failure," N. Engl. J. Med., 347(3):161-167 (2002).
Mann et al., Stress activated cytokines and the heart. Cytokine Growth Factor Rev. Dec. 1996;7(4):341-54.
Millenium Pharmaceuticals, Inc. Millenium Pharmaceuticals Identifies a Key mediator of Allergic Immune Response. Press Release Oct. 4, 1999, 2 pages.
Mitcham et al., T1/ST2 signaling establishes it as a member of an expanding interleukin-1 receptor family. J Biol Chem. Mar. 8, 1996;271(10):5777-83.
Monoclonal Antibody: Anti-Human ST2; Medical & Biological Laboratories Co., Ltd., Aug. 23, 2000 (2 pages).
Mueller et al., "Increased Plasma Concentrations of Soluble ST2 are Predictive for 1-Year Mortality in Patients with Acute Destabilized Heart Failure," Clinical Chemistry, 54:752-756 (2008).
Mueller et al., "Use of B-type natriuretic peptide in the evaluation and management of acute dyspnea," New England Journal of Medicine, 350(7):647-654 (2004). (20060-0006EP Search).
Mukoyama et al., Augmented secretion of brain natriuretic peptide in acute myocardial infarction. Biochem Biophys Res Commun. Oct. 15, 1991;180(1):431-6. Abstract Only.
Murphy et al., Signaling and transcription in T helper development. Annu Rev Immunol. 2000;18:451-94.
Murray et al., Chronic beta-adrenergic stimulation induces myocardial proinflammatory cytokine expression. Circulation. May 23, 2000;101(20):2338-41.
Nakano M, et al. Characterization of Soluble Thrombomodulin Fragments in Human Urine. Thromb. Haemost. 1998; 79(2):331-337.
Nakano M, et al. Elevation of Soluble Thrombomodulin Antigen Levels in the Serum and Urine of Streptozotocin-Induced Diabetes Model Rats. Thrombosis Research 2000; 99:83-91.
NCBI BLASTN 2.0.14 [Jun. 29, 2000], BLAST Results, 2065 letters, (5 pages) printed Aug. 23, 2000.
NCBI BLASTN 2.0.14 [Jun. 29, 2000], BLAST Results, 2586 letters, (5 pages) printed Aug. 23, 2000.
NCBI BLASTN 2.2.2 [Dec. 14, 2001], BLAST Results (15 pages).
NCBI BLASTN 2.2.2 [Dec. 14, 2001], BLAST Results (21 pages).
Ng et al., Diagnosis of heart failure using urinary natriuretic peptides. Clin Sci (Load). Feb. 2004;106(2):129-33.
Nichols et al., The influence of 'diastolic' length on the contractility of isolated cat papillary muscle. J Physiol. Apr. 1985;361:269-79.
Notice of Allowance as issued in U.S. Appl. No. 10/024,607 on Jul. 5, 2007.

(56) References Cited

OTHER PUBLICATIONS

Notice of Allowance as issued in U.S. Appl. No. 10/435,482 on Apr. 3, 2007.
Notice of Allowance as issued in U.S. Appl. No. 10/435,482 on Oct. 3, 2007.
Nozaki et al., Soluble Tumor Necrosis Factor Receptors are Elevated in Relation to Severity of Congestive Heart Failure, Jpn Circ J 1997; 61:657-64.
O'Neill et al., The IL-1 receptor/toll-like receptor superfamily: crucial receptors for inflammation and host defense. Immunol Today. May 2000;21(5):206-9.
Office Action as issued in U.S. Appl. No. 10/024,607 Mar. 29, 2006.
Office Action as issued in U.S. Appl. No. 10/024,607 on Jul. 27, 2006.
Office Action as issued in U.S. Appl. No. 10/024,607 on Oct. 7, 2005.
Office Action as issued in U.S. Appl. No. 10/435,482 on May 2, 2008.
Office Action as issued in U.S. Appl. No. 10/435,482 on Oct. 18, 2006.
Ohki R et al. Identification of mechanically induced genes in human monocytic cells by DNA microarrays. J. Hypertens., Apr. 2002; 20(4):685-691 Abstract Only.
Ohtsuka et al., Effect of beta-blockers on circulating levels of inflammatory and anti-inflammatory cytokines in patients with dilated cardiomyopathy. J Am Coll Cardiol. Feb. 2001;37(2):412-7.
Onda H, et al. Identification of Genes Differentially Expressed in Canine Vasospastic Cerebral Arteries After Subarachnoid Hemorrhage. Journal of Cerebral Blood Flow & Metabolism 1999; 19:1279-1288.
Ørntoft et al., Genome-wide study of gene copy numbers, transcripts, and protein levels in pairs of non-invasive and invasive human transitional cell carcinomas. Mol Cell Proteomics. Jan. 2002;1(1):37-45.
Orús et al., Prognostic Value of Serum Cytokines in Patients with Congestive Heart Failure, J Heart Lung Transplant 2000; 19:419-25.
Oshikawa et al., "Acute eosinophilic pneumonia with increased soluble ST2 in serum and bronchoalveolarlavage fluid," Respir. Med., 95(6):532-533 (2001).
Oshikawa et al., "Elevated Soluble ST2 Protein Levels in Sera of Patients with Asthma with an Acute Exacerbation," Am. J. Respir. Crit. Care Med. 164:277-281 (2001).
Papapetropoulos A, et al. Nitric oxide synthase inhibitors attenuate transforming-growth-factor-beta 1-stimulated capillary organization in vitro. Am J Pathol. May 1997; 150(5):1835-44.
PCT/US01/46816 Feb. 19, 2003 Invitation to Pay Additional Fees.
PCT/US03/14882 Feb. 9, 2005 International Search Report.
PCT/US07/10925 Apr. 18, 2008 International Search Report and Written Opinion.
Potter et al., Mutations in the murine fitness 1 gene result in defective hematopoiesis. Blood. Sep. 1, 1997;90(5):1850-7.
Prabhu et al., beta-adrenergic blockade in developing heart failure: effects on myocardial inflammatory cytokines, nitric oxide, and remodeling. Circulation. May 2, 2000;101(17):2103-9.
Pulkki et al., Cytokines and cardiomyocyte death. Ann Med. Aug. 1997;29(4):339-43.
Response to Office Action as filed on Oct. 23, 2006, in U.S. Appl. No. 10/024,607.
Richards et al., "Plasma N-terminal pro-brain natriuretic peptide and adrenomedullin: new neurohormonal predictors of left ventricular function and prognosis after myocardial infarction," Circulation, 97:1921-1929 (1998).
Ridker et al., "Inflammation, Aspirin, and the Risk of Cardiovascular Disease in Apparently Healthy Men," New England J. Med., 336:973-979 (1997).
Rohde et al., "Circulating Cell Adhesion Molecules Are Correlated With Ultrasound-Based Assessment of Carotid Atherosclerosis," Arterial Sclerotic Vasc. Biol., 18:1765-1770 (1998).
Rohde et al., "Plasma Concentrations of Interleukin-6 and Abdominal Aortic Diameter Among Subjects Without Aortic Dilatation," Arterial Sclerotic Vasc. Biol., 19:1695-1699 (1999).
Roig et al., Serum interleukin-6 in congestive heart failure secondary to idiopathic dilated cardiomyopathy. Am J Cardiol. Sep. 1, 1998;82(5):688-90, A8.
Saccani et al., Divergent effects of LPS on expression of IL-1 receptor family members in mononuclear phagocytes in vitro and in vivo. Cytokine. Oct. 1998;10(10):773-80.
Schaffer et al., Device for the application of a dynamic biaxially uniform and isotropic strain to a flexible cell culture membrane. J Orthop Res. Sep. 1994;12(5):709-19.
Selvais et al., J Card Fail, Sep. 2000; 6(3):201-7. (Abstract Only).
Shimpo et al., "Serum levels of the interleukin-1 receptor family member ST2 predict mortality and clinical outcome in acute myocardial infarction" Circulation, 109(18):2186-2190 (2004).
Sims Je, IL-1 and IL-18 Receptors, and Their Extended Family. Current Opinion in Immunology. 2002; 14:117-122.
Strunk et al., "Impact of the history of congestive heart failure on the utility of B-type natriuretic peptide in the emergency diagnosis of heart failure: results from the Breathing Not Properly Multinational Study," Am. J. Med., 119(1):69 e1-11 (2006).
Sussman et al., Dance band on the Titanic: biomechanical signaling in cardiac hypertrophy. Circ Res. Nov. 2002 15;91(10):888-98.
Sutton et al., Left ventricular remodeling after myocardial infarction: pathophysiology and therapy. Circulation. Jun. 27, 2000;101(25):2981-8.
Svensson et al., "Prognostic value of biochemical markers, 12-lead ECG and patient characteristics amongst patients calling for an ambulance due to a suspected acute coronary syndrome," Journal of Internal Medicine, 255(4):469-477 (2004).
Tajima et al., "The increase in serum soluble ST2 protein upon acute exacerbation of idiopathic pulmonary fibrosis," Chest, 124(4):1206-1214 (2003). (cited in 0003CA Aug. 31, 2010).
Tang Z, et al. Gene Expression profiling during the transition to failure in TNF-α over-expressing mice demonstrates the development of autoimmune myocarditis. Journal of Molecular and Cellular Cardiology 2004; 36:515-30.
Tominaga et al., [ST2 gene: a gene that is induced by growth stimulation and encoding a product highly similar to the interleukin 1 receptors] Seikagaku. May 1995;67(5):356-64. Review. Japanese.
Tominaga et al., "Nucleotide sequence of a complementary DNA for human ST2," Biochim. Biophys. Acta., 1171:215-218 (1992). (Abstract Only).
Tominaga et al., The existence of a growth-specific DNA binding factor for the promoter region of mouse ST2 gene. FEBS Lett. Nov. 14, 1994;354(3):311-4.
Tominaga, FEBS Lett., "A putative protein of a growth specific cDNA from BALB/c-3T3 cells is highly similar to the extracellular portion of mouse interleukin 1 receptor," FEBS Lett., 258:301-304 (1989).
Townsend et al., T1/ST2-deficient mice demonstrate the importance of T1/ST2 in developing primary T helper cell type 2 responses. J Exp Med. Mar. 20, 2000;191(6):1069-76.
Trehu et al., Phase I trial of interleukin 2 in combination with the soluble tumor necrosis factor receptor p75 IgG chimera. Clin Cancer Res. Aug. 1996;2(8):1341-51.
Tsutamoto et al., Interleukin-6 spillover in the peripheral circulation increases with the severity of heart failure, and the high plasma level of interleukin-6 is an important prognostic predictor in patients with congestive heart failure. J Am Coll Cardiol. Feb. 1998;31(2):391-8.
Tung et al., Influence of stretch on excitation threshold of single frog ventricular cells. Exp Physiol. Mar. 1995;80(2):221-35.
Vahl et al., Length dependence of calcium- and force-transients in normal and failing human myocardium. J Mol Cell Cardiol. May 1998;30(5):957-66.
Van Kimmenade et al., Utility of amino-terminal pro-brain natriuretic peptide, galectin-3, and apelin for the evaluation of patients with acute heart failure. J Am Coll Cardiol. Sep. 19, 2006;48(6):1217-24.
Vidal et al., Prognostic Value of Cytokines and Neurohormones in Severe Heart Failure, Rev Esp Cardiol 2002; 55(5):481-6.
Wang et al., "Expression of Interleukin-1β, Interleukin-1 Receptor, and Interleukin-1 Receptor Antagonist mRNA in Rat Carotid Artery after Balloon Angioplasty," Biochem. Biophyl. Res. Comm., 271:138-143 (2000).
Weinberg et al., "Expression and regulation of ST2, an interleukin-1 receptor family member, in cardiomyocytes and myocardial infarction," Circulation, 106(23):2961-2966 (2002).

(56) References Cited

OTHER PUBLICATIONS

Weinberg et al., "Identification of serum soluble ST2 receptor as a novel heart failure biomarker," Circulation, 107(5):721-726 (2003).
Yamamoto et al., Induction of tenascin-C in cardiac myocytes by mechanical deformation. Role of reactive oxygen species. J Biol Chem. Jul. 30, 1999;274(31):21840-6.
Yamamoto et al., Mechanical strain suppresses inducible nitric-oxide synthase in cardiac myocytes. J Biol Chem. May 8, 1998;273(19):11862-6.
Yamamoto et al., Regulation of cardiomyocyte mechanotransduction by the cardiac cycle. Circulation. Mar. 13, 2001;103(10):1459-64.
Yamaoka et al., Anti-inflammatory cytokine profile in human heart failure: behavior of interleukin-10 in association with tumor necrosis factor-alpha. Jpn Circ J. Dec. 1999;63(12):951-6.
Yanagisawa et al., "Murine ST2 gene is a member of the primary response gene family induced by growth factors," FEBS Lett., 302(1):51-53 (1992).
Yanagisawa et al., "Presence of a novel primary response gene ST2L, encoding a product highly similar to the interleukin 1 receptor type 1," FEBS Lett. 318(1):83-87 (1993).
Yanagisawa et al., the expression of ST2 gene in helper T cells and the binding of ST2 protein to myeloma-derived RPMI8226 cells. J Biochem (Tokyo). Jan. 1997;121(1):95-103.
Zebrack et al., Usefulness of high-sensitivity C-reactive protein in predicting long-term risk of death or acute myocardial infarction in patients with unstable or stable angina pectoris or acute myocardial infarction. Am J Cardiol. Jan. 15, 2002;89(2):145-9.
Notice of Reasons for Rejection; JP 2009-173539; Sep. 20, 2011; 2 pp.
Communication Pursuant to Article 94(3) EPC; EP 10 184 644.2; Dec. 10, 2012; 5 pp.
Communication Pursuant to Article 94(3) EPC; EP 10 184 644.2; Feb. 2, 2012; 6 pp.
Communication Pursuant to Article 94(3) EPC; EP 03 728 848.7; Nov. 30, 2009; 11 pp.
Communication Pursuant to Article 94(3) EPC; EP 03 728 848.7; Nov. 30, 2009; 6 pp.
Supplementary EP Search Report; EP 03 72 8848; Dec. 15, 2005; 3 pp.
Fourth Office Action (English Translation); CN 03 816 298.9; Aug 12, 2011; 3 pp.
Canadian Office Action; 2,484,897; Mar. 21, 2013; 2 pp.
Canadian Office Action; 2,484,897; Feb. 24, 2012; 3 pp.
Canadian Office Action; 2,484,897; Dec. 20, 2010; 5 pp.
Office Action; U.S. Appl. No. 11/441,780; Mar. 26, 2008; 14 pp.
Amendment in Response to Non-Final Office Action; U.S. Appl. No. 11/441,780; Sep. 26, 2008; 11 pp.
USPTO Communication; U.S. Appl. No. 11/441,780; Oct. 17, 2008; 2 pp.
Office Action; U.S. Appl. No. 11/441,780; Mar. 4, 2009; 11 pp.
Amendment After Final Action; U.S. Appl. No. 11/441,780; Jul 2, 2009; 13 pp.
Notice of Allowance and Fee(s) Due; U.S. Appl. No. 11/441,780; Sep. 22, 2009; 9 pp.
Restriction Requirement; U.S. Appl. No. 12/614,970; Sep. 28, 2010; 4 pp.
Response to Restriction Requirement; U.S. Appl. No. 12/614,970; Oct. 27, 2010; 1 pp.
Office Action; U.S. Appl. No. 12/614,970; Jan. 6, 2011; 5 pp.
Amendment in Reply to Action of Jan. 6, 2011; U.S. Appl. No. 12/614,970; Mar. 2, 2011; 7 pp.
Notice of Allowance; U.S. Appl. No. 12/614,970; May 6, 2011; 6 pp.
Corrected Amendment in Response to Non-Final Office Action; U.S. Appl. No. 11/441,780; Nov. 17, 2008; 11 pp.
Communication Pursuant to Article 94(3) EPC; EP 03 728 848.7 ; Jun. 7, 2010; 7 pp.
EP Search Report; EP 10 184 644; May 2, 2011; 7pp.
International Search Report; WO2003094856; Feb. 9, 2005; 1p.

* cited by examiner

SEQUENCE LISTING

```
<160> NUMBER OF SEQ ID NOS: 8

<210> SEQ ID NO 1
<211> LENGTH: 1357
<212> TYPE: DNA
<213> ORGANISM: Homo sapiens
<220> FEATURE:
```

```
<221> NAME/KEY: CDS
<222> LOCATION: (47)..(1033)
<223> OTHER INFORMATION: HUMST2M, D12763, NM_003856

<400> SEQUENCE: 1
```

| | | | | | | | | | | | | | | |
|---|---|---|---|---|---|---|---|---|---|---|---|---|---|---|
| atctcaacaa | cgagttacca | atacttgctc | ttgattgata | aacaga | atg | ggg | ttt | | | | | | | 55 |
| | | | | | Met | Gly | Phe | | | | | | | |
| | | | | | 1 | | | | | | | | | |

| tgg | atc | tta | gca | att | ctc | aca | att | ctc | atg | tat | tcc | aca | gca | gca | aag | 103 |
|---|---|---|---|---|---|---|---|---|---|---|---|---|---|---|---|---|
| Trp | Ile | Leu | Ala | Ile | Leu | Thr | Ile | Leu | Met | Tyr | Ser | Thr | Ala | Ala | Lys | |
| | 5 | | | | 10 | | | | | 15 | | | | | | |

| ttt | agt | aaa | caa | tca | tgg | ggc | ctg | gaa | aat | gag | gct | tta | att | gta | aga | 151 |
|---|---|---|---|---|---|---|---|---|---|---|---|---|---|---|---|---|
| Phe | Ser | Lys | Gln | Ser | Trp | Gly | Leu | Glu | Asn | Glu | Ala | Leu | Ile | Val | Arg | |
| 20 | | | | | 25 | | | | | 30 | | | | | 35 | |

| tgt | cct | aga | caa | gga | aaa | cct | agt | tac | acc | gtg | gat | tgg | tat | tac | tca | 199 |
|---|---|---|---|---|---|---|---|---|---|---|---|---|---|---|---|---|
| Cys | Pro | Arg | Gln | Gly | Lys | Pro | Ser | Tyr | Thr | Val | Asp | Trp | Tyr | Tyr | Ser | |
| | | | 40 | | | | | 45 | | | | | 50 | | | |

| caa | aca | aac | aaa | agt | att | ccc | act | cag | gaa | aga | aat | cgt | gtg | ttt | gcc | 247 |
|---|---|---|---|---|---|---|---|---|---|---|---|---|---|---|---|---|
| Gln | Thr | Asn | Lys | Ser | Ile | Pro | Thr | Gln | Glu | Arg | Asn | Arg | Val | Phe | Ala | |
| | | | 55 | | | | | 60 | | | | | 65 | | | |

| tca | ggc | caa | ctt | ctg | aag | ttt | cta | cca | gct | gaa | gtt | gct | gat | tct | ggt | 295 |
|---|---|---|---|---|---|---|---|---|---|---|---|---|---|---|---|---|
| Ser | Gly | Gln | Leu | Leu | Lys | Phe | Leu | Pro | Ala | Glu | Val | Ala | Asp | Ser | Gly | |
| | 70 | | | | | 75 | | | | | 80 | | | | | |

| att | tat | acc | tgt | att | gtc | aga | agt | ccc | aca | ttc | aat | agg | act | gga | tat | 343 |
|---|---|---|---|---|---|---|---|---|---|---|---|---|---|---|---|---|
| Ile | Tyr | Thr | Cys | Ile | Val | Arg | Ser | Pro | Thr | Phe | Asn | Arg | Thr | Gly | Tyr | |
| 85 | | | | | 90 | | | | | 95 | | | | | | |

| gcg | aat | gtc | acc | ata | tat | aaa | aaa | caa | tca | gat | tgc | aat | gtt | cca | gat | 391 |
|---|---|---|---|---|---|---|---|---|---|---|---|---|---|---|---|---|
| Ala | Asn | Val | Thr | Ile | Tyr | Lys | Lys | Gln | Ser | Asp | Cys | Asn | Val | Pro | Asp | |
| 100 | | | | | 105 | | | | | 110 | | | | | 115 | |

| tat | ttg | atg | tat | tca | aca | gta | tct | gga | tca | gaa | aaa | aat | tcc | aaa | att | 439 |
|---|---|---|---|---|---|---|---|---|---|---|---|---|---|---|---|---|
| Tyr | Leu | Met | Tyr | Ser | Thr | Val | Ser | Gly | Ser | Glu | Lys | Asn | Ser | Lys | Ile | |
| | | | 120 | | | | | 125 | | | | | 130 | | | |

| tat | tgt | cct | acc | att | gac | ctc | tac | aac | tgg | aca | gca | cct | ctt | gag | tgg | 487 |
|---|---|---|---|---|---|---|---|---|---|---|---|---|---|---|---|---|
| Tyr | Cys | Pro | Thr | Ile | Asp | Leu | Tyr | Asn | Trp | Thr | Ala | Pro | Leu | Glu | Trp | |
| | | | 135 | | | | | 140 | | | | | 145 | | | |

| ttt | aag | aat | tgt | cag | gct | ctt | caa | gga | tca | agg | tac | agg | gcg | cac | aag | 535 |
|---|---|---|---|---|---|---|---|---|---|---|---|---|---|---|---|---|
| Phe | Lys | Asn | Cys | Gln | Ala | Leu | Gln | Gly | Ser | Arg | Tyr | Arg | Ala | His | Lys | |
| | | 150 | | | | | 155 | | | | | 160 | | | | |

| tca | ttt | ttg | gtc | att | gat | aat | gtg | atg | act | gag | gac | gca | ggt | gat | tac | 583 |
|---|---|---|---|---|---|---|---|---|---|---|---|---|---|---|---|---|
| Ser | Phe | Leu | Val | Ile | Asp | Asn | Val | Met | Thr | Glu | Asp | Ala | Gly | Asp | Tyr | |
| | 165 | | | | | 170 | | | | | 175 | | | | | |

| acc | tgt | aaa | ttt | ata | cac | aat | gaa | aat | gga | gcc | aat | tat | agt | gtg | acg | 631 |
|---|---|---|---|---|---|---|---|---|---|---|---|---|---|---|---|---|
| Thr | Cys | Lys | Phe | Ile | His | Asn | Glu | Asn | Gly | Ala | Asn | Tyr | Ser | Val | Thr | |
| 180 | | | | | 185 | | | | | 190 | | | | | 195 | |

| gcg | acc | agg | tcc | ttc | acg | gtc | aag | gat | gag | caa | ggc | ttt | tct | ctg | ttt | 679 |
|---|---|---|---|---|---|---|---|---|---|---|---|---|---|---|---|---|
| Ala | Thr | Arg | Ser | Phe | Thr | Val | Lys | Asp | Glu | Gln | Gly | Phe | Ser | Leu | Phe | |
| | | | 200 | | | | | 205 | | | | | 210 | | | |

| cca | gta | atc | gga | gcc | cct | gca | caa | aat | gaa | ata | aag | gaa | gtg | gaa | att | 727 |
|---|---|---|---|---|---|---|---|---|---|---|---|---|---|---|---|---|
| Pro | Val | Ile | Gly | Ala | Pro | Ala | Gln | Asn | Glu | Ile | Lys | Glu | Val | Glu | Ile | |
| | | | 215 | | | | | 220 | | | | | 225 | | | |

| gga | aaa | aac | gca | aac | cta | act | tgc | tct | gct | tgt | ttt | gga | aaa | ggc | act | 775 |
|---|---|---|---|---|---|---|---|---|---|---|---|---|---|---|---|---|
| Gly | Lys | Asn | Ala | Asn | Leu | Thr | Cys | Ser | Ala | Cys | Phe | Gly | Lys | Gly | Thr | |
| | | 230 | | | | | 235 | | | | | 240 | | | | |

| cag | ttc | ttg | gct | gcc | gtc | ctg | tgg | cag | ctt | aat | gga | aca | aaa | att | aca | 823 |
|---|---|---|---|---|---|---|---|---|---|---|---|---|---|---|---|---|
| Gln | Phe | Leu | Ala | Ala | Val | Leu | Trp | Gln | Leu | Asn | Gly | Thr | Lys | Ile | Thr | |
| | 245 | | | | | 250 | | | | | 255 | | | | | |

| gac | ttt | ggt | gaa | cca | aga | att | caa | caa | gag | gaa | ggg | caa | aat | caa | agt | 871 |
|---|---|---|---|---|---|---|---|---|---|---|---|---|---|---|---|---|
| Asp | Phe | Gly | Glu | Pro | Arg | Ile | Gln | Gln | Glu | Glu | Gly | Gln | Asn | Gln | Ser | |
| 260 | | | | | 265 | | | | | 270 | | | | | 275 | |

| ttc | agc | aat | ggg | ctg | gct | tgt | cta | gac | atg | gtt | tta | aga | ata | gct | gac | 919 |
|---|---|---|---|---|---|---|---|---|---|---|---|---|---|---|---|---|
| Phe | Ser | Asn | Gly | Leu | Ala | Cys | Leu | Asp | Met | Val | Leu | Arg | Ile | Ala | Asp | |

```
                280                 285                 290
gtg aag gaa gag gat tta ttg ctg cag tac gac tgt ctg gcc ctg aat    967
Val Lys Glu Glu Asp Leu Leu Leu Gln Tyr Asp Cys Leu Ala Leu Asn
            295                 300                 305 ttg cat ggc ttg aga agg cac acc gta aga cta agt agg aaa aat cca   1015
Leu His Gly Leu Arg Arg His Thr Val Arg Leu Ser Arg Lys Asn Pro
        310                 315                 320 agt aag gag tgt ttc tga gactttgatc acctgaactt tctctagcaa          1063
Ser Lys Glu Cys Phe
    325 gtgtaagcag aatggagtgt ggttccaaga gatccatcaa gacaatggga atggcctgtg  1123 ccataaaatg tgcttctctt cttcgggatg ttgtttgctg tctgatcttt gtagactgtt  1183 cctgtttgct gggagcttct ctgctgctta aattgttcgt cctcccccac tccctcctat  1243 cgttggtttg tctagaacac tcagctgctt ctttggtcat ccttgttttc taactttatg  1303 aactccctct gtgtcactgt atgtgaaagg aaatgcacca acaaccgaaa actg        1357

<210> SEQ ID NO 2
<211> LENGTH: 328
<212> TYPE: PRT
<213> ORGANISM: Homo sapiens

<400> SEQUENCE: 2

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255
```

```
Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325

<210> SEQ ID NO 3
<211> LENGTH: 2058
<212> TYPE: DNA
<213> ORGANISM: Homo sapiens
<220> FEATURE:
<221> NAME/KEY: CDS
<222> LOCATION: (272)..(1942)
<223> OTHER INFORMATION: AB012701

<400> SEQUENCE: 3
aaagagaggc tggctgttgt atttagtaaa gctataaagc tgtaagagaa attggctttc      60
tgagttgtga aactgtgggc agaaagttga ggaagaaaga actcaagtac aacccaatga     120
ggttgagata taggctactc ttcccaactc agtcttgaag agtatcacca actgcctcat     180
gtgtggtgac cttcactgtc gtatgccagt gactcatctg gagtaatctc aacaacgagt     240
taccaatact tgctcttgat tgataaacag a atg ggg ttt tgg atc tta gca        292
                                  Met Gly Phe Trp Ile Leu Ala
                                    1               5 att ctc aca att ctc atg tat tcc aca gca gca aag ttt agt aaa caa       340
Ile Leu Thr Ile Leu Met Tyr Ser Thr Ala Ala Lys Phe Ser Lys Gln
         10                  15                  20 tca tgg ggc ctg gaa aat gag gct tta att gta aga tgt cct aga caa       388
Ser Trp Gly Leu Glu Asn Glu Ala Leu Ile Val Arg Cys Pro Arg Gln
 25                  30                  35 gga aaa cct agt tac acc gtg gat tgg tat tac tca caa aca aac aaa       436
Gly Lys Pro Ser Tyr Thr Val Asp Trp Tyr Tyr Ser Gln Thr Asn Lys
 40                  45                  50                  55 agt att ccc act cag gaa aga aat cgt gtg ttt gcc tca ggc caa ctt       484
Ser Ile Pro Thr Gln Glu Arg Asn Arg Val Phe Ala Ser Gly Gln Leu
             60                  65                  70 ctg aag ttt cta cca gct gaa gtt gct gat tct ggt att tat acc tgt       532
Leu Lys Phe Leu Pro Ala Glu Val Ala Asp Ser Gly Ile Tyr Thr Cys
         75                  80                  85 att gtc aga agt ccc aca ttc aat agg act gga tat gcg aat gtc acc       580
Ile Val Arg Ser Pro Thr Phe Asn Arg Thr Gly Tyr Ala Asn Val Thr
     90                  95                 100 ata tat aaa aaa caa tca gat tgc aat gtt cca gat tat ttg atg tat       628
Ile Tyr Lys Lys Gln Ser Asp Cys Asn Val Pro Asp Tyr Leu Met Tyr
105                 110                 115 tca aca gta tct gga tca gaa aaa aat tcc aaa att tat tgt cct acc       676
Ser Thr Val Ser Gly Ser Glu Lys Asn Ser Lys Ile Tyr Cys Pro Thr
120                 125                 130                 135 att gac ctc tac aac tgg aca gca cct ctt gag tgg ttt aag aat tgt       724
Ile Asp Leu Tyr Asn Trp Thr Ala Pro Leu Glu Trp Phe Lys Asn Cys
             140                 145                 150 cag gct ctt caa gga tca agg tac agg gcg cac aag tca ttt ttg gtc       772
Gln Ala Leu Gln Gly Ser Arg Tyr Arg Ala His Lys Ser Phe Leu Val
         155                 160                 165 att gat aat gtg atg act gag gac gca ggt gat tac acc tgt aaa ttt       820
```

-continued

| | | |
|---|---|---|
| Ile Asp Asn Val Met Thr Glu Asp Ala Gly Asp Tyr Thr Cys Lys Phe<br>170                       175                       180 | | |
| ata cac aat gaa aat gga gcc aat tat agt gtg acg gcg acc agg tcc<br>Ile His Asn Glu Asn Gly Ala Asn Tyr Ser Val Thr Ala Thr Arg Ser<br>185                       190                       195 | 868 | |
| ttc acg gtc aag gat gag caa ggc ttt tct ctg ttt cca gta atc gga<br>Phe Thr Val Lys Asp Glu Gln Gly Phe Ser Leu Phe Pro Val Ile Gly<br>200                       205                     210                   215 | 916 | |
| gcc cct gca caa aat gaa ata aag gaa gtg gaa att gga aaa aac gca<br>Ala Pro Ala Gln Asn Glu Ile Lys Glu Val Glu Ile Gly Lys Asn Ala<br>                    220                     225                       230 | 964 | |
| aac cta act tgc tct gct tgt ttt gga aaa ggc act cag ttc ttg gct<br>Asn Leu Thr Cys Ser Ala Cys Phe Gly Lys Gly Thr Gln Phe Leu Ala<br>                 235                     240                     245 | 1012 | |
| gcc gtc ctg tgg cag ctt aat gga aca aaa att aca gac ttt ggt gaa<br>Ala Val Leu Trp Gln Leu Asn Gly Thr Lys Ile Thr Asp Phe Gly Glu<br>            250                     255                     260 | 1060 | |
| cca aga att caa caa gag gaa ggg caa aat caa agt ttc agc aat ggg<br>Pro Arg Ile Gln Gln Glu Glu Gly Gln Asn Gln Ser Phe Ser Asn Gly<br>265                       270                       275 | 1108 | |
| ctg gct tgt cta gac atg gtt tta aga ata gct gac gtg aag gaa gag<br>Leu Ala Cys Leu Asp Met Val Leu Arg Ile Ala Asp Val Lys Glu Glu<br>280                       285                     290                   295 | 1156 | |
| gat tta ttg ctg cag tac gac tgt ctg gcc ctg aat ttg cat ggc ttg<br>Asp Leu Leu Leu Gln Tyr Asp Cys Leu Ala Leu Asn Leu His Gly Leu<br>                 300                     305                     310 | 1204 | |
| aga agg cac acc gta aga cta agt agg aaa aat cca att gat cat cat<br>Arg Arg His Thr Val Arg Leu Ser Arg Lys Asn Pro Ile Asp His His<br>                 315                     320                     325 | 1252 | |
| agc atc tac tgc ata att gca gta tgt agt gta ttt tta atg cta atc<br>Ser Ile Tyr Cys Ile Ile Ala Val Cys Ser Val Phe Leu Met Leu Ile<br>            330                     335                     340 | 1300 | |
| aat gtc ctg gtt atc atc cta aaa atg ttc tgg att gag gcc act ctg<br>Asn Val Leu Val Ile Ile Leu Lys Met Phe Trp Ile Glu Ala Thr Leu<br>345                       350                     355 | 1348 | |
| ctc tgg aga gac ata gct aaa cct tac aag act agg aat gat gga aag<br>Leu Trp Arg Asp Ile Ala Lys Pro Tyr Lys Thr Arg Asn Asp Gly Lys<br>360                       365                     370                   375 | 1396 | |
| ctc tat gat gct tat gtt gtc tac cca cgg aac tac aaa tcc agt aca<br>Leu Tyr Asp Ala Tyr Val Val Tyr Pro Arg Asn Tyr Lys Ser Ser Thr<br>                 380                     385                     390 | 1444 | |
| gat ggg gcc agt cgt gta gag cac ttt gtt cac cag att ctg cct gat<br>Asp Gly Ala Ser Arg Val Glu His Phe Val His Gln Ile Leu Pro Asp<br>                 395                     400                     405 | 1492 | |
| gtt ctt gaa aat aaa tgt ggc tat acc tta tgc att tat ggg aga gat<br>Val Leu Glu Asn Lys Cys Gly Tyr Thr Leu Cys Ile Tyr Gly Arg Asp<br>            410                     415                     420 | 1540 | |
| atg cta cct gga gaa gat gta gtc act gca gtg gaa acc aac ata cga<br>Met Leu Pro Gly Glu Asp Val Val Thr Ala Val Glu Thr Asn Ile Arg<br>425                       430                     435 | 1588 | |
| aag agc agg cgg cac att ttc atc ctg acc cct cag atc act cac aat<br>Lys Ser Arg Arg His Ile Phe Ile Leu Thr Pro Gln Ile Thr His Asn<br>440                       445                     450                   455 | 1636 | |
| aag gag ttt gcc tac gag cag gag gtt gcc ctg cac tgt gcc ctc atc<br>Lys Glu Phe Ala Tyr Glu Gln Glu Val Ala Leu His Cys Ala Leu Ile<br>                 460                     465                     470 | 1684 | |
| cag aac gac gcc aag gtg ata ctt att gag atg gag gct ctg agc gag<br>Gln Asn Asp Ala Lys Val Ile Leu Ile Glu Met Glu Ala Leu Ser Glu<br>            475                     480                     485 | 1732 | |
| ctg gac atg ctg cag gct gag gcg ctt cag gac tcc ctc cag cat ctt | 1780 | |

-continued

| | | | | | | | | | | | |
|---|---|---|---|---|---|---|---|---|---|---|---|
| Leu | Asp | Met | Leu | Gln | Ala | Glu | Ala | Leu | Gln | Asp | Ser | Leu | Gln | His | Leu |
| | | 490 | | | | 495 | | | | 500 | |

```
atg aaa gta cag ggg acc atc aag tgg agg gag gac cac att gcc aat    1828
Met Lys Val Gln Gly Thr Ile Lys Trp Arg Glu Asp His Ile Ala Asn
    505                 510                 515 aaa agg tcc ctg aat tcc aaa ttc tgg aag cac gtg agg tac caa atg    1876
Lys Arg Ser Leu Asn Ser Lys Phe Trp Lys His Val Arg Tyr Gln Met
520                 525                 530                 535 cct gtg cca agc aaa att ccc aga aag gcc tct agt ttg act ccc ttg    1924
Pro Val Pro Ser Lys Ile Pro Arg Lys Ala Ser Ser Leu Thr Pro Leu
                540                 545                 550 gct gcc cag aag caa tag tgcctgctgt gatgtgcaaa gggatctggg           1972
Ala Ala Gln Lys Gln
                555 tttgaagctt tcctgacttc tcctagctgg cttatgcccc tgcactgaag tgtgaggagc  2032 gggaatatta aaggattca ggccac                                        2058

<210> SEQ ID NO 4
<211> LENGTH: 556
<212> TYPE: PRT
<213> ORGANISM: Homo sapiens

<400> SEQUENCE: 4
```

| Met | Gly | Phe | Trp | Ile | Leu | Ala | Ile | Leu | Thr | Ile | Leu | Met | Tyr | Ser | Thr |
|---|---|---|---|---|---|---|---|---|---|---|---|---|---|---|---|
| 1 | | | | 5 | | | | | 10 | | | | | 15 | |

| Ala | Ala | Lys | Phe | Ser | Lys | Gln | Ser | Trp | Gly | Leu | Glu | Asn | Glu | Ala | Leu |
|---|---|---|---|---|---|---|---|---|---|---|---|---|---|---|---|
| | | | | 20 | | | | | 25 | | | | | 30 | |

| Ile | Val | Arg | Cys | Pro | Arg | Gln | Gly | Lys | Pro | Ser | Tyr | Thr | Val | Asp | Trp |
|---|---|---|---|---|---|---|---|---|---|---|---|---|---|---|---|
| | | | 35 | | | | | 40 | | | | | 45 | | |

| Tyr | Tyr | Ser | Gln | Thr | Asn | Lys | Ser | Ile | Pro | Thr | Gln | Glu | Arg | Asn | Arg |
|---|---|---|---|---|---|---|---|---|---|---|---|---|---|---|---|
| | 50 | | | | | 55 | | | | | 60 | | | | |

| Val | Phe | Ala | Ser | Gly | Gln | Leu | Leu | Lys | Phe | Leu | Pro | Ala | Glu | Val | Ala |
|---|---|---|---|---|---|---|---|---|---|---|---|---|---|---|---|
| 65 | | | | | 70 | | | | | 75 | | | | | 80 |

| Asp | Ser | Gly | Ile | Tyr | Thr | Cys | Ile | Val | Arg | Ser | Pro | Thr | Phe | Asn | Arg |
|---|---|---|---|---|---|---|---|---|---|---|---|---|---|---|---|
| | | | | 85 | | | | | 90 | | | | | 95 | |

| Thr | Gly | Tyr | Ala | Asn | Val | Thr | Ile | Tyr | Lys | Lys | Gln | Ser | Asp | Cys | Asn |
|---|---|---|---|---|---|---|---|---|---|---|---|---|---|---|---|
| | | | | 100 | | | | | 105 | | | | | 110 | |

| Val | Pro | Asp | Tyr | Leu | Met | Tyr | Ser | Thr | Val | Ser | Gly | Ser | Glu | Lys | Asn |
|---|---|---|---|---|---|---|---|---|---|---|---|---|---|---|---|
| | | | | 115 | | | | | 120 | | | | | 125 | |

| Ser | Lys | Ile | Tyr | Cys | Pro | Thr | Ile | Asp | Leu | Tyr | Asn | Trp | Thr | Ala | Pro |
|---|---|---|---|---|---|---|---|---|---|---|---|---|---|---|---|
| | 130 | | | | | 135 | | | | | 140 | | | | |

| Leu | Glu | Trp | Phe | Lys | Asn | Cys | Gln | Ala | Leu | Gln | Gly | Ser | Arg | Tyr | Arg |
|---|---|---|---|---|---|---|---|---|---|---|---|---|---|---|---|
| 145 | | | | | 150 | | | | | 155 | | | | | 160 |

| Ala | His | Lys | Ser | Phe | Leu | Val | Ile | Asp | Asn | Val | Met | Thr | Glu | Asp | Ala |
|---|---|---|---|---|---|---|---|---|---|---|---|---|---|---|---|
| | | | | 165 | | | | | 170 | | | | | 175 | |

| Gly | Asp | Tyr | Thr | Cys | Lys | Phe | Ile | His | Asn | Glu | Asn | Gly | Ala | Asn | Tyr |
|---|---|---|---|---|---|---|---|---|---|---|---|---|---|---|---|
| | | | | 180 | | | | | 185 | | | | | 190 | |

| Ser | Val | Thr | Ala | Thr | Arg | Ser | Phe | Thr | Val | Lys | Asp | Glu | Gln | Gly | Phe |
|---|---|---|---|---|---|---|---|---|---|---|---|---|---|---|---|
| | | | 195 | | | | | 200 | | | | | 205 | | |

| Ser | Leu | Phe | Pro | Val | Ile | Gly | Ala | Pro | Ala | Gln | Asn | Glu | Ile | Lys | Glu |
|---|---|---|---|---|---|---|---|---|---|---|---|---|---|---|---|
| | 210 | | | | | 215 | | | | | 220 | | | | |

| Val | Glu | Ile | Gly | Lys | Asn | Ala | Asn | Leu | Thr | Cys | Ser | Ala | Cys | Phe | Gly |
|---|---|---|---|---|---|---|---|---|---|---|---|---|---|---|---|
| 225 | | | | | 230 | | | | | 235 | | | | | 240 |

| Lys | Gly | Thr | Gln | Phe | Leu | Ala | Ala | Val | Leu | Trp | Gln | Leu | Asn | Gly | Thr |
|---|---|---|---|---|---|---|---|---|---|---|---|---|---|---|---|
| | | | | 245 | | | | | 250 | | | | | 255 | |

| Lys | Ile | Thr | Asp | Phe | Gly | Glu | Pro | Arg | Ile | Gln | Gln | Glu | Glu | Gly | Gln |
|---|---|---|---|---|---|---|---|---|---|---|---|---|---|---|---|

```
                         260                265                 270
Asn Gln Ser Phe Ser Asn Gly Leu Ala Cys Leu Asp Met Val Leu Arg
                275                 280                 285

Ile Ala Asp Val Lys Glu Glu Asp Leu Leu Leu Gln Tyr Asp Cys Leu
            290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
                325                 330                 335

Ser Val Phe Leu Met Leu Ile Asn Val Leu Val Ile Ile Leu Lys Met
            340                 345                 350

Phe Trp Ile Glu Ala Thr Leu Leu Trp Arg Asp Ile Ala Lys Pro Tyr
                355                 360                 365

Lys Thr Arg Asn Asp Gly Lys Leu Tyr Asp Ala Tyr Val Val Tyr Pro
            370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
                435                 440                 445

Thr Pro Gln Ile Thr His Asn Lys Glu Phe Ala Tyr Glu Gln Glu Val
            450                 455                 460

Ala Leu His Cys Ala Leu Ile Gln Asn Asp Ala Lys Val Ile Leu Ile
465                 470                 475                 480

Glu Met Glu Ala Leu Ser Leu Asp Met Leu Gln Ala Glu Ala Leu
                485                 490                 495

Gln Asp Ser Leu Gln His Leu Met Lys Val Gln Gly Thr Ile Lys Trp
                500                 505                 510

Arg Glu Asp His Ile Ala Asn Lys Arg Ser Leu Asn Ser Lys Phe Trp
                515                 520                 525

Lys His Val Arg Tyr Gln Met Pro Val Pro Ser Lys Ile Pro Arg Lys
            530                 535                 540

Ala Ser Ser Leu Thr Pro Leu Ala Ala Gln Lys Gln
545                 550                 555

<210> SEQ ID NO 5
<211> LENGTH: 2586
<212> TYPE: DNA
<213> ORGANISM: Rattus norvegicus
<220> FEATURE:
<221> NAME/KEY: CDS
<222> LOCATION: (202)..(1212)
<223> OTHER INFORMATION: Fit-1S

<400> SEQUENCE: 5
gggtagtctg aagagaccag aggaaggagc accaagtagc ctcagggccc tgggtttatt      60
cttcccagcc cttcatctgg gctacactga tttctctttt ggaccctaca tcagacagca     120
cacatcaacc gcctagtgga ctcaccgtta ccttcctgtg ccattgccat cggagagatc     180
tcggccatca atcactagca c atg att ggc aaa tgg aga atg ggg ctt tgg     231
                        Met Ile Gly Lys Trp Arg Met Gly Leu Trp
                          1               5                  10 gct ttg gca att ctg aca gtt ccc atg tat ttc ata gtg aca gag ggc     279
Ala Leu Ala Ile Leu Thr Val Pro Met Tyr Phe Ile Val Thr Glu Gly
```

|     |     |     |     |     | 15  |     |     |     |     | 20  |     |     |     |     | 25  |     |     |
|-----|-----|-----|-----|-----|-----|-----|-----|-----|-----|-----|-----|-----|-----|-----|-----|-----|-----|

```
aga aaa aca tcc tgg ggt cta gaa aac gag gct tta att gtc aga tgc      327
Arg Lys Thr Ser Trp Gly Leu Glu Asn Glu Ala Leu Ile Val Arg Cys
         30                  35                  40 ccc caa aga gga ggt gcg att aac cct gtg gaa tgg tat tat tca aat      375
Pro Gln Arg Gly Gly Ala Ile Asn Pro Val Glu Trp Tyr Tyr Ser Asn
     45                  50                  55 aca aat gaa aga att cct act caa aag aga aat cgg atc ttc gtc tca      423
Thr Asn Glu Arg Ile Pro Thr Gln Lys Arg Asn Arg Ile Phe Val Ser
 60                  65                  70 aga gat cgt ctg aag ttt cta cca gcc aaa gtg gaa gac tct ggg att      471
Arg Asp Arg Leu Lys Phe Leu Pro Ala Lys Val Glu Asp Ser Gly Ile
75                  80                  85                  90 tat acg tgt gtt atc aga agc cct gaa tcg att aag acc gga tct ttg      519
Tyr Thr Cys Val Ile Arg Ser Pro Glu Ser Ile Lys Thr Gly Ser Leu
                 95                 100                 105 aat gtc acc ata tat aaa aga cca cca aac tgc aaa atc cct gat tac      567
Asn Val Thr Ile Tyr Lys Arg Pro Pro Asn Cys Lys Ile Pro Asp Tyr
             110                 115                 120 atg atg tac tcg aca gta gat gga tca gat aaa aat tcc aag ata aca      615
Met Met Tyr Ser Thr Val Asp Gly Ser Asp Lys Asn Ser Lys Ile Thr
         125                 130                 135 tgt cca aca att gcc ttg tat aat tgg aca gcg cct gtt cag tgg ttt      663
Cys Pro Thr Ile Ala Leu Tyr Asn Trp Thr Ala Pro Val Gln Trp Phe
     140                 145                 150 aag aac tgc aaa gct ctc caa ggg cca agg ttc agg gca cac atg tcc      711
Lys Asn Cys Lys Ala Leu Gln Gly Pro Arg Phe Arg Ala His Met Ser
155                 160                 165                 170 tat ttg ttc att gac aaa gtg agt cat gtt gat gaa ggt gac tac aca      759
Tyr Leu Phe Ile Asp Lys Val Ser His Val Asp Glu Gly Asp Tyr Thr
                 175                 180                 185 tgt cga ttc act cac acg gag aac gga acc aat tac att gtg act gcc      807
Cys Arg Phe Thr His Thr Glu Asn Gly Thr Asn Tyr Ile Val Thr Ala
             190                 195                 200 acc aga tca ttc aca gtt gaa gaa aaa ggc ttc tct aca ttt cca gta      855
Thr Arg Ser Phe Thr Val Glu Glu Lys Gly Phe Ser Thr Phe Pro Val
         205                 210                 215 att aca aac cct cca cac aac tac aca gtg gaa gtg gaa ata gga aaa      903
Ile Thr Asn Pro Pro His Asn Tyr Thr Val Glu Val Glu Ile Gly Lys
     220                 225                 230 aca gca aac att gcc tgc tca gct tgc ttt ggc aca gcc tct cag ttc      951
Thr Ala Asn Ile Ala Cys Ser Ala Cys Phe Gly Thr Ala Ser Gln Phe
235                 240                 245                 250 gtt gct gtc ctg tgg cag att aac aaa acg aga att gga tct ttt ggc      999
Val Ala Val Leu Trp Gln Ile Asn Lys Thr Arg Ile Gly Ser Phe Gly
                 255                 260                 265 aaa gca aga att caa gaa gag aaa ggc cca aat aaa agt cca agc aat     1047
Lys Ala Arg Ile Gln Glu Glu Lys Gly Pro Asn Lys Ser Ser Ser Asn
             270                 275                 280 ggc atg att tgc tta acc tca ctg tta agg ata act ggt gtg acc gac     1095
Gly Met Ile Cys Leu Thr Ser Leu Leu Arg Ile Thr Gly Val Thr Asp
         285                 290                 295 aag gac ttc tcc ctg aaa tat gac tgt gtg gcc atg aac cat cac gga     1143
Lys Asp Phe Ser Leu Lys Tyr Asp Cys Val Ala Met Asn His His Gly
     300                 305                 310 gtg ata agg cac ccc gta aga ctg aga agg aaa caa cca agt aag gag     1191
Val Ile Arg His Pro Val Arg Leu Arg Arg Lys Gln Pro Ser Lys Glu
315                 320                 325                 330 tgt ctc tca caa att gct tga caaaattggc tgaatttgct gcaaaccaca        1242
Cys Leu Ser Gln Ile Ala
```

```
                    335
atccttttc  tcagaggact  gtgtgttata  gcttggtccc  aggggattca  tcatgatcgt   1302
gggattagtt  ggccagtttc  ctcaaatgtg  tttttcatgt  tgagaaagct  ccttaaatct   1362
ggtctgtcca  gaatgtttct  gtcttctaga  aggactctct  gtcattgtat  ctttcctctc   1422
tctgtttccc  cttgtccttg  ttctcctcac  ggtcctcccc  atcccttcac  cttccttcac   1482
gttctctcta  ctcttcttcc  cttatctctg  ggctccttct  cacctgttag  tggcttcttc   1542 agtcacccctt  tgcacatgct  acaagggaca  ttggtgttga  tactgggttg  gaagcagtaa   1602
taaccctact  gtgtttctcc  ctttgtgact  cttgtaacag  aaacaactt  acacattagg    1662 tggatgacca  acttgatccc  attttaaaag  agtagagaaa  acatgatatt  tttacccctta  1722 acactctctt  atgatactaa  ccactgcctc  aatggcaata  caactaatgt  aaaaacatta   1782
ttttaacttc  tttcaaatat  caagagggtg  tggaagggag  agagacactg  actctaagct   1842
catagtgata  tgtggggcat  ttattgggat  taagatattg  attaaatgat  tagggtgggg   1902
gtacctattg  gataccatca  agctgtgtca  ctgcctgaag  tggtagttgg  attttttttt   1962
tggttctgtt  tgtcttcttt  ggtttgtttt  aactatagag  accattctgc  tcttgaactc   2022
ctagagttcc  acctggcttt  gcctctcagg  tcctgggatt  aaagccatat  gtcaccttac   2082
ccagccagga  tgtttcttgt  tttggtttca  attttagagc  ctctggcttg  taagattttt   2142
ataaagtaga  gtttgattca  taggtggcca  gagttgtgac  tcatagatgg  gttttagtga   2202
ggtcttaggc  atccaccccct  tataatgctg  ttacccaggg  tgactgtgga  ccacagcact   2262
gtgttatgag  atggtggagg  tcatggcaca  ttctatagga  aaagagaagc  caagccccta   2322
gtctcaccag  gcacaacctt  gagtcctcac  tgctctcctc  tgccaacagg  accttttgtc   2382
cagatttctg  agtattctct  agttacattt  gtatttgaac  tatatttgtg  ttatctgtaa   2442
ttctgtattt  gttttgtttg  tgtgtggttt  tgtattttcc  agattatttt  taattcacct   2502
gttgctattc  aaatcaatgt  atctgtactg  cttcatcaac  acagcctgtt  aaataaaagt   2562
cgtgtctgtt  gttgttgaat  gata                                            2586
```

<210> SEQ ID NO 6
<211> LENGTH: 336
<212> TYPE: PRT
<213> ORGANISM: Rattus norvegicus

<400> SEQUENCE: 6

```
Met Ile Gly Lys Trp Arg Met Gly Leu Trp Ala Leu Ala Ile Leu Thr
1               5                   10                  15

Val Pro Met Tyr Phe Ile Val Thr Glu Gly Arg Lys Thr Ser Trp Gly
                20                  25                  30

Leu Glu Asn Glu Ala Leu Ile Val Arg Cys Pro Gln Arg Gly Gly Ala
            35                  40                  45

Ile Asn Pro Val Glu Trp Tyr Tyr Ser Asn Thr Asn Glu Arg Ile Pro
        50                  55                  60

Thr Gln Lys Arg Asn Arg Ile Phe Val Ser Arg Asp Arg Leu Lys Phe
65                  70                  75                  80

Leu Pro Ala Lys Val Glu Asp Ser Gly Ile Tyr Thr Cys Val Ile Arg
                85                  90                  95

Ser Pro Glu Ser Ile Lys Thr Gly Ser Leu Asn Val Thr Ile Tyr Lys
                100                 105                 110

Arg Pro Pro Asn Cys Lys Ile Pro Asp Tyr Met Met Tyr Ser Thr Val
            115                 120                 125
```

```
Asp Gly Ser Asp Lys Asn Ser Lys Ile Thr Cys Pro Thr Ile Ala Leu
            130                 135                 140

Tyr Asn Trp Thr Ala Pro Val Gln Trp Phe Lys Asn Cys Lys Ala Leu
145                 150                 155                 160

Gln Gly Pro Arg Phe Arg Ala His Met Ser Tyr Leu Phe Ile Asp Lys
                165                 170                 175

Val Ser His Val Asp Glu Gly Asp Tyr Thr Cys Arg Phe Thr His Thr
            180                 185                 190

Glu Asn Gly Thr Asn Tyr Ile Val Thr Ala Thr Arg Ser Phe Thr Val
        195                 200                 205

Glu Glu Lys Gly Phe Ser Thr Phe Pro Val Ile Thr Asn Pro Pro His
    210                 215                 220

Asn Tyr Thr Val Glu Val Glu Ile Gly Lys Thr Ala Asn Ile Ala Cys
225                 230                 235                 240

Ser Ala Cys Phe Gly Thr Ala Ser Gln Phe Val Ala Val Leu Trp Gln
                245                 250                 255

Ile Asn Lys Thr Arg Ile Gly Ser Phe Gly Lys Ala Arg Ile Gln Glu
            260                 265                 270

Glu Lys Gly Pro Asn Lys Ser Ser Asn Gly Met Ile Cys Leu Thr
        275                 280                 285

Ser Leu Leu Arg Ile Thr Gly Val Thr Asp Lys Asp Phe Ser Leu Lys
    290                 295                 300

Tyr Asp Cys Val Ala Met Asn His His Gly Val Ile Arg His Pro Val
305                 310                 315                 320

Arg Leu Arg Arg Lys Gln Pro Ser Lys Glu Cys Leu Ser Gln Ile Ala
                325                 330                 335

<210> SEQ ID NO 7
<211> LENGTH: 2065
<212> TYPE: DNA
<213> ORGANISM: Rattus norvegicus
<220> FEATURE:
<221> NAME/KEY: CDS
<222> LOCATION: (275)..(1975)
<223> OTHER INFORMATION: Fit-1M

<400> SEQUENCE: 7
aggagaaaag actgggatat gctagcttgc tagctccagc aagcggcggt atgcgcggtc      60
tttaaaatag acagacatag aggctttggg ggagaggaag aagtgcctgg gatgaagaag     120
agatgcacct acccggcagg ggtgaaatcc caagctacac tgatttctct tttggaccct     180
acatcagaca gcacacatca accgcctagt ggactcaccg ttaccttcct gtgccattgc     240
catcggagag atctcggcca tcaatcacta gcac atg att ggc aaa tgg aga atg    295
                                    Met Ile Gly Lys Trp Arg Met
                                      1               5 ggg ctt tgg gct ttg gca att ctg aca gtt ccc atg tat ttc ata gtg     343
Gly Leu Trp Ala Leu Ala Ile Leu Thr Val Pro Met Tyr Phe Ile Val
         10                  15                  20 aca gag ggc aga aaa aca tcc tgg ggt cta gaa aac gag gct tta att     391
Thr Glu Gly Arg Lys Thr Ser Trp Gly Leu Glu Asn Glu Ala Leu Ile
 25                  30                  35 gtc aga tgc ccc caa aga gga ggt gcg att aac cct gtg gaa tgg tat     439
Val Arg Cys Pro Gln Arg Gly Gly Ala Ile Asn Pro Val Glu Trp Tyr
 40                  45                  50                  55 tat tca aat aca aat gaa aga att cct act caa aag aga aat cgg atc     487
Tyr Ser Asn Thr Asn Glu Arg Ile Pro Thr Gln Lys Arg Asn Arg Ile
                 60                  65                  70 ttc gtc tca aga gat cgt ctg aag ttt cta cca gcc aaa gtg gaa gac     535
```

-continued

```
                Phe Val Ser Arg Asp Arg Leu Lys Phe Leu Pro Ala Lys Val Glu Asp
                             75                  80                  85 tct ggg att tat acg tgt gtt atc aga agc cct gaa tcg att aag acc       583
Ser Gly Ile Tyr Thr Cys Val Ile Arg Ser Pro Glu Ser Ile Lys Thr
             90                  95                 100 gga tct ttg aat gtc acc ata tat aaa aga cca cca aac tgc aaa atc       631
Gly Ser Leu Asn Val Thr Ile Tyr Lys Arg Pro Pro Asn Cys Lys Ile
        105                 110                 115 cct gat tac atg atg tac tcg aca gta gat gga tca gat aaa aat tcc       679
Pro Asp Tyr Met Met Tyr Ser Thr Val Asp Gly Ser Asp Lys Asn Ser
120                 125                 130                 135 aag ata aca tgt cca aca att gcc ttg tat aat tgg aca gcg cct gtt       727
Lys Ile Thr Cys Pro Thr Ile Ala Leu Tyr Asn Trp Thr Ala Pro Val
                140                 145                 150 cag tgg ttt aag aac tgc aaa gct ctc caa ggg cca agg ttc agg gca       775
Gln Trp Phe Lys Asn Cys Lys Ala Leu Gln Gly Pro Arg Phe Arg Ala
            155                 160                 165 cac atg tcc tat ttg ttc att gac aaa gtg agt cat gtt gat gaa ggt       823
His Met Ser Tyr Leu Phe Ile Asp Lys Val Ser His Val Asp Glu Gly
        170                 175                 180 gac tac aca tgt cga ttc act cac acg gag aac gga acc aat tac att       871
Asp Tyr Thr Cys Arg Phe Thr His Thr Glu Asn Gly Thr Asn Tyr Ile
185                 190                 195 gtg act gcc acc aga tca ttc aca gtt gaa gaa aaa ggc ttc tct aca       919
Val Thr Ala Thr Arg Ser Phe Thr Val Glu Glu Lys Gly Phe Ser Thr
200                 205                 210                 215 ttt cca gta att aca aac cct cca cac aac tac aca gtg gaa gtg gaa       967
Phe Pro Val Ile Thr Asn Pro Pro His Asn Tyr Thr Val Glu Val Glu
                220                 225                 230 ata gga aaa aca gca aac att gcc tgc tca gct tgc ttt ggc aca gcc      1015
Ile Gly Lys Thr Ala Asn Ile Ala Cys Ser Ala Cys Phe Gly Thr Ala
            235                 240                 245 tct cag ttc gtt gct gtc ctg tgg cag att aac aaa acg aga att gga      1063
Ser Gln Phe Val Ala Val Leu Trp Gln Ile Asn Lys Thr Arg Ile Gly
        250                 255                 260 tct ttt ggc aaa gca aga att caa gaa gag aaa ggc cca aat aaa agt      1111
Ser Phe Gly Lys Ala Arg Ile Gln Glu Glu Lys Gly Pro Asn Lys Ser
265                 270                 275 tcc agc aat ggc atg att tgc tta acc tca ctg tta agg ata act ggt      1159
Ser Ser Asn Gly Met Ile Cys Leu Thr Ser Leu Leu Arg Ile Thr Gly
                280                 285                 290                 295 gtg acc gac aag gac ttc tcc ctg aaa tat gac tgt gtg gcc atg aac      1207
Val Thr Asp Lys Asp Phe Ser Leu Lys Tyr Asp Cys Val Ala Met Asn
            300                 305                 310 cat cac gga gtg ata agg cac ccc gta aga ctg aga agg aaa caa cca      1255
His His Gly Val Ile Arg His Pro Val Arg Leu Arg Arg Lys Gln Pro
        315                 320                 325 att gac cac caa agc acc tac tac ata gtt gcc gga tgt agt tta ttg      1303
Ile Asp His Gln Ser Thr Tyr Tyr Ile Val Ala Gly Cys Ser Leu Leu
330                 335                 340 cta atg ttt atc aat gtc ttg gtg ata gtc tta aaa gtg ttc tgg att      1351
Leu Met Phe Ile Asn Val Leu Val Ile Val Leu Lys Val Phe Trp Ile
                345                 350                 355 gag gtt gct ctg ttc tgg aga gat ata atg gca cct tac aaa acc cag      1399
Glu Val Ala Leu Phe Trp Arg Asp Ile Met Ala Pro Tyr Lys Thr Gln
            360                 365                 370                 375 aat gat gga aag ctc tat gat gct tac atc att tac cct cgg gtc ttc      1447
Asn Asp Gly Lys Leu Tyr Asp Ala Tyr Ile Ile Tyr Pro Arg Val Phe
        380                 385                 390 cgg ggc agc gca gca ggg acc ggc tct gtg gag tac ttt gtt cac tac      1495
```

```
Arg Gly Ser Ala Ala Gly Thr Gly Ser Val Glu Tyr Phe Val His Tyr
            395                 400                 405 act ctg ccc gac gtt ctc gaa aat aaa tgt ggc tac aag ttg tgc att      1543
Thr Leu Pro Asp Val Leu Glu Asn Lys Cys Gly Tyr Lys Leu Cys Ile
        410                 415                 420 tac ggg aga gac ctg ctg cct ggg caa gat gcg gcc act gtg gtg gaa      1591
Tyr Gly Arg Asp Leu Leu Pro Gly Gln Asp Ala Ala Thr Val Val Glu
    425                 430                 435 agc agt atc cag aat agt aga cgg caa gtg ttt gtc ctg gcc cct cac      1639
Ser Ser Ile Gln Asn Ser Arg Arg Gln Val Phe Val Leu Ala Pro His
440                 445                 450                 455 atg atg cac agc aaa gag ttt gcc tat gag cag gag atc gcc ctg cac      1687
Met Met His Ser Lys Glu Phe Ala Tyr Glu Gln Glu Ile Ala Leu His
            460                 465                 470 agc gcc ctc atc cag aac aac tcc aag gtg att ctg att gaa atg gag      1735
Ser Ala Leu Ile Gln Asn Asn Ser Lys Val Ile Leu Ile Glu Met Glu
        475                 480                 485 cct atg ggt gag gca agc cga ctg cag ctt ggg gat ctg caa gat tct      1783
Pro Met Gly Glu Ala Ser Arg Leu Gln Leu Gly Asp Leu Gln Asp Ser
    490                 495                 500 ctc cag cat ctt gtg aaa atg cag ggg acc atc aag tgg agg gaa gac      1831
Leu Gln His Leu Val Lys Met Gln Gly Thr Ile Lys Trp Arg Glu Asp
505                 510                 515 cac gtg gcc gac aaa cag tct cta agc tcc aaa ttc tgg aag cat gtg      1879
His Val Ala Asp Lys Gln Ser Leu Ser Ser Lys Phe Trp Lys His Val
520                 525                 530                 535 aga tac caa atg cca gtc ccg aaa aga ccc ccc aag atg gca tct gtt      1927
Arg Tyr Gln Met Pro Val Pro Lys Arg Pro Pro Lys Met Ala Ser Val
            540                 545                 550 gcc gct ccg ttg agt ggc aag gtg tgc ttg gac ctg aaa cac ttt tga      1975
Ala Ala Pro Leu Ser Gly Lys Val Cys Leu Asp Leu Lys His Phe
        555                 560                 565 gtcgtggact tgcctactca gagctgggga atcccagcag taggccccag aagtgaaggt    2035
gtgaagactt gaaatgccaa gggtggggcc                                     2065

<210> SEQ ID NO 8
<211> LENGTH: 566
<212> TYPE: PRT
<213> ORGANISM: Rattus norvegicus

<400> SEQUENCE: 8

Met Ile Gly Lys Trp Arg Met Gly Leu Trp Ala Leu Ala Ile Leu Thr
1               5                   10                  15

Val Pro Met Tyr Phe Ile Val Thr Glu Gly Arg Lys Thr Ser Trp Gly
            20                  25                  30

Leu Glu Asn Glu Ala Leu Ile Val Arg Cys Pro Gln Arg Gly Gly Ala
        35                  40                  45

Ile Asn Pro Val Glu Trp Tyr Tyr Ser Asn Thr Asn Glu Arg Ile Pro
    50                  55                  60

Thr Gln Lys Arg Asn Arg Ile Phe Val Ser Arg Asp Arg Leu Lys Phe
65                  70                  75                  80

Leu Pro Ala Lys Val Glu Asp Ser Gly Ile Tyr Thr Cys Val Ile Arg
                85                  90                  95

Ser Pro Glu Ser Ile Lys Thr Gly Ser Leu Asn Val Thr Ile Tyr Lys
            100                 105                 110

Arg Pro Pro Asn Cys Lys Ile Pro Asp Tyr Met Met Tyr Ser Thr Val
        115                 120                 125

Asp Gly Ser Asp Lys Asn Ser Lys Ile Thr Cys Pro Thr Ile Ala Leu
```

-continued

```
                130                 135                 140
Tyr Asn Trp Thr Ala Pro Val Gln Trp Phe Lys Asn Cys Lys Ala Leu
145                 150                 155                 160

Gln Gly Pro Arg Phe Arg Ala His Met Ser Tyr Leu Phe Ile Asp Lys
                165                 170                 175

Val Ser His Val Asp Glu Gly Asp Tyr Thr Cys Arg Phe Thr His Thr
            180                 185                 190

Glu Asn Gly Thr Asn Tyr Ile Val Thr Ala Thr Arg Ser Phe Thr Val
                195                 200                 205

Glu Glu Lys Gly Phe Ser Thr Phe Pro Val Ile Thr Asn Pro Pro His
    210                 215                 220

Asn Tyr Thr Val Glu Val Glu Ile Gly Lys Thr Ala Asn Ile Ala Cys
225                 230                 235                 240

Ser Ala Cys Phe Gly Thr Ala Ser Gln Phe Val Ala Val Leu Trp Gln
                245                 250                 255

Ile Asn Lys Thr Arg Ile Gly Ser Phe Gly Lys Ala Arg Ile Gln Glu
                260                 265                 270

Glu Lys Gly Pro Asn Lys Ser Ser Asn Gly Met Ile Cys Leu Thr
        275                 280                 285

Ser Leu Leu Arg Ile Thr Gly Val Thr Asp Lys Asp Phe Ser Leu Lys
        290                 295                 300

Tyr Asp Cys Val Ala Met Asn His His Gly Val Ile Arg His Pro Val
305                 310                 315                 320

Arg Leu Arg Arg Lys Gln Pro Ile Asp His Gln Ser Thr Tyr Tyr Ile
                325                 330                 335

Val Ala Gly Cys Ser Leu Leu Leu Met Phe Ile Asn Val Leu Val Ile
                340                 345                 350

Val Leu Lys Val Phe Trp Ile Glu Val Ala Leu Phe Trp Arg Asp Ile
            355                 360                 365

Met Ala Pro Tyr Lys Thr Gln Asn Asp Gly Lys Leu Tyr Asp Ala Tyr
    370                 375                 380

Ile Ile Tyr Pro Arg Val Phe Arg Gly Ser Ala Ala Gly Thr Gly Ser
385                 390                 395                 400

Val Glu Tyr Phe Val His Tyr Thr Leu Pro Asp Val Leu Glu Asn Lys
                405                 410                 415

Cys Gly Tyr Lys Leu Cys Ile Tyr Gly Arg Asp Leu Leu Pro Gly Gln
                420                 425                 430

Asp Ala Ala Thr Val Val Glu Ser Ser Ile Gln Asn Ser Arg Arg Gln
            435                 440                 445

Val Phe Val Leu Ala Pro His Met Met His Ser Lys Glu Phe Ala Tyr
        450                 455                 460

Glu Gln Glu Ile Ala Leu His Ser Ala Leu Ile Gln Asn Asn Ser Lys
465                 470                 475                 480

Val Ile Leu Ile Glu Met Glu Pro Met Gly Glu Ala Ser Arg Leu Gln
                485                 490                 495

Leu Gly Asp Leu Gln Asp Ser Leu Gln His Leu Val Lys Met Gln Gly
            500                 505                 510

Thr Ile Lys Trp Arg Glu Asp His Val Ala Asp Lys Gln Ser Leu Ser
        515                 520                 525
```

-continued

```
Ser Lys Phe Trp Lys His Val Arg Tyr Gln Met Pro Val Pro Lys Arg
    530             535             540

Pro Pro Lys Met Ala Ser Val Ala Ala Pro Leu Ser Gly Lys Val Cys
545             550                 555                 560

Leu Asp Leu Lys His Phe
                565
```

IL1RL-1 AS A CARDIOVASCULAR DISEASE MARKER AND THERAPEUTIC TARGET

RELATED APPLICATIONS

This application is a continuation of U.S. patent application Ser. No. 12/614,970, filed on Nov. 9, 2009, which is a continuation of U.S. patent application Ser. No. 10/435,482, filed on May 9, 2003, issued as U.S. Pat. No. 7,670,769, which claims the benefit under 35 U.S.C. §119 of U.S. provisional application 60/379,173, filed May 9, 2002, the contents of each of which are incorporated herein by reference in their entirety.

GOVERNMENT SUPPORT

The work resulting in this invention was supported in part by NIH Grant Nos. HL69484, HL63927, and HL052320. Accordingly, the U.S. Government has certain rights in this invention.

FIELD OF THE INVENTION

This invention relates to methods and compositions for the diagnosis and treatment of cardiovascular conditions. More specifically, the invention relates to isolated molecules that can be used to treat cardiovascular conditions including cardiac hypertrophy, myocardial infarction, stroke, arteriosclerosis, and heart failure.

BACKGROUND OF THE INVENTION

Despite significant advances in therapy, cardiovascular disease remains the single most common cause of morbidity and mortality in the developed world. Thus, prevention and therapy of cardiovascular conditions such as myocardial infarction and stroke is an area of major public health importance. Currently, several risk factors for future cardiovascular disorders have been described and are in wide clinical use in the detection of subjects at high risk. Such screening tests include evaluations of total and HDL cholesterol levels. However, a large number of cardiovascular disorders occur in subjects with apparently low to moderate risk profiles, and ability to identify such patients is limited. Moreover, accumulating data suggests that the beneficial effects of certain preventive and therapeutic treatments for patients at risk for or known to have cardiovascular disorders differs in magnitude among different patient groups. At this time, however, data describing diagnostic tests to determine whether certain therapies can be expected to be more or less effective are lacking.

SUMMARY OF THE INVENTION

This invention provides methods and compositions for the diagnosis and treatment of cardiovascular conditions. More specifically, a gene was identified that is upregulated in cardiac cells when the cells are subjected to mechanically-induced deformation. In view of these discoveries, it is believed that the molecules of the present invention can be used to treat cardiovascular (including vascular) conditions, including cardiac hypertrophy, myocardial infarction, stroke, arteriosclerosis, and heart failure.

Additionally, methods for using these molecules in the diagnosis of any of the foregoing cardiovascular (including vascular) conditions, are also provided.

Furthermore, compositions useful in the preparation of therapeutic preparations for the treatment of the foregoing conditions, are also provided.

The present invention thus involves, in several aspects, polypeptides, isolated nucleic acids encoding those polypeptides, functional modifications and variants of the foregoing, useful fragments of the foregoing, as well as therapeutics and diagnostics relating thereto.

According to one aspect of the invention, a method of diagnosing a condition characterized by aberrant expression of a nucleic acid molecule or an expression product thereof (or of unique fragments of the foregoing molecules thereof), is provided. The method involves contacting a biological sample from a subject with an agent, wherein said agent specifically binds to said nucleic acid molecule, an expression product thereof, or a fragment of an expression product thereof, and measuring the amount of bound agent and determining therefrom if the expression of said nucleic acid molecule or of an expression product thereof is aberrant, aberrant expression being diagnostic of the disorder, wherein the nucleic acid molecule is Interleukin 1 Receptor-Like 1 (IL1RL-1, also known as T1/ST2, ST2, and Fit-1, SEQ ID NOs: 1 and 2 for the soluble form and SEQ ID NOs: 3 and 4 for the membrane form). The terms IL1RL-1, T1/ST2, ST2, and Fit-1, are used interchangeably hereinafter throughout the specification. In some embodiments, the disorder is a cardiovascular condition selected from the group consisting of myocardial infarction, stroke, arteriosclerosis, and heart failure. In one embodiment, the disorder is cardiac hypertrophy. In another embodiment, the disorder is heart failure. In certain embodiments, biological samples include biopsy samples, and biological fluids such as blood/serum.

According to still another aspect of the invention, a method for determining a stage (e.g., regression, progression or onset) of a cardiovascular condition in a subject characterized by aberrant expression of a nucleic acid molecule or an expression product thereof (or of unique fragments of the foregoing molecules thereof), is provided. The method involves monitoring a sample from a patient for a parameter selected from the group consisting of (i) a IL1RL-1 nucleic acid molecule (or a unique fragment thereof), (ii) a polypeptide encoded by the IL1RL-1 nucleic acid, (iii) a peptide derived from the polypeptide (or of a unique fragment thereof), and (iv) an antibody which selectively binds the polypeptide or peptide (or a unique fragment thereof), as a determination of a stage (e.g., regression, progression or onset) of said cardiovascular condition in the subject. In some embodiments, the sample is a biological fluid or a tissue as described in any of the foregoing embodiments. In certain embodiments, the step of monitoring comprises contacting the sample with a detectable agent selected from the group consisting of (a) an isolated nucleic acid molecule which selectively hybridizes under stringent conditions to the nucleic acid molecule of (i), (b) an antibody which selectively binds the polypeptide of (ii), or the peptide of (iii), and (c) a polypeptide or peptide which selectively binds the antibody of (iv). The antibody, polypeptide, peptide, or nucleic acid can be labeled with a detectable label such as a radioactive label or an enzyme. In further embodiments, the method comprises monitoring (assaying) the sample for the peptide. In still further embodiments, monitoring the sample occurs over a period of time.

According to another aspect of the invention, a kit is provided. The kit comprises a package containing an agent that selectively binds to any of the foregoing IL1RL-1 isolated nucleic acids, or expression products thereof, and a control for comparing to a measured value of binding of said agent any of the foregoing isolated nucleic acids or expression products thereof. In some embodiments, the control is a predetermined value for comparing to the measured value. In certain embodiments, the control comprises an epitope of the expression product of any of the foregoing isolated nucleic acids.

According to one aspect of the invention, a method for treating a cardiovascular condition is provided. The method involves administering to a subject in need of such treatment a IL1RL-1 molecule, in an amount effective to treat the cardiovascular condition. In certain embodiments, the cardiovascular condition is selected from the group consisting of myocardial infarction, stroke, arteriosclerosis, and heart failure. In some embodiments, the method further comprises co-administering an agent selected from the group consisting of an anti-inflammatory agent, an anti-thrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, or an angiotensin system inhibitor.

According to another aspect of the invention, a method for treating cardiac hypertrophy is provided. The method involves administering to a subject in need of such treatment an agent that increases expression of a IL1RL-1 nucleic acid molecule, or an expression product thereof, in an amount effective to treat cardiac hypertrophy in the subject.

According to a further aspect of the invention, a method for treating a subject to reduce the risk of a cardiovascular condition developing in the subject is provided. The method involves administering to a subject that expresses aberrant levels of a IL1RL-1 molecule, an agent for reducing the risk of the cardiovascular disorder in an amount effective to lower the risk of the subject developing a future cardiovascular disorder, wherein the agent is an anti-inflammatory agent, an anti-thrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, or an angiotensin system inhibitor. In certain embodiments, the subject is otherwise free of symptoms calling for treatment with the agent.

According to one aspect of the invention, a method for identifying a candidate agent useful in the treatment of a cardiovascular condition is provided. The method involves determining expression of IL1RL-1 molecule in a cardiac cell or tissue under conditions which, in the absence of a candidate agent, permit a first amount of expression of the IL1RL-1 molecule, contacting the cardiac cell or tissue with the candidate agent, and detecting a test amount of expression of the IL1RL-1 molecule, wherein a decrease in the test amount of expression in the presence of the candidate agent relative to the first amount of expression indicates that the candidate agent is useful in the treatment of the cardiovascular condition. In important embodiments the IL1RL-1 molecule is any molecule of SEQ ID NO.:1-4. In certain embodiments, the cardiovascular condition is selected from the group consisting of cardiac hypertrophy (e.g., maladaptive hypertrophy), myocardial infarction, stroke, arteriosclerosis, and heart failure.

According to another aspect of the invention, a pharmaceutical composition is provided. The composition comprises an agent comprising an IL1RL-1 isolated nucleic acid molecule (SEQ ID NO.:1 or 3), or an expression product thereof (e.g., SEQ ID NO.:2 or 4), in a pharmaceutically effective amount to treat a cardiovascular condition, and a pharmaceutically acceptable carrier. In certain embodiments, the cardiovascular condition is selected from the group consisting of cardiac hypertrophy, myocardial infarction, stroke, arteriosclerosis, and heart failure.

According to a further aspect of the invention, methods for preparing medicaments useful in the treatment of a cardiovascular condition are also provided. The medicaments preferably contain an effective amount of at least one of the foregoing molecules or compositions.

According to still another aspect of the invention, a solid-phase nucleic acid molecule array is provided. The array consists essentially of a set of nucleic acid molecules, expression products thereof, or fragments (of either the nucleic acid or the polypeptide molecule) thereof, wherein at least a IL1RL-1 molecule (including expression products thereof, or fragments thereof), are fixed to a solid substrate. In some embodiments, the solid-phase array further comprises at least one control nucleic acid molecule.

In certain embodiments, the solid substrate includes a material selected from the group consisting of glass, silica, aluminosilicates, borosilicates, metal oxides such as alumina and nickel oxide, various clays, nitrocellulose, and nylon. Preferably the substrate is glass. In some embodiments, the nucleic acid molecules are fixed to the solid substrate by covalent bonding.

According to another aspect of the invention, a method for evaluating the likelihood that a subject will benefit from treatment with an agent for reducing the risk of a cardiovascular condition, is provided. In important embodiments the agent is selected from the group consisting of an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, and an angiotensin system inhibitor. The method involves obtaining a level of a IL1RL-1 molecule in the subject, and comparing the level of the IL1RL-1 molecule to a predetermined value specific for the diagnosis of a cardiovascular condition. The level of the IL1RL-1 molecule in comparison to the predetermined value is indicative of whether the subject will benefit from treatment with said agent. In certain embodiments, the predetermined value specific for the diagnosis of a cardiovascular condition is a plurality of predetermined marker level ranges and said comparing step comprises determining in which of said predetermined marker level ranges said subjects level falls. The cardiovascular condition can be a condition selected from the group consisting of cardiac hypertrophy, myocardial infarction, stroke, arteriosclerosis, and heart failure.

In another aspect of the invention a method for predicting outcome of a cardiovascular condition is provided. The method involves obtaining a level of a IL1RL-1 molecule in the subject, and comparing the level of the IL1RL-1 molecule to a predetermined value specific for the predicted outcome of a cardiovascular condition. The level of the IL1RL-1 molecule in comparison to the predetermined value is indicative of whether the subject will have a good/positive outcome or will have a bad/negative outcome. In some embodiments a high level of the IL1RL-1 molecule might indicate a negative outcome while a low level might indicate a positive outcome. In certain embodiments, the predetermined value specific for the predicted outcome of a cardiovascular condition is a plurality of predetermined marker level ranges and said comparing step comprises determining in which of said predetermined marker level ranges said subjects level falls. The cardiovascular condition can be a condition selected from the group consisting of cardiac hypertrophy, myocardial infarction, stroke, arteriosclerosis, and heart failure.

Any sequence of an IL1RL-1 molecule may be used in any of the aspects and embodiments of the invention. For instance, this includes the nucleotide sequences set forth as SEQ ID NOs.: 5 and 7, in addition to the nucleotide sequences set forth as SEQ ID NOs.: 1 and 3. This further includes the predicted amino acid sequences set forth as SEQ ID NOs.: 6 and 8, in addition to the predicted amino acid sequences set forth as SEQ ID NOs.: 2 and 4.

These and other objects of the invention will be described in further detail in connection with the detailed description of the invention.

BRIEF DESCRIPTION OF THE SEQUENCES

SEQ ID NO:1 is the nucleotide sequence of the human IL1RL1 (Soluble) cDNA.

SEQ ID NO:2 is the predicted amino acid sequence of the translation product of the human IL1RL1 (Soluble) cDNA (SEQ ID NO:1).

SEQ ID NO:3 is the nucleotide sequence of the human IL1RL1 (Membrane) cDNA.

SEQ ID NO:4 is the predicted amino acid sequence of the translation product of the human IL1RL1 (Membrane) (SEQ ID NO:3).

SEQ ID NO:5 is the nucleotide sequence of the rat Fit-1S cDNA.

SEQ ID NO:6 is the predicted amino acid sequence of the translation product of rat Fit-1S cDNA (SEQ ID NO:5).

SEQ ID NO:7 is the nucleotide sequence of the rat Fit-1M cDNA.

SEQ ID NO:8 is the predicted amino acid sequence of the translation product of the rat Fit-1M cDNA (SEQ ID NO:7).

DETAILED DESCRIPTION OF THE INVENTION

Figure 1:
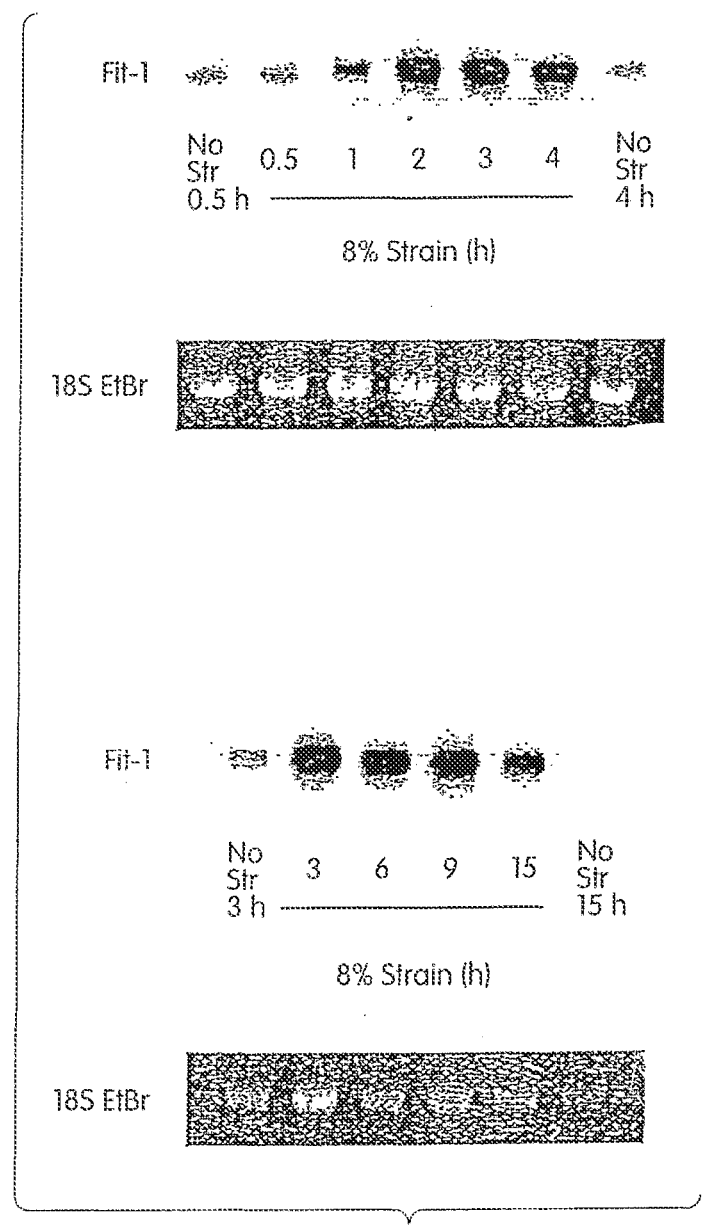
FIG. 1 depicts by a Northern Blot the effects of 8% cyclic mechanical strain on the expression of Fit-1 in cultured cardiac myocytes over the course of time.

The invention involves the discovery of a number of genes that are upregulated in cardiac cells when the cells are subjected to a mechanically-induced strain deformation. In view of this discovery, it is believed that the molecules of the present invention can be used to treat cardiovascular conditions including cardiac hypertrophy, myocardial infarction, stroke, arteriosclerosis, and/or heart failure.

Additionally, methods for using these molecules in the diagnosis of any of the foregoing cardiovascular conditions, are also provided.

Furthermore, compositions useful in the preparation of therapeutic preparations for the treatment of the foregoing conditions, are also provided.

"Upregulated," as used herein, refers to increased expression of a gene and/or its encoded polypeptide. "Increased expression" refers to increasing (i.e., to a detectable extent) replication, transcription, and/or translation of any of the nucleic acids of the invention (IL1RL-1, SEQ ID NOs.:1, 3), since upregulation of any of these processes results in concentration/amount increase of the polypeptide encoded by the gene (nucleic acid). Conversely, "downregulation," or "decreased expression" as used herein, refers to decreased expression of a gene and/or its encoded polypeptide. The upregulation or downregulation of gene expression can be directly determined by detecting an increase or decrease, respectively, in the level of mRNA for the gene, or the level of protein expression of the gene-encoded polypeptide, using any suitable means known to the art, such as nucleic acid hybridization or antibody detection methods, respectively, and in comparison to controls.

A "cardiac cell", as used herein, refers to a cardiomyocyte.

A "molecule," as used herein, embraces both "nucleic acids" and "polypeptides."

"Expression," as used herein, refers to nucleic acid and/or polypeptide expression.

As used herein, a "subject" is a mammal or a non-human mammal. In all embodiments human nucleic acids, polypeptides, and human subjects are preferred. It is believed that the results obtained using the human and rat molecules described elsewhere herein are predictive of the results that may be obtained using other homologous sequences.

In general, homologs and alleles typically will share at least 80% nucleotide identity and/or at least 85% amino acid identity to the characterized human sequences of the invention. In further instances, homologs and alleles typically will share at least 90%, 95%, or even 99% nucleotide identity and/or at least 95%, 98%, or even 99% amino acid identity to the characterized human sequences, respectively. The homology can be calculated using various, publicly available software tools developed by NCBI (Bethesda, Md.). Exemplary tools include the heuristic algorithm of Altschul S F, et al., (*J Mol Biol*, 1990, 215:403-410), also known as BLAST. Pairwise and ClustalW alignments (BLOSUM30 matrix setting) as well as Kyte-Doolittle hydropathic analysis can be obtained using public (EMBL, Heidelberg, Germany) and commercial (e.g., the MacVector sequence analysis software from Oxford Molecular Group/Genetics Computer Group, Madison, Wis., Accelrys, Inc., San Diego, Calif.). Watson-Crick complements of the foregoing nucleic acids also are embraced by the invention.

In screening for related genes, such as homologs and alleles of the sequences described elsewhere herein, a Southern blot may be performed using stringent conditions, together with a probe. The term "stringent conditions," as used herein, refers to parameters with which the art is familiar. With nucleic acids, hybridization conditions are said to be stringent typically under conditions of low ionic strength and a temperature just below the melting temperature ($T_m$) of the DNA hybrid complex (typically, about 3° C. below the $T_m$ of the hybrid). Higher stringency makes for a more specific correlation between the probe sequence and the target. Stringent conditions used in the hybridization of nucleic acids are well known in the art and may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. An example of "high stringency conditions" is hybridization at 65° C. in 6×SSC. Another example of high stringency conditions is hybridization at 65° C. in hybridization buffer that consists of 3.5×SSC, 0.02% Ficoll, 0.02% polyvinyl pyrolidone, 0.02% Bovine Serum Albumin, 2.5 mM $NaH_2PO_4$ [pH7], 0.5% SDS, 2 mM EDTA. (SSC is 0.015M sodium chloride/0.15M sodium citrate, pH7; SDS is sodium dodecyl sulphate; and EDTA is ethylenediaminetetracetic acid). After hybridization, the membrane upon which the DNA is transferred is washed at 2×SSC at room temperature and then at 0.1×SSC/0.1×SDS at temperatures up to 68° C. In a further example, an alternative to the use of an aqueous hybridization solution is the use of a formamide hybridization solution. Stringent hybridization conditions can thus be achieved using, for example, a 50% formamide solution and 42° C. There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of IL1RL-1 nucleic acids of the invention. The skilled artisan also is familiar with the methodology for screening cells and libraries for expression of such molecules which then are routinely isolated, followed by isolation of the pertinent nucleic acid molecule and sequencing.

Given the teachings herein of full-length human and rat cDNA clones, other mammalian sequences such as (mouse, bovine, etc.) cDNAs corresponding to the related human and rat nucleic acids can be isolated from cDNA libraries using standard colony hybridization techniques, or can be identified using a homology search, for example, in GenBank using any of the algorithms described elsewhere herein or known in the art. For example, sequences with GenBank Accession numbers Y07519.1 and D13695.1 for the mouse IL1RL-1 homologs, can be used interchangeably with the homologous rat sequences of the invention, in all aspects of the invention without departing from the essence of the invention.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulated by recombinant DNA techniques well known in the art. Thus, a nucleotide sequence contained in a vector in which 5' and 3' restriction sites are known or for which polymerase chain reaction (PCR) primer sequences have been disclosed is considered isolated, but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulated by standard techniques known to those of ordinary skill in the art.

According to the invention, expression of any of the foregoing IL1RL-1 nucleic acids of the present invention, including unique fragments of the foregoing, can be determined using different methodologies. A "unique fragment," as used herein, with respect to a nucleic acid is one that is a "signature" for the larger nucleic acid. For example, the unique fragment is long enough to assure that its precise sequence is not found in molecules within the human genome outside of the sequence for each nucleic acid defined above. Those of ordinary skill in the art may apply no more than routine procedures to determine if a fragment is unique within the human genome. Unique fragments, however, exclude fragments completely composed of nucleotide sequences previously published as of the filing date of this application.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for other uses such as PCR. Unique fragments also can be used to produce fusion proteins for generating antibodies, or determining binding of the polypeptide fragments, or for generating immunoassay components. Likewise, unique fragments can be employed to produce nonfused fragments of, for example, the IL1RL-1 polypeptides, useful, for example, in the preparation of antibodies, immunoassays or therapeutic applications. Unique fragments further can be used as antisense molecules to inhibit the expression of the foregoing nucleic acids and polypeptides respectively.

As will be recognized by those skilled in the art, the size of the unique fragment will depend upon its conservancy in the genetic code. Thus, some regions of SEQ ID NOs: 1, and 3, and complements will require longer segments to be unique while others will require only short segments, typically between 12 and 32 nucleotides long (e.g., 12, 13, 14, 15, 16, 17, 18, 19, 20, 21, 22, 23, 24, 25, 26, 27, 28, 29, 30, 31 and 32 bases) or more, up to the entire length of each of the disclosed sequences. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, (provided the sequence is unique as described above). For example, virtually any segment of the region of SEQ ID NO:1 beginning at nucleotide 1 and ending at nucleotide 1357, or SEQ ID NO:3 beginning at nucleotide 1 and ending at nucleotide 2058, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

In certain aspects, the invention embraces antisense oligonucleotides that selectively bind to a nucleic acid molecule encoding a polypeptide, to decrease the polypeptide's activity.

As used herein, the terms "antisense molecules," "antisense oligonucleotide," and "antisense" describe an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of an antisense oligonucleotide and its degree of complementarity with its target will depend upon the specific target selected, including the sequence of the target and the particular bases which comprise that sequence. It is preferred that an antisense oligonucleotide be constructed and arranged so as to bind selectively with a target under physiological conditions, i.e., to hybridize substantially more to the target sequence than to any other sequence in the target cell under physiological conditions. Based upon SEQ ID NOs: 1, and 3, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med*, 1995, 1(11):1116-1118; *Nat.* *Biotech.*, 1996, 14:840-844). Most preferably, the antisense oligonucleotides comprise a complementary sequence of 20-30 bases.

Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5): 439-457, 1994) and at which proteins are not expected to bind. Finally, although, SEQ ID NOs: 1 and 3, disclose cDNA sequences, one of ordinary skill in the art may easily derive the genomic DNA corresponding to the foregoing sequences. Thus, the present invention also provides for antisense oligonucleotides which are complementary to the genomic DNA corresponding to SEQ ID NOs: 1 and 3. Similarly, antisense to allelic or homologous human cDNAs and genomic DNAs are enabled without undue experimentation.

The oligonucleotides of the invention may include RNAi molecules. The use of RNA interference or "RNAi" involves the use of double-stranded RNA (dsRNA) to block gene expression. (see, e.g. Sui, G, et al, Proc Natl. Acad. Sci. U.S.A. 99:5515-5520, 2002). Methods of applying RNAi strategies in embodiments of the invention will be known to one of ordinary skill in the art.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose in place of ribose. The present invention, thus, contemplates pharmaceutical preparations containing modified antisense molecules that are complementary to and hybridizable with, under physiological conditions, nucleic acids encoding the polypeptides with SEQ ID NOs: 2, and/or 4, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves expression vectors coding for proteins encoded by the nucleic acids corresponding to SEQ ID NOs: 1 and/or 3, fragments and variants thereof, and host cells containing those expression vectors. Virtually any cell, prokaryotic or eukaryotic, which can be transformed with heterologous DNA or RNA and which can be grown or maintained in culture, may be used in the practice of the invention. Examples include bacterial cells such as *Escherichia coli* and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will often include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Still another preferred expression vector is an adenovirus, described by Stratford-Perricaudet, which is defective for E1 and E3 proteins (*J. Clin. Invest.* 90:626-630, 1992).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described SEQ ID NOs: 1 and/or 3, cDNA sequence-containing expression vectors, to transfect host cells and cell lines, be these prokaryotic (e.g., *Escherichia coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells.

The invention also provides isolated polypeptides (including whole proteins and partial proteins), encoded by the foregoing nucleic acids (SEQ ID NOs: 1 and 3), and include the polypeptides of SEQ ID NOs: 2 and/or 4, and unique fragments thereof. Such polypeptides are useful, for example, alone or as part of fusion proteins to generate antibodies, as components of an immunoassay, etc. Polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, (iii) for sequencing, (iv) as a therapeutic, etc.

A unique fragment for each of the foregoing polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of a polypeptide will require longer segments to be unique while others will require only short segments, typically between 5 and 12 amino acids (e.g. 5, 6, 7, 8, 9, 10, 11 and 12 amino acids long or more, including each integer up to the full length of each polypeptide).

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, interaction with other molecules, etc. One important activity is the ability to act as a signature for identifying the polypeptide. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the polypeptides described above. As used herein, a "variant" of a polypeptide is a polypeptide which contains one or more modifications to the primary amino acid sequence of a natural (e.g., "wild-type": a polypeptide with an amino acid sequence selected from the group consisting of SEQ ID NO: 2 and 4) polypeptide. Modifications which create a polypeptide variant are typically made to the nucleic acid which encodes the polypeptide, and can include deletions, point mutations, truncations, amino acid substitutions and addition of amino acids or non-amino acid moieties to: (1) reduce or eliminate an activity of a polypeptide; (2) enhance a property of a polypeptide, such as protein stability in an expression system or the stability of protein-ligand binding; (3) provide a novel activity or property to a polypeptide, such as addition of an antigenic epitope or addition of a detectable moiety; or (4) to provide equivalent or better binding to a polypeptide receptor or other molecule. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the polypeptide's amino acid sequence. One of skill in the art will be familiar with methods for predicting the effect on protein conformation of a change in protein sequence, and can thus "design" a variant polypeptide according to known methods. One example of such a method is described by Dahiyat and Mayo in *Science* 278:82-87, 1997, whereby proteins can be designed de novo. The method can be applied to a known protein to vary only a portion of the polypeptide sequence. By applying the computational methods of Dahiyat and Mayo, specific variants of any of the foregoing polypeptides can be proposed and tested to determine whether the variant retains a desired conformation.

Variants can include polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encodes a polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *Escherichia coli*, are well known to those of ordinary skill in the art. Still other mutations can be made to the noncoding sequences of a gene or cDNA clone to enhance expression of the polypeptide.

The skilled artisan will realize that conservative amino acid substitutions may be made in any of the foregoing polypeptides to provide functionally equivalent variants of the foregoing polypeptides, i.e., the variants retain the functional capabilities of each polypeptide. As used herein, a "conservative amino acid substitution" refers to an amino acid substitution which does not significantly alter the tertiary structure and/or activity of the polypeptide. Variants can be prepared according to methods for altering polypeptide sequence known to one of ordinary skill in the art, and include those that are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of polypeptides, i.e., variants of polypeptides which retain the function of the natural ("wild-type") polypeptides, are contemplated by the invention. Conservative amino acid substitutions in the amino acid sequence of polypeptides to produce functionally equivalent variants of each polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide. The activity of functionally equivalent fragments of polypeptides can be tested by cloning the gene encoding the altered polypeptide into a bacterial or mammalian expression vector, introducing the vector into an appropriate host cell, expressing the altered polypeptide, and testing for a functional capability of the polypeptides as disclosed herein The invention as described herein has a number of uses, some of which are described elsewhere herein. First, the invention permits isolation of polypeptides. A variety of methodologies well-known to the skilled artisan can be utilized to obtain isolated molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptides. Those skilled in the art also can readily follow known methods for isolating polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and use standard mutagenesis techniques to create one or more dominant negative variant polypeptides. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected activity and/or for retention of such an activity. Other similar methods for creating and testing dominant negative variants of a protein will be apparent to one of ordinary skill in the art.

The isolation of the cDNAs of the invention also makes it possible for the artisan to diagnose a disorder characterized by an aberrant expression of any of the foregoing cDNAs. These methods involve determining expression of each of the identified nucleic acids, and/or polypeptides derived therefrom. In the former situation, such determinations can be carried out via any standard nucleic acid determination assay, including the polymerase chain reaction, or assaying with labeled hybridization probes as exemplified below. In the latter situation, such determination can be carried out via any standard immunological assay using, for example, antibodies which bind to the secreted protein.

The invention also embraces isolated peptide binding agents which, for example, can be antibodies or fragments of antibodies ("binding polypeptides"), having the ability to selectively bind to any of the polypeptides of the invention (e.g., SEQ ID NO: 2 or 4). Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567; 5,225,539; 5,585,089; 5,693,762 and 5,859,205. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to polypeptides of the invention (e.g., SEQ ID NO: 2, or 4-its extracellular portions), and complexes of both the polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

The invention further provides efficient methods of identifying agents or lead compounds for agents active at the level of a polypeptide or polypeptide fragment dependent cellular function. In particular, such functions include interaction with other polypeptides or fragments. Generally, the screening methods involve assaying for compounds which interfere with the activity of a polypeptide of the invention, although compounds which enhance such activity also can be assayed using the screening methods. Such methods are adaptable to automated, high throughput screening of compounds. Target indications include cellular processes modulated by such polypeptides, for example, overexpression in cells under mechanical strains.

A wide variety of assays for candidate (pharmacological) agents are provided, including, labeled in vitro protein-ligand binding assays, electrophoretic mobility shift assays, immunoassays, cell-based assays such as two- or three-hybrid screens, expression assays, etc. The transfected nucleic acids can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding a polypeptide of the invention fused to a GAL4 DNA binding domain and a nucleic acid encoding a reporter gene operably joined to a gene expression regulatory region, such as one or more GAL4 binding sites. Activation of reporter gene transcription occurs when the reporter fusion polypeptide binds an agent such as to enable transcription of the reporter gene. Agents which modulate polypeptide mediated cell function are then detected through a change in the expression of reporter gene. Methods for determining changes in the expression of a reporter gene are known in the art.

Polypeptide fragments used in the methods, when not produced by a transfected nucleic acid are added to an assay mixture as an isolated polypeptide. Polypeptides preferably are produced recombinantly, although such polypeptides may be isolated from biological extracts. Recombinantly produced polypeptides include chimeric proteins comprising a fusion of a protein of the invention with another polypeptide, e.g., a polypeptide capable of providing or enhancing protein-protein binding, sequence specific nucleic acid binding (such as GAL4), enhancing stability of the polypeptide of the invention under assay conditions, or providing a detectable moiety, such as green fluorescent protein or a Flag epitope.

The assay mixture is comprised of a natural intracellular or extracellular binding target capable of interacting with a polypeptide of the invention. While natural polypeptide binding targets may be used, it is frequently preferred to use portions (e.g., peptides or nucleic acid fragments) or analogs (i.e., agents which mimic the polypeptide's binding properties of the natural binding target for purposes of the assay) of the polypeptide binding target so long as the portion or analog provides binding affinity and avidity to the polypeptide fragment measurable in the assay.

The assay mixture also comprises a candidate agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate agents are small organic compounds, i.e., those having a molecular weight of more than about 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be modified through conventional chemical, physical, and biochemical means. Further, known (pharmacological) agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The mixture of the foregoing assay materials is incubated under conditions whereby, but for the presence of the candidate agent, the chosen polypeptide of the invention specifically binds a cellular binding target, a portion thereof or analog thereof. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the polypeptide and one or more binding targets is detected by any convenient method available to the user. For cell free binding type assays, a separation step is often used to separate bound from unbound components. The separation step may be accomplished in a variety of ways.

Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, a non-specific protein, etc. When the solid substrate is a magnetic bead(s), the bead(s) may be washed one or more times with a washing solution and isolated using a magnet.

Detection may be effected in any convenient way for cell-based assays such as two- or three-hybrid screens. The transcript resulting from a reporter gene transcription assay of a polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc), or indirect detection (e.g., epitope tag such as the FLAG epitope, enzyme tag such as horseseradish peroxidase, etc.). The label may be bound to a binding partner of the polypeptide, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The invention provides polypeptide-specific binding agents, methods of identifying and making such agents, and their use in diagnosis, therapy and pharmaceutical development. For example, polypeptide-specific pharmacological agents are useful in a variety of diagnostic and therapeutic applications, especially where disease or disease prognosis is associated with altered polypeptide binding characteristics. Novel polypeptide-specific binding agents include polypeptide-specific antibodies, cell surface receptors, and other natural intracellular and extracellular binding agents identified with assays such as two hybrid screens, and non-natural intracellular and extracellular binding agents identified in screens of chemical libraries and the like.

In general, the specificity of polypeptide binding to a specific molecule is determined by binding equilibrium constants. Targets which are capable of selectively binding a polypeptide preferably have binding equilibrium constants of at least about $10^7 M^{-1}$, more preferably at least about $10^8 M^{-1}$, and most preferably at least about $10^9 M^{-1}$. A wide variety of cell based and cell free assays may be used to demonstrate polypeptide-specific binding. Cell based assays include one, two and three hybrid screens, assays in which polypeptide-mediated transcription is inhibited or increased, etc. Cell free assays include protein binding assays, immunoassays, etc. Other assays useful for screening agents which bind polypeptides of the invention include fluorescence resonance energy transfer (FRET), and electrophoretic mobility shift analysis (EMSA).

According to still another aspect of the invention, a method of diagnosing a disorder characterized by aberrant expression of a nucleic acid molecule, an expression product thereof, or a fragment of an expression product thereof, is provided. The method involves contacting a biological sample isolated from a subject with an agent that specifically binds to the nucleic acid molecule, an expression product thereof, or a fragment of an expression product thereof, and determining the interaction between the agent and the nucleic acid molecule or the expression product as a determination of the disorder, wherein the nucleic acid molecule is a IL1RL-1 nucleic acid (SEQ ID NO.:1). In some embodiments, the disorder is a cardiovascular condition selected from the group consisting of myocardial infarction, stroke, arteriosclerosis, and heart failure. In one embodiment, the disorder is cardiac hypertrophy. In another embodiment, the disorder is myocardial infarction. In one embodiment, the disorder is heart failure.

In the case where the molecule is a nucleic acid molecule, such determinations can be carried out via any standard nucleic acid determination assay, including the polymerase chain reaction, or assaying with labeled hybridization probes as exemplified herein. In the case where the molecule is an expression product of the nucleic acid molecule, or a fragment of an expression product of the nucleic acid molecule, such determination can be carried out via any standard immunological assay using, for example, antibodies which bind to any of the polypeptide expression products.

"Aberrant expression" refers to decreased expression (underexpression) or increased expression (overexpression) of any of the foregoing IL1RL-1 molecules (nucleic acids and/or polypeptides) in comparison with a control (i.e., expression of the same molecule in a healthy or "normal" subject). A "healthy subject," as used herein, refers to a subject who is not at risk for developing a future cardiovascular condition (see earlier discussion and Harrison's Principles of Experimental Medicine, 13th Edition, McGraw-Hill, Inc., N.Y.—hereinafter "Harrison's"). Healthy subjects also do not otherwise exhibit symptoms of disease. In other words, such subjects, if examined by a medical professional, would be characterized as healthy and free of symptoms of a cardiovascular disorder or at risk of developing a cardiovascular disorder.

When the disorder is a cardiovascular condition selected from the group consisting of cardiac hypertrophy, myocardial infarction, stroke, arteriosclerosis, and heart failure, decreased expression of any of the foregoing molecules in comparison with a control (e.g., a healthy subject) is indicative of the presence of the disorder, or indicative of the risk for developing such disorder in the future.

The invention also provides novel kits which could be used to measure the levels of the nucleic acids of the invention, or expression products of the invention.

In one embodiment, a kit comprises a package containing an agent that selectively binds to an isolated IL1RL-1 nucleic acid, or expression product thereof, and a control for comparing to a measured value of binding of said agent any of the foregoing isolated nucleic acids or expression products thereof. Kits are generally comprised of the following major elements: packaging, an agent of the invention, a control agent, and instructions. Packaging may be a box-like structure for holding a vial (or number of vials) containing an agent of the invention, a vial (or number of vials) containing a control agent, and instructions. Individuals skilled in the art can readily modify the packaging to suit individual needs. In some embodiments, the control is a predetermined value for comparing to the measured value. In certain embodiments, the control comprises an epitope of the expression product of any of the foregoing isolated nucleic acids.

Figure 7:
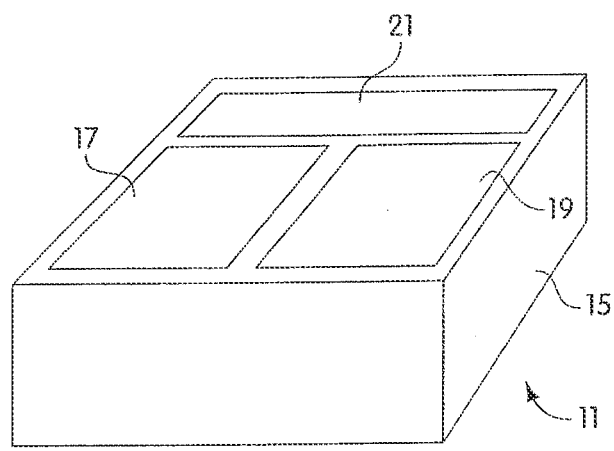
FIG. 7 depicts a kit embodying features of the present invention.

In the case of nucleic acid detection, pairs of primers for amplifying a nucleic acid molecule of the invention can be included. The preferred kits would include known amounts of nucleic acid probes, epitopes (such as IL1RL-1 expression products) or anti-epitope antibodies, as well as instructions or other printed material. In certain embodiments the printed material can characterize risk of developing a cardiovascular condition based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with any of the foregoing proteins of the invention and a container containing labeled anti-human IgG antibodies. A well of the plate is contacted with, for example, a biological fluid, washed and then contacted with the anti-IgG antibody. The label is then detected. A kit embodying features of the present invention, generally designated by the numeral 11, is illustrated in FIG. 7. Kit 11 is comprised of the following major elements: packaging 15, an agent of the invention 17, a control agent 19, and instructions 21. Packaging 15 is a box-like structure for holding a vial (or number of vials) containing an agent of the invention 17, a vial (or number of vials) containing a control agent 19, and instructions 21. Individuals skilled in the art can readily modify packaging 15 to suit individual needs.

In preferred embodiments the invention provides novel kits or assays which are specific for, and have appropriate sensitivity with respect to, predetermined values selected on the basis of the present invention. The preferred kits, therefore, would differ from those presently commercially available, by including, for example, different cut-offs, different sensitivities at particular cut-offs as well as instructions or other printed material for characterizing risk based upon the outcome of the assay.

The invention also embraces methods for evaluating the likelihood that a subject will benefit from treatment with an agent for reducing the risk of a cardiovascular condition. In some embodiments the agent is selected from the group consisting of an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, and an angiotensin system inhibitor. The method involves obtaining a level of a IL1RL-1 molecule in the subject, and comparing the level of the IL1RL-1 molecule to a predetermined value specific for the diagnosis of a cardiovascular condition. The level of the IL1RL-1 molecule in comparison to the predetermined value is indicative of whether the subject will benefit from treatment with said agent. In certain embodiments, the predetermined value specific for the diagnosis of a cardiovascular condition is a plurality of predetermined marker level ranges and said comparing step comprises determining in which of said predetermined marker level ranges said subjects level falls. The cardiovascular condition can be a condition selected from the group consisting of cardiac hypertrophy, myocardial infarction, stroke, arteriosclerosis, and heart failure.

The predetermined value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quadrants, the lowest quadrant being subjects with the lowest risk and the highest quadrant being subjects with the highest risk.

The predetermined value can depend upon the particular population selected. For example, an apparently healthy population (no detectable disease and no prior history of a cardiovascular disorder) will have a different 'normal' range of markers of systemic inflammation than will a smoking population or a population the members of which have had a prior cardiovascular disorder. Accordingly, the predetermined values selected may take into account the category in which the subject falls. Appropriate ranges and categories can be selected with no more than routine experimentation by those of ordinary skill in the art.

As discussed above the invention provides methods for evaluating the likelihood that a subject will benefit from treatment with an agent for reducing risk of a future cardiovascular disorder. This method has important implications for patient treatment and also for clinical development of new therapeutics. Physicians select therapeutic regimens for patient treatment based upon the expected net benefit to the patient. The net benefit is derived from the risk to benefit ratio. The present invention permits selection of subjects who are more likely to benefit by intervention, thereby aiding the physician in selecting a therapeutic regimen. This might include using drugs with a higher risk profile where the likelihood of expected benefit has increased. Likewise, clinical investigators desire to select for clinical trials a population with a high likelihood of obtaining a net benefit. The present invention can help clinical investigators select such subjects. It is expected that clinical investigators now will use the present invention for determining entry criteria for clinical trials.

The invention also embraces methods for treating a cardiovascular condition. In some embodiments, the method involves administering to a subject in need of such treatment a IL1RL-1 molecule, in an amount effective to treat the cardiovascular condition. In certain embodiments, the method involves administering to a subject in need of such treatment an agent that modulate the expression of any of the foregoing Il1Rl-1 molecules. "Agents that modulates expression" include any of the IL1RL-1 molecules described herein, agents that increase expression of these molecules, as well as agents that decrease expression of any of the foregoing IL1RL-1 molecules, in an amount effective to treat the cardiovascular condition.

"Agents that decrease expression" of a nucleic acid or a polypeptide, as used herein, are known in the art, and refer to antisense nucleic acids, antibodies that bind polypeptides encoded by the nucleic acids, and other agents that lower expression of such molecules. Any agents that decrease expression of a molecule (and as described herein, decrease its activity), are useful according to the invention.

In certain embodiments, the molecule is a nucleic acid (antisense). In some embodiments the nucleic acid is operatively coupled to a gene expression sequence which directs the expression of the nucleic acid molecule within a cardiomyocyte. The "gene expression sequence" is any regulatory nucleotide sequence, such as a promoter sequence or promoter-enhancer combination, which facilitates the efficient transcription and translation of the nucleic acid to which it is operably joined. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, α-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are activated in the presence of an inducing agent. For example, the metallothionein promoter is activated to increase transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined nucleic acid. The gene expression sequences optionally includes enhancer sequences or upstream activator sequences as desired.

Preferably, any of the IL1RL-1 nucleic acid molecules of the invention is linked to a gene expression sequence which permits expression of the nucleic acid molecule in a cell such as a cardiomyocyte and/or a vascular endothelial cell (including a smooth muscle cell). More preferably, the gene expression sequence permits expression of the nucleic acid molecule in a cardiomyocyte, and does not permit expression of the molecule in a cell selected from the group consisting of a neuronal cell, a fibroblast, and a cell of hematopoietic origin. A sequence which permits expression of the nucleic acid molecule in a cardiomyocyte, is one which is selectively active in such a cell type, thereby causing expression of the nucleic acid molecule in the cell. The cardiac myosin heavy chain gene promoter, for example, can be used to express any of the foregoing nucleic acid molecules of the invention in a cardiomyocyte. Those of ordinary skill in the art will be able to easily identify alternative promoters that are capable of expressing a nucleic acid molecule in a cardiomyocyte.

The nucleic acid sequence and the gene expression sequence are said to be "operably joined" when they are covalently linked in such a way as to place the transcription and/or translation of the nucleic acid coding sequence under the influence or control of the gene expression sequence. If it is desired that the nucleic acid sequence be translated into a functional protein, two DNA sequences are said to be operably joined if induction of a promoter in the 5' gene expression sequence results in the transcription of the nucleic acid sequence and if the nature of the linkage between the two DNA sequences does not (1) result in the introduction of a frame-shift mutation, (2) interfere with the ability of the promoter region to direct the transcription of the nucleic acid sequence, and/or (3) interfere with the ability of the corresponding RNA transcript to be translated into a protein. Thus, a gene expression sequence would be operably linked to a nucleic acid sequence if the gene expression sequence were capable of effecting transcription of that nucleic acid sequence such that the resulting transcript might be translated into the desired protein or polypeptide.

The molecules of the invention can be delivered to the preferred cell types of the invention alone or in association with a vector. In its broadest sense, a "vector" is any vehicle capable of facilitating: (1) delivery of a molecule to a target cell and/or (2) uptake of the molecule by a target cell. Preferably, the vectors transport the molecule into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing a nucleic acid or a protein) can be selectively delivered to a cardiomyocyte cell in, e.g., the myocardium. Methodologies for targeting include conjugates, such as those described in U.S. Pat. No. 5,391,723 to Priest. Another example of a well-known targeting vehicle is a liposome. Liposomes are commercially available from Gibco BRL (Life Technologies Inc., Rockville, Md.). Numerous methods are published for making targeted liposomes. Preferably, the molecules of the invention are targeted for delivery to cardiomyocytes, and/or vascular endothelial cells.

In general, the vectors useful in the invention include, but are not limited to, plasmids, phagemids, viruses, other vehicles derived from viral or bacterial sources that have been manipulated by the insertion or incorporation of the nucleic acid sequences of the invention, and additional nucleic acid fragments (e.g., enhancers, promoters) which can be attached to the nucleic acid sequences of the invention. Viral vectors are a preferred type of vector and include, but are not limited to, nucleic acid sequences from the following viruses: adenovirus; adeno-associated virus; retrovirus, such as Moloney murine leukemia virus; Harvey murine sarcoma virus; murine mammary tumor virus; rouse sarcoma virus; SV40-type viruses; polyoma viruses; Epstein-Barr viruses; papilloma viruses; herpes virus; vaccinia virus; polio virus; and RNA viruses such as a retrovirus. One can readily employ other vectors not named but known in the art.

A particularly preferred virus for certain applications is the adeno-associated virus, a double-stranded DNA virus. The adeno-associated virus is capable of infecting a wide range of cell types and species and can be engineered to be replication-deficient i.e., capable of directing synthesis of the desired proteins, but incapable of manufacturing an infectious particle. It further has advantages, such as heat and lipid solvent stability, high transduction frequencies in cells of diverse lineages, including hematopoietic cells, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient. Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Cliffton, N.J. (1991).

Another preferred retroviral vector is the vector derived from the Moloney murine leukemia virus, as described in Nabel, E. G., et al., *Science,* 1990, 249:1285-1288. These vectors reportedly were effective for the delivery of genes to all three layers of the arterial wall, including the media. Other preferred vectors are disclosed in Flugelman, et al., *Circulation,* 1992, 85:1110-1117. Additional vectors that are useful for delivering molecules of the invention are described in U.S. Pat. No. 5,674,722 by Mulligan, et al.

In addition to the foregoing vectors, other delivery methods may be used to deliver a molecule of the invention to a cell such as a cardiomyocyte and/or a vascular endothelial cell, and facilitate uptake thereby.

A preferred such delivery method of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µm can encapsulate large macromolecules. RNA, DNA, and intact virions can be encapsulated within the aqueous interior and be delivered to cells in a biologically active form (Fraley, et al., *Trends Biochem. Sci.,* 1981, 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, such as the myocardium or the vascular cell wall, by coupling the liposome to a specific ligand such as a monoclonal antibody, sugar, glycolipid, or protein. Ligands which may be useful for targeting a liposome to the vascular wall include, but are not limited to, the viral coat protein of the Hemagglutinating virus of Japan. Additionally, the vector may be coupled to a nuclear targeting peptide, which will direct the nucleic acid to the nucleus of the host cell.

Liposomes are commercially available from Gibco BRL, for example, as LIPOFECTIN™ and LIPOFECTACE™, which are formed of cationic lipids such as N-[1-(2,3-dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology,* V. 3, p. 235-241 (1985). Novel liposomes for the intracellular delivery of macromolecules, including nucleic acids, are also described in PCT International application no. PCT/US96/07572 (Publication No. WO 96/40060, entitled "Intracellular Delivery of Macromolecules").

In one particular embodiment, the preferred vehicle is a biocompatible micro particle or implant that is suitable for implantation into the mammalian recipient. Exemplary bioerodible implants that are useful in accordance with this method are described in PCT International application no. PCT/US95/03307 (Publication No. WO 95/24929, entitled "Polymeric Gene Delivery System", which claims priority to U.S. Pat. application No. 213,668, filed Mar. 15, 1994). PCT/US95/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the nucleic acids described herein are encapsulated or dispersed within the biocompatible, preferably biodegradable polymeric matrix disclosed in PCT/US95/03307. The polymeric matrix preferably is in the form of a micro particle such as a micro sphere (wherein a nucleic acid is dispersed throughout a solid polymeric matrix) or a microcapsule (wherein a nucleic acid is stored in the core of a polymeric shell). Other forms of the polymeric matrix for containing the nucleic acids of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular surface. The matrix composition also can be selected not to degrade, but rather, to release by diffusion over an extended period of time.

Both non-biodegradable and biodegradable polymeric matrices can be used to deliver the nucleic acids of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is crosslinked with multi-valent ions or other polymers.

In general, the nucleic acids of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and co-polymers thereof, alkyl cellulose, hydroxyalkyl celluloses, cellulose ethers, cellulose esters, nitrocelluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methylmethacrylate), poly(ethylmethacrylate), poly(butylmethacrylate), poly(isobutylmethacrylate), poly(hexylmethacrylate), poly(isodecylmethacrylate), poly(laurylmethacrylate), poly(phenylmethacrylate), poly(methylacrylate), poly(isopropylacrylate), poly(isobutylacrylate), poly(octadecylacrylate), polyethylene, polypropylene, poly(ethyleneglycol), poly(ethyleneoxide), poly(ethyleneterephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described is by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Thus, the invention provides a composition of the above-described molecules of the invention for use as a medicament, methods for preparing the medicament and methods for the sustained release of the medicament in vivo.

Compaction agents also can be used in combination with a vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, e.g., to deliver an isolated nucleic acid of the invention in a form that is more efficiently taken up by the cell or, more preferably, in combination with one or more of the above-described vectors.

Other exemplary compositions that can be used to facilitate uptake by a target cell of the nucleic acids of the invention include calcium phosphate and other chemical mediators of intracellular transport, microinjection compositions, electroporation and homologous recombination compositions (e.g., for integrating a nucleic acid into a preselected location within the target cell chromosome).

The term "facilitate uptake" of a molecule into a cell according to the invention has the following meanings depending upon the nature of the molecule. For an isolated nucleic acid it is meant to describe entry of the nucleic acid through the cell membrane and into the cell nucleus, where upon the "nucleic acid transgene" can utilize the cell machinery to produce functional polypeptides encoded by the nucleic acid. By "nucleic acid transgene" it is meant to describe all of the nucleic acids of the invention with or without the associated vectors. For a polypeptide, it is meant to describe entry of the polypeptide through the cell membrane and into the cell cytoplasm, and if necessary, utilization of the cell cytoplasmic machinery to functionally modify the polypeptide (e.g., to an active form).

Various techniques may be employed for introducing nucleic acids of the invention into cells, depending on whether the nucleic acids are introduced in vitro or in vivo in a host. Such techniques include transfection of nucleic acid-CaPO$_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a liposome, a retrovirus, or other virus) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

The invention also provides methods for the diagnosis and therapy of vascular and cardiovascular disorders. Such disorders include myocardial infarction, stroke, arteriosclerosis, heart failure, and cardiac hypertrophy.

The methods of the invention are useful in both the acute and the prophylactic treatment of any of the foregoing conditions. As used herein, an acute treatment refers to the treatment of subjects having a particular condition. Prophylactic treatment refers to the treatment of subjects at risk of having the condition, but not presently having or experiencing the symptoms of the condition.

In its broadest sense, the terms "treatment" or "to treat" refer to both acute and prophylactic treatments. If the subject in need of treatment is experiencing a condition (or has or is having a particular condition), then treating the condition refers to ameliorating, reducing or eliminating the condition or one or more symptoms arising from the condition. In some preferred embodiments, treating the condition refers to ameliorating, reducing or eliminating a specific symptom or a specific subset of symptoms associated with the condition. If the subject in need of treatment is one who is at risk of having a condition, then treating the subject refers to reducing the risk of the subject having the condition.

Stroke (also referred to herein as ischemic stroke and/or cerebrovascular ischemia) is often cited as the third most common cause of death in the industrial world, ranking behind ischemic heart disease and cancer. Strokes are responsible for about 300,000 deaths annually in the United States and are a leading cause of hospital admissions and long-term disabilities. Accordingly, the socioeconomic impact of stroke and its attendant burden on society is practically immeasurable.

"Stroke" is defined by the World Health Organization as a rapidly developing clinical sign of focal or global disturbance of cerebral function with symptoms lasting at least 24 hours. Strokes are also implicated in deaths where there is no apparent cause other than an effect of vascular origin.

Strokes are typically caused by blockages or occlusions of the blood vessels to the brain or within the brain. With complete occlusion, arrest of cerebral circulation causes cessation of neuronal electrical activity within seconds. Within a few minutes after the deterioration of the energy state and ion homeostasis, depletion of high energy phosphates, membrane ion pump failure, efflux of cellular potassium, influx of sodium chloride and water, and membrane depolarization occur. If the occlusion persists for more than five to ten minutes, irreversible damage results. With incomplete ischemia, however, the outcome is difficult to evaluate and depends largely on residual perfusion and the availability of oxygen. After a thrombotic occlusion of a cerebral vessel, ischemia is rarely total. Some residual perfusion usually persists in the ischemic area, depending on collateral blood flow and local perfusion pressure.

Cerebral blood flow can compensate for drops in mean arterial blood pressure from 90 to 60 mm Hg by autoregulation. This phenomenon involves dilatation of downstream resistant vessels. Below the lower level of autoregulation (about 60 mm Hg), vasodilatation is inadequate and the cerebral blood flow falls. The brain, however, has perfusion reserves that can compensate for the fall in cerebral blood flow. This reserve exists because under normal conditions only about 35% of the oxygen delivered by the blood is extracted. Therefore, increased oxygen extraction can take place, provided that normoxia and normocapnea exist. When distal blood pressure falls below approximately 30 mm Hg, the two compensatory mechanisms (autoregulation and perfusion reserve) are inadequate to prevent failure of oxygen delivery.

As blood flow drops below the ischemic threshold of 23 ml/100 g/minute, symptoms of tissue hypoxia develop. Severe ischemia may be lethal. When the ischemia is moderate, it will result in "penumbra." In the neurological context, penumbra refers to a zone of brain tissue with moderate ischemia and paralyzed neuronal function, which is reversible with restoration of adequate perfusion. The penumbra forms a zone of collaterally perfused tissue surrounding a core of severe ischemia in which an infarct has developed. In other words, the penumbra is the tissue area that can be saved, and is essentially in a state between life and death.

Although an ischemic event can occur anywhere in the vascular system, the carotid artery bifurcation and the origin of the internal carotid artery are the most frequent sites for thrombotic occlusions of cerebral blood vessels, which result in cerebral ischemia. The symptoms of reduced blood flow due to stenosis or thrombosis are similar to those caused by middle cerebral artery disease. Flow through the ophthalmic artery is often affected sufficiently to produce amaurosis fugax or transient monocular blindness. Severe bilateral internal carotid artery stenosis may result in cerebral hemispheric hypoperfusion. This manifests with acute headache ipsilateral to the acutely ischemic hemisphere. Occlusions or decrease of the blood flow with resulting ischemia of one anterior cerebral artery distal to the anterior communicating artery produces motor and cortical sensory symptoms in the contralateral leg and, less often, proximal arm. Other manifestations of occlusions or underperfusion of the anterior cerebral artery include gait ataxia and sometimes urinary incontinence due to damage to the parasagital frontal lobe. Language disturbances manifested as decreased spontaneous speech may accompany generalized depression of psychomotor activity.

Most ischemic strokes involve portions or all of the territory of the middle cerebral artery with emboli from the heart or extracranial carotid arteries accounting for most cases. Emboli may occlude the main stem of the middle cerebral artery, but more frequently produce distal occlusion of either the superior or the inferior branch. Occlusions of the superior branch cause weakness and sensory loss that are greatest in the face and arm. Occlusions of the posterior cerebral artery distal to its penetrating branches cause complete contralateral loss of vision. Difficulty in reading (dyslexia) and in performing calculations (dyscalculia) may follow ischemia of the dominant posterior cerebral artery. Proximal occlusion of the posterior cerebral artery causes ischemia of the branches penetrating to calamic and limbic structures. The clinical results are hemisensory disturbances that may chronically change to intractable pain of the defective side (thalamic pain).

A subject having a stroke is so diagnosed by symptoms experienced and/or by a physical examination including interventional and non-interventional diagnostic tools such as CT and MR imaging. The methods of the invention are advantageous for the treatment of various clinical presentations of stroke subjects. A subject having a stroke may present with one or more of the following symptoms: paralysis, weakness, decreased sensation and/or vision, numbness, tingling, aphasia (e.g., inability to speak or slurred speech, difficulty reading or writing), agnosia (i.e., inability to recognize or identify sensory stimuli), loss of memory, co-ordination difficulties, lethargy, sleepiness or unconsciousness, lack of bladder or bowel control and cognitive decline (e.g., dementia, limited attention span, inability to concentrate). Using medical imaging techniques, it may be possible to identify a subject having a stroke as one having an infarct or one having hemorrhage in the brain.

An important embodiment of the invention is treatment of a subject with an abnormally elevated risk of an ischemic stroke. As used herein, subjects having an abnormally elevated risk of an ischemic stroke are a category determined according to conventional medical practice (see earlier discussion); such subjects may also be identified in conventional medical practice as having known risk factors for stroke or having increased risk of cerebrovascular events. This category includes, for example, subjects which are having elective vascular surgery. Typically, the risk factors associated with cardiac disease are the same as are associated with stroke. The primary risk factors include hypertension, hypercholesterolemia, and smoking. Atrial fibrillation or recent myocardial infarction are also important risk factors. In addition, modified levels of expression of a IL1RL-1 nucleic acid molecule, or an expression product thereof, are also, according to the present invention, important risk factors.

As used herein, subjects having an abnormally elevated risk of an ischemic stroke also include subjects undergoing surgical or diagnostic procedures which risk release of emboli, lowering of blood pressure or decrease in blood flow to the brain, such as carotid endarterectomy, brain angiography, neurosurgical procedures in which blood vessels are compressed or occluded, cardiac catheterization, angioplasty, including balloon angioplasty, coronary by-pass surgery, or similar procedures. Subjects having an abnormally elevated risk of an ischemic stroke also include subjects having any cardiac condition that may lead to decreased blood flow to the brain, such as atrial fibrillation, ventrical tachycardia, dilated cardiomyopathy and other cardiac conditions requiring anticoagulation. Subjects having an abnormally elevated risk of an ischemic stroke also include subjects having conditions including arteriopathy or brain vasculitis, such as that caused by lupus, congenital diseases of blood vessels, such as CADASIL syndrome, or migraine, especially prolonged episodes.

The treatment of stroke can be for patients who have experienced a stroke or can be a prophylactic treatment. Short term prophylactic treatment is indicated for subjects having surgical or diagnostic procedures which risk release of emboli, lowering of blood pressure or decrease in blood flow to the brain, to reduce the injury due to any ischemic event that occurs as a consequence of the procedure. Longer term or chronic prophylactic treatment is indicated for subjects having cardiac conditions that may lead to decreased blood flow to the brain, or conditions directly affecting brain vasculature. If prophylactic, then the treatment is for subjects having an abnormally elevated risk of an ischemic stroke, as described above. If the subject has experienced a stroke, then the treatment can include acute treatment. Acute treatment for stroke subjects means administration of an agent of the invention at the onset of symptoms of the condition or within 48 hours of the onset, preferably within 24 hours, more preferably within 12 hours, more preferably within 6 hours, and even more preferably within 3 hours of the onset of symptoms of the condition.

Criteria for defining hypercholesterolemic and/or hypertriglyceridemic subjects are well known in the art (see, e.g., "Harrison's"). Hypercholesterolemic subjects and hypertriglyceridemic subjects are associated with increased incidence of premature coronary heart disease. A hypercholesterolemic subject has an LDL level of >160 mg/dL or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject has a triglyceride (TG) level of >250 mg/dL. Thus, a hyperlipidemic subject is defined as one whose cholesterol and triglyceride levels equal or exceed the limits set as described above for both the hypercholesterolemic and hypertriglyceridemic subjects.

"Myocardial infarction" is a focus of necrosis resulting from inadequate perfusion of the cardiac tissue. Myocardial infarction generally occurs with the abrupt decrease in coronary blood flow that follows a thrombotic occlusion of a coronary artery previously narrowed by atherosclerosis. Generally, infarction occurs when an atherosclerotic plaque fissures, ruptures, or ulcerates, and a mural thrombus forms leading to coronary artery occlusion.

The diagnosis of myocardial infarction in a subject determines the need for treating the subject according to the methods of the invention. A number of laboratory tests, well known in the art, are described, for example, in Harrison's. Generally, the tests may be divided into four main categories: (1) nonspecific indexes of tissue necrosis and inflammation, (2) electrocardiograms, (3) serum enzyme changes (e.g., creatine phosphokinase levels), and (4) cardiac imaging. A person of ordinary skill in the art could easily apply any of the foregoing tests to determine when a subject is at risk, is suffering, or has suffered, a myocardial infarction. In addition, increased levels of expression of a IL1RL-1 nucleic acid molecule, or an expression product thereof, are also, according to the present invention, important risk factors. A positively identified subject would thus benefit from a method of treatment of the invention.

According to the invention, the method involves administering to a subject having a myocardial infarction any of the foregoing IL1RL-1 molecules in an amount effective to treat the cardiovascular disorder in the subject. By "having a myocardial infarction" it is meant that the subject is at risk of developing, is currently having, or has suffered a myocardial infarction. It is believed that immediate administration of the molecule would greatly benefit the subject by inhibiting apoptotic cell-death of cardiomyocytes (the cells mostly affected by the infarct) prior to, or following the infarct. By "immediate" it is meant that administration occurs before (if it is diagnosed in time), or within 48 hours from the myocardial infarct, although administration up to 14 days after the episode may also be beneficial to the subject.

Another important embodiment of the invention is the treatment of ischemic injury resulting from arteriosclerosis. Arteriosclerosis is a term used to describe a thickening and hardening of the arterial wall. It is believed to be responsible for the majority of deaths in the United States and in most westernized societies. Atherosclerosis is one type of arteriosclerosis that is believed to be the cause of most coronary artery disease, aortic aneurysm and arterial disease of the lower extremities (including peripheral vascular arteriopathy), as well as contributing to cerebrovascular disease. Atherosclerosis is the leading cause of death in the United States.

A normal artery typically is lined on its inner-side only by a single layer of endothelial cells, the intima. The intima overlays the media, which contains only a single cell type, the smooth muscle cell. The outer-most layer of the artery is the adventitia. With aging, there is a continuous increase in the thickness of the intima, believed to result in part from migration and proliferation of smooth muscle cells from the media. A similar increase in the thickness of the intima also occurs as a result of various traumatic events or interventions, such as occurs when, for example, a balloon dilatation procedure causes injury to the vessel wall. The invention is used in connection with treating ischemic injury resulting from arteriosclerotic conditions. An arteriosclerotic condition as used herein means classical atherosclerosis, accelerated atherosclerosis, atherosclerosis lesions and any other arteriosclerotic conditions characterized by undesirable endothelial and/or vascular smooth muscle cell proliferation, including vascular complications of diabetes.

Another important embodiment of the invention is the treatment of heart failure. Heart failure is a clinical syndrome of diverse etiologies linked by the common denominator of impaired heart pumping and is characterized by the failure of the heart to pump blood commensurate with the requirements of the metabolizing tissues, or to do so only from an elevating filling pressure.

Another important embodiment of the invention is the treatment of cardiac hypertrophy. This condition is typically characterized by left ventricular hypertrophy, usually of a nondilated chamber, without obvious antecedent cause. Current methods of diagnosis include the electrocardiogram and the echocardiogram. Many patients, however, are asymptomatic and may be relatives of patients with known disease. Unfortunately, the first manifestation of the disease may be sudden death, frequently occurring in children and young adults, often during or after physical exertion.

Agents for reducing the risk of or treating a cardiovascular disorder include those selected from the group consisting of anti-inflammatory agents, anti-thrombotic agents, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), calcium channel blockers, beta-adrenergic receptor blockers, cyclooxygenase-2 inhibitors, angiotensin system inhibitors, and/or any combinations thereof. One preferred agent is aspirin.

The mode of administration and dosage of a therapeutic agent of the invention will vary with the particular stage of the condition being treated, the age and physical condition of the subject being treated, the duration of the treatment, the nature of the concurrent therapy (if any), the specific route of administration, and the like factors within the knowledge and expertise of the health practitioner.

As described herein, the agents of the invention are administered in effective amounts to treat any of the foregoing cardiovascular disorders. In general, an effective amount is any amount that can cause a beneficial change in a desired tissue of a subject. Preferably, an effective amount is that amount sufficient to cause a favorable phenotypic change in a particular condition such as a lessening, alleviation or elimination of a symptom or of a condition as a whole.

In general, an effective amount is that amount of a pharmaceutical preparation that alone, or together with further doses, produces the desired response. This may involve only slowing the progression of the condition temporarily, although more preferably, it involves halting the progression of the condition permanently or delaying the onset of or preventing the condition from occurring. This can be monitored by routine methods. Generally, doses of active compounds would be from about 0.01 mg/kg per day to 1000 mg/kg per day. It is expected that doses ranging from 50-500 mg/kg will be suitable, preferably orally and in one or several administrations per day.

Such amounts will depend, of course, on the particular condition being treated, the severity of the condition, the subject patient parameters including age, physical condition, size and weight, the duration of the treatment, the nature of concurrent therapy (if any), the specific route of administration and like factors within the knowledge and expertise of the health practitioner. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The agents of the invention may be combined, optionally, with a pharmaceutically-acceptable carrier to form a pharmaceutical preparation. The term "pharmaceutically-acceptable carrier," as used herein, means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. In some aspects, the pharmaceutical preparations comprise an agent of the invention in an amount effective to treat a disorder.

The pharmaceutical preparations may contain suitable buffering agents, including: acetic acid in a salt; citric acid in a salt; boric acid in a salt; or phosphoric acid in a salt. The pharmaceutical compositions also may contain, optionally, suitable preservatives, such as: benzalkonium chloride; chlorobutanol; parabens or thimerosal.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, intradermal, transdermal, or parenteral routes. The term "parenteral" includes subcutaneous, intravenous, intramuscular, or infusion. Intravenous or intramuscular routes are not particularly suitable for long-term therapy and prophylaxis. As an example, pharmaceutical compositions for the acute treatment of subjects having a migraine headache may be formulated in a variety of different ways and for a variety of administration modes including tablets, capsules, powders, suppositories, injections and nasal sprays.

The pharmaceutical preparations may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of an agent of the invention, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid may be used in the preparation of injectables. Formulations suitable for oral, subcutaneous, intravenous, intramuscular, etc. administrations can be found in *Remington's Pharmaceutical Sciences*, Mack Publishing Co., Easton, Pa.

Other delivery systems can include time release, delayed release or sustained release delivery systems. Such systems can avoid repeated administrations of an agent of the present invention, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775; 4,675,189; and 5,736,152; and (b) diffusional systems in which an active component permeates at a controlled rate from a polymer such as described in U.S. Pat. Nos. 3,854,480; 5,133,974: and 5,407,686. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active ingredient for at least 30 days, and preferably 60 days. Long-term sustained release implants are well-known to those of ordinary skill in the art and include some of the release systems described above. Specific examples include, but are not limited to, long-term sustained release implants described in U.S. Pat. No. 4,748,024, and Canadian Patent No. 1330939.

The invention also involves the administration, and in some embodiments co-administration, of agents other than the IL1RL-1 molecules of the invention (nucleic acids and polypeptides, and/or fragments thereof) that when administered in effective amounts can act cooperatively, additively or synergistically with a molecule of the invention to: (i) modulate cardiac cell anti-apoptotic activity, and (ii) treat any of the conditions in which cardiac cell anti-apoptotic activity of a molecule of the invention is involved. Agents other than the molecules of the invention include anti-inflammatory agents, anti-thrombotic agents, anti-coagulants, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules, calcium channel blockers, beta-adrenergic receptor blockers, cyclooxygenase-2 inhibitors, angiotensin system inhibitors, anti-hypertensive agents, and/or combinations thereof.

"Anti-inflammatory" agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; and Zomepirac Sodium. One preferred anti-inflammatory agent is aspirin.

"Anti-thrombotic" and/or "fibrinolytic" agents include plasminogen (to plasmin via interactions of prekallikrein, kininogens, Factors XII, XIIIa, plasminogen proactivator, and tissue plasminogen activator[TPA]) Streptokinase; Urokinase: Anisoylated Plasminogen-Streptokinase Activator Complex; Pro-Urokinase; (Pro-UK); rTPA (alteplase or activase; "r" denotes recombinant); rPro-UK; Abbokinase;

Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; Retaplase; Trifenagrel; Warfarin; and Dextrans.

"Anti-platelet" agents include Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; and Anagrelide.

"Lipid reducing" agents include gemfibrozil, cholystyramine, colestipol, nicotinic acid, probucol lovastatin, fluvastatin, simvastatin, atorvastatin, pravastatin, and cirivastatin.

"Direct thrombin inhibitors" include hirudin, hirugen, hirulog, agatroban, PPACK, and thrombin aptamers.

"Glycoprotein IIb/IIIa receptor inhibitors" embraces both antibodies and non-antibodies, and include, but are not limited, to ReoPro (abcixamab), lamifiban, and tirofiban.

"Calcium channel blockers" are a chemically diverse class of compounds having important therapeutic value in the control of a variety of diseases including several cardiovascular disorders, such as hypertension, angina, and cardiac arrhythmias (Fleckenstein, *Cir. Res.* v. 52, (suppl. 1), p. 13-16 (1983); Fleckenstein, *Experimental Facts and Therapeutic Prospects*, John Wiley, New York (1983); McCall, D., *Curr Pract Cardiol*, v. 10, p. 1-11 (1985)). Calcium channel blockers are a heterogeneous group of drugs that prevent or slow the entry of calcium into cells by regulating cellular calcium channels. (Remington, *The Science and Practice of Pharmacy*, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, aminone, amlodipine, bencyclane, felodipine, fendiline, flunarizine, isradipine, nicardipine, nimodipine, perhexilene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

Cyclooxygenase-2 (COX-2) is a recently identified form of a cyclooxygenase. "Cyclooxygenase" is an enzyme complex present in most tissues that produces various prostaglandins and thromboxanes from arachidonic acid. Non-steroidal, anti-inflammatory drugs exert most of their anti-inflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It and was originally identified in bovine seminal vesicles.

Cyclooxygenase-2 (COX-2) has been cloned, sequenced and characterized initially from chicken, murine and human sources (see, e.g., U.S. Pat. No. 5,543,297, issued Aug. 6, 1996 to Cromlish et al., and assigned to Merck Frosst Canada, Inc., Kirkland, Calif., entitled: "Human cyclooxygenase-2 cDNA and assays for evaluating cyclooxygenase-2 activity"). This enzyme is distinct from COX-1. COX-2 is rapidly and readily inducible by a number of agents including mitogens, endotoxin, hormones, cytokines and growth factors. As prostaglandins have both physiological and pathological roles, the constitutive enzyme, COX-1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar anti-inflammatory, antipyretic and analgesic properties to a conventional non-steroidal anti-inflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective "COX-2 inhibitors" are known in the art. These include, but are not limited to, COX-2 inhibitors described in U.S. Pat. No. 5,474,995 "Phenyl heterocycles as COX-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S.Pat. No. 5,604,253 "N-Benzylindol-3-yl propanoic acid derivatives as cyclooxygenase inhibitors"; U.S. Pat. No. 5,604,260 "5-Methanesulfonamido-1-indanones as an inhibitor of cyclooxygenase-2"; U.S. Pat. No. 5,639,780 N-Benzyl indol-3-yl butanoic acid derivatives as cyclooxygenase inhibitors"; U.S. Pat. No. 5,677,318 Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-Diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789, 413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742

"Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif. or Merck & Co., Inc. (Rahway, N.J.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An "angiotensin system inhibitor" is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

"Angiotensin II antagonists" are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [($San^1$)($Val^5$)($Ala^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile), imidazole-5-acetic acid (see Long et al., *J. Pharmacol. Exp. Ther.* 247(1), 1-7 (1988)); 4, 5, 6, 7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(−1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxyphenyl)methyl] 1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D. Searle and Company).

"Angiotensin converting enzyme," (ACE), is an enzyme which catalyzes the conversion of angiotensin I to angiotensin II. ACE inhibitors include amino acids and derivatives thereof, peptides, including di- and tripeptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

"Renin inhibitors" are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. No. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies described above.

Anticoagulant agents include, but are not limited to, Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bivalirudin; Bromindione; Dalteparin Sodium; Desirudin; Dicumarol; Heparin Calcium; Heparin Sodium; Lyapolate Sodium; Nafamostat Mesylate; Phenprocoumon; Tinzaparin Sodium; and Warfarin Sodium.

Heparin may stabilize symptoms in evolving stroke, but anticoagulants are useless (and possibly dangerous) in acute completed stroke, and are contraindicated in hypertensives because of the increased possibility of hemorrhage into the brain or other organs. Although the timing is controversial, anticoagulants may be started to prevent recurrent cardiogenic emboli. Clot lysing agents, including tissue plasminogen activator and streptokinase, are being evaluated for the very early treatment of acute stroke. Nimodipine has recently been shown to improve survival and clinical outcome after ischemic stroke.

Other than aspirin, ticlopidine is another antiplatelet agent that has been shown to be beneficial for stroke treatment. Endarterectomy may be indicated in patients with 70 to 99 percent narrowing of a symptomatic internal carotid artery. However, most authorities agree that carotid endarterectomy is not indicated in patients with TIAs that are referable to the basilar-vertebral system, in patients with significant deficits from prior strokes, or in patients in whom a stroke is evolving.

HMG-CoA (3-hydroxy-3-methylglutaryl-coenzyme A) reductase is the microsomal enzyme that catalyzes the rate limiting reaction in cholesterol biosynthesis (HMG-CoA6Mevalonate). An HMG-CoA reductase inhibitor inhibits HMG-CoA reductase, and as a result inhibits the synthesis of cholesterol. A number of HMG-CoA reductase inhibitors has been used to treat subjects with hypercholesterolemia. More recently, HMG-CoA reductase inhibitors have been shown to be beneficial in the treatment of stroke (Endres M, et al., *Proc Natl Acad Sci USA,* 1998, 95:8880-5).

HMG-CoA reductase inhibitors useful for co-administration with the agents of the invention include, but are not limited to, simvastatin (U.S. Pat. No. 4,444,784); lovastatin (U.S. Pat. No. 4,231,938); pravastatin sodium (U.S. Pat. No. 4,346,227); fluvastatin (U.S. Pat. No. 4,739,073); atorvastatin (U.S. Pat. No. 5,273,995); cerivastatin, and numerous others described in U.S. Pat. Nos. 5,622,985; 5,135,935; 5,356,896; 4,920,109; 5,286,895; 5,262,435; 5,260,332; 5,317,031; 5,283,256; 5,256,689; 5,182,298; 5,369,125; 5,302,604; 5,166,171; 5,202,327; 5,276,021; 5,196,440; 5,091,386; 5,091,378; 4,904,646; 5,385,932; 5,250,435; 5,132,312; 5,130,306; 5,116,870; 5,112,857; 5,102,911; 5,098,931; 5,081,136; 5,025,000; 5,021,453; 5,017,716; 5,001,144; 5,001,128; 4,997,837; 4,996,234; 4,994,494; 4,992,429; 4,970,231; 4,968,693; 4,963,538; 4,957,940; 4,950,675; 4,946,864; 4,946,860; 4,940,800; 4,940,727; 4,939,143; 4,929,620; 4,923,861; 4,906,657 4,906,624; and 4,897,402, the disclosures of which patents are incorporated herein by reference.

Nitric oxide (NO) has been recognized as a messenger molecule with many physiologic roles, in the cardiovascular, neurologic and immune systems (Griffith, T M et al., *J Am Coll Cardiol,* 1988, 12:797-806). It mediates blood vessel relaxation, neurotransmission and pathogen suppression. NO is produced from the guanidino nitrogen of L-arginine by NO Synthase (Moncada, S and Higgs, E A, *Eur J Clin Invest,* 1991, 21:361-374). Agents that upregulate endothelial cell Nitric Oxide Synthase include, but are not limited to, L-arginine, rho GTPase function inhibitors (see International Application WO 99/47153, the disclosure of which is incorporated herein by reference), and agents that disrupt actin cytoskeletal organization (see International Application WO 00/03746, the disclosure of which is incorporated herein by reference).

"Co-administering," as used herein, refers to administering simultaneously two or more compounds of the invention (e.g., a IL1RL-1 nucleic acid and/or polypeptide, and an agent known to be beneficial in the treatment of, for example, a cardiovascular condition, e.g., an anticoagulant-), as an admixture in a single composition, or sequentially, close enough in time so that the compounds may exert an additive or even synergistic effect, i.e., on reducing cardiomyocyte cell-death in a cardiovascular condition.

The invention also embraces solid-phase nucleic acid molecule arrays. The array consists essentially of a set of nucleic acid molecules, expression products thereof, or fragments (of either the nucleic acid or the polypeptide molecule) thereof, the set including a IL1RL-1 nucleic acid molecule and at least one control nucleic acid molecule fixed to a solid substrate. In preferred embodiments, the set of nucleic acid molecules comprises a maximum number of 100 different nucleic acid molecules. In important embodiments, the set of nucleic acid molecules comprises a maximum number of 10 different nucleic acid molecules.

According to the invention, standard hybridization techniques of microarray technology are utilized to assess patterns of nucleic acid expression and identify nucleic acid expression. Microarray technology, which is also known by other names including: DNA chip technology, gene chip technology, and solid-phase nucleic acid array technology, is well known to those of ordinary skill in the art and is based on, but not limited to, obtaining an array of identified nucleic acid probes (e.g., molecules described elsewhere herein such as IL1RL-1) on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in Nature Genetics, Vol. 21, January 1999, the entire contents of which is incorporated by reference herein.

According to the present invention, microarray substrates may include but are not limited to glass, silica, aluminosilicates, borosilicates, metal oxides such as alumina and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of two or more of the nucleic acid molecules set forth as SEQ ID NOs: 1 and/or 3. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or olignucleotide to the substrate. These agents or groups may include, but are not limited to amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (Nature Genetics, Vol. 21, January 1999) or chromium. In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezo-electric delivery. Probes may be covalently linked to the substrate with methods that include, but are not limited to, UV-irradiation and heat.

Targets are nucleic acids selected from the group, including but not limited to, DNA, genomic DNA, cDNA, RNA, mRNA and may be natural or synthetic. In all embodiments, nucleic acid molecules from subjects suspected of developing or having a cardiovascular condition, are preferred. In certain embodiments of the invention, one or more control nucleic acid molecules are attached to the substrate. Preferably, control nucleic acid molecules allow determination of factors including but not limited to: nucleic acid quality and binding characteristics; reagent quality and effectiveness; hybridization success; and analysis thresholds and success. Control nucleic acids may include, but are not limited to, expression products of genes such as housekeeping genes or fragments thereof.

To select a set of cardiovascular disease markers, the expression data generated by, for example, microarray analysis of gene expression, is preferably analyzed to determine which genes in different categories of patients (each category of patients being a different cardiovascular disorder), are significantly differentially expressed. The significance of gene expression can be determined using Permax computer software, although any standard statistical package that can discriminate significant differences is expression may be used. Permax performs permutation 2-sample t-tests on large arrays of data. For high dimensional vectors of observations, the Permax software computes t-statistics for each attribute, and assesses significance using the permutation distribution of the maximum and minimum overall attributes. The main use is to determine the attributes (genes) that are the most different between two groups (e.g., control healthy subject and a subject with a particular cardiovascular disorder), measuring "most different" using the value of the t-statistics, and their significance levels.

Expression of cardiovascular disease nucleic acid molecules can also be determined using protein measurement methods to determine expression of SEQ ID NOs: 2 and/or 4, e.g., by determining the expression of polypeptides encoded by SEQ ID NOs: 1 and/or 3, respectively. Preferred methods of specifically and quantitatively measuring proteins include, but are not limited to: mass spectroscopy-based methods such as surface enhanced laser desorption ionization (SELDI; e.g., Ciphergen ProteinChip System), non-mass spectroscopy-based methods, and immunohistochemistry-based methods such as 2-dimensional gel electrophoresis.

SELDI methodology may, through procedures known to those of ordinary skill in the art, be used to vaporize microscopic amounts of tumor protein and to create a "fingerprint" of individual proteins, thereby allowing simultaneous measurement of the abundance of many proteins in a single sample. Preferably SELDI-based assays may be utilized to characterize cardiovascular conditions as well as stages of such conditions. Such assays preferably include, but are not limited to the following examples. Gene products discovered by RNA microarrays may be selectively measured by specific (antibody mediated) capture to the SELDI protein disc (e.g., selective SELDI). Gene products discovered by protein screening (e.g., with 2-D gels), may be resolved by "total protein SELDI" optimized to visualize those particular markers of interest from among SEQ ID NOs: 1 and/or 3. Predictive models of tumor classification from SELDI measurement of multiple markers from among SEQ ID NOs: 1 and/or 3, may be utilized for the SELDI strategies.

The use of any of the foregoing microarray methods to determine expression of cardiovascular disease nucleic acids can be done with routine methods known to those of ordinary skill in the art and the expression determined by protein measurement methods may be correlated to predetermined levels of a marker used as a prognostic method for selecting treatment strategies for cardiovascular disease patients.

The invention will be more fully understood by reference to the following examples. These examples, however, are merely intended to illustrate the embodiments of the invention and are not to be construed to limit the scope of the invention.

EXAMPLES

Example 1

Experimental Protocols Materials and Methods

Mechanical Strain Device

Experiments of mechanically overloading cardiomyocytes have generally been performed by stretching cells with no control of the cardiac cycle, an approach that does not allow distinction between mechanical overload in contraction versus relaxation. In the present study, we designed and constructed a unique experimental system that allows precisely controlled mechanical strains as well as electrical pacing in cultured cardiomyocytes, to investigate, inter alia, how cardiomyocyte mechanotransduction is regulated by the cardiac cycle, and identify genes that are involved in such regulation.

The Pacing-Strain Device. The approach to mechanical stimulation used an apparatus that has multiple platens that contact the underside of silicone elastomer membranes to apply a spatially isotropic biaxial strain profile to the membrane (Schaffer J L, et al., *J Orthop Res,* 1993, 12:709-719; and U.S. Provisional Patent application filed on Jul. 16, 1999 entitled "AN APPARATUS FOR STUDYING MYOCARDIAL MECHANICAL OVERLOAD HYPERTROPHY AND USES THREFOR, by Richard T. Lee, and bearing Attorney Docket no. 100038.130 and express mail no. EL110243781US). Six individual 78 mm membranes can be stretched at once with varying amplitudes of strain by controlling displacement of each platen with a stepper motor. Measured Green strains are accurate to ~±0.25% at strains from 1-14% (Cheng G C, et al., *Circ Res,* 1997, 80:28-36; Brown T D, *J Biomechanics,* 2000, 33:3-14). Throughout this study, 8% biaxial strain was used.

To control the timing of mechanical strain relative to the cardiac cycle, the computer paced each dish electrically, and controlled: the phase between the mechanical strain and the electrical impulse, the electrical impulse duration, and the voltage of the impulse. In addition, the electrical impulses had alternating polarity to minimize electrochemical effects such as pH gradients at the electrodes. The two outputs were each connected to a single set of electrodes in each dish. The dishes were paced in parallel with a resistance of approximately 500 ohms per dish.

The positive and negative voltage sources were provided by two power supplies (6545A, Hewlett Packard Company, Palo Alto, Calif.). The control circuit was divided into two parts: a high voltage circuit and a low voltage or digital signal circuit. The high voltage circuit was a gate that switched the output based on the input signal. The low voltage circuit accepted two control signals from the computer and accepted the pulse width from a variable resistor, which controlled both the positive and negative voltage gates. The low voltage circuit allowed a voltage pulse between 0-120V DC amplitude and 2-37 ms duration. Lights provided continuous monitoring of the pulses, and the timing of the circuits and calibration were validated by oscilloscope.

The electrodes for each dish were two arc-shaped $AgCl_2$ wire electrodes at the base of the inner surface of the dish, just above the deformable membrane. The electrodes were premade, ethanol-sterilized, and placed into the dish just prior to each experiment to minimize potential toxicity from silver. Using this method no cellular death or detachment was observed in 24 hr experiments. Each arc was 120 degrees; we performed a two dimensional finite element analysis to estimate the uniformity of the potential field with this configuration. These calculations estimate a spatial variation in the potential field of {root mean square}=29%. Thus, this system provides highly uniform biaxial mechanical strain, with a relatively small variation in the voltage field.

Mechanical stimulation protocols. We imposed strain only during first third of the cardiac cycle by electrical stimulation for strain imposed during the "systolic phase", and only during one third of the cardiac cycle in the relaxation phase for strain imposed during "diastolic phase," respectively. Conditions used in this study were: (1) control; (2) strain, no pacing; (3) pacing, no strain; (4) strain imposed during systolic phase; and (5) strain imposed during diastolic phase.

Neonatal rat ventricular myocytes (NRVM) from 1-day old Sprague-Dawley rats were isolated by previously described methods (Springhorn J P, and Claycomb W C., *Biochem J,* 1989; 258:73-78; Arstall M A, et al., *J Mol Cell Cardiol,* 1998, 30:1019-25). NRVM were plated on the coated membrane dish at a density of 2,000,000 cells/dish in DMEM containing 7% FCS and incubated 24 h. Approximate cell confluence was 85-90%. NRVM were then made quiescent by washing with 10 ml of Hanks' balanced salt solution (HBSS, 138 mM NaCl, 5.3 mM KCl, 4.0 mM $NaHCO_3$, 1.3 mM $CaCl_2$, 0.5 mM $MgCl_2$, 0.4 mM $MgSO_4$, 0.4 mM $KH_2PO_4$, 0.3 mM $Na_2HPO_4$, 5.6 mM glucose; Life Technologies, Inc., Rockville, Md.) twice and incubating with 26 ml of DMEM containing 0.2% FCS for 48-72 hours.

In these cell culture conditions, cells beat at 40-60 beats/minute. At this rate, we have observed negligible competition when pacing at a rate of 70 beats/minute. We performed trial capture experiments; nine locations on each dish were sampled. Capture efficiency was similar at all locations, and maximal capture occurred at 60 V and above with 10 ms of pulse width. Therefore, a voltage of 70 V with 10 ms of impulse duration at a rate of 1.2 Hz (70 beats/minute) was selected. Under these conditions we did not observe partial cell detachment.

Transcriptional Profiling. The DNA microarray experiment was performed with rat neonatal cardiac myocytes cultured on fibronectin-coated membranes with serum-free medium for 48 hours. Cells were deformed with an 8% deformation imposed only during systole for a period of 30 minutes, and RNA was prepared after 6 hours of subsequent no strain conditions and no pacing conditions. This time point was based upon previous studies demonstrating that the gene tenascin (positive control for cardiomyocytes) is induced at this time period. The DNA microarray hybridization experiment was performed using the Affymatrix GeneChip RGU34A (Affymetrix, Inc., Santa Clara, Calif.). Data were analyzed using Affymatrix software.

Northern Analyses. The cDNA clones for differentially expressed genes were obtained by PCR using the GenBank sequences. Each clone was sequenced from both 5' and 3' ends to confirm identity. Positive elements in the DNA microarray were confirmed by Northern blot hybridization analysis in at least three independent experiments using three different sources of NRVMs. Total RNA was isolated by the guanidium thiocyanate and phenol chloroform method (Chomcyznski, et al., *Anal. Biochem.,* 1987, 162:156-159). For Northern blotting, 15 µg RNA was loaded on a 1.0% agarose-formaldehyde gel (2.0 mol/l), transferred to a nylon membrane (Amersham Pharmacia Biotech AB, Piscataway, N.J.), and UV cross-linked with a UV Stratalinker (Stratagene, Inc., La Jolla, Calif.). Each probe was hybridized with ExpressHyb solution (Clontech Labs., Inc., Palo Alto, Calif.) at 68° C. for 1 hour. The membrane was washed with 2×SSC, 0.05% SDS solution for 30 to 40 minutes and three times at room temperature and 0.1×SSC, 0.1% SDS solution with continuous shaking at 50° C. for 40 minutes. The membrane was exposed to film at −80° C., and radiographs were scanned and analyzed with Optimas 5.0 software (Optimas Co./Media Cybernetics, Silver Springs, Md.). Densitometric units were normalized to the ethidium-stained 28S ribosomal subunit on the membrane.

Results. FIG. 1 shows the timecourse (early, left; late, right) of the induction of IL1RL-1 mRNA expression by 8% cyclic mechanical strain in neonatal cardiac myocytes in culture. Maximal induction occurs at 3 hours and is sustained for 15 hours.

Figure 2:
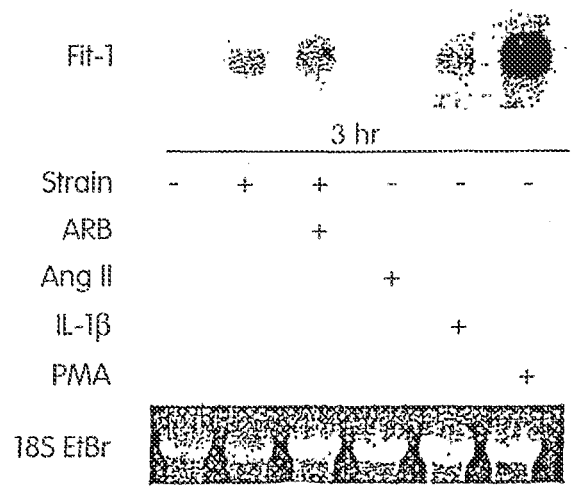
FIG. 2 depicts by a Northern Blot the effects of 8% cyclic mechanical strain, angiotensin receptor blockade, angiotensin II, IL-1b, and phorbol ester, on the expression of IL1RL-1 in cultured cardiac myocytes over the course of time.

FIG. 2 shows the effects of 8% mechanical strain, angiotensin receptor blockade (ARB, CP-19116, 100 nM), angiotensin II (Ang II, 50 nM), interleukin-1β (IL-1β, 10 ng/ml), and phorbol ester (PMA, 200 nM) for 3 hours on the induction of IL1RL-1 mRNA expression in cultured neonatal rat cardiac myocytes. The induction of IL1RL-1 mRNA expression by strain was not blocked by angiotensin receptor blockade; furthermore, treatment with angiotensin II did not induce IL1RL-1 mRNA expression. Treatment with both IL-1β and PMA were associated with an induction of IL1RL-1 mRNA expression in the absence of mechanical strain.

Figure 3:
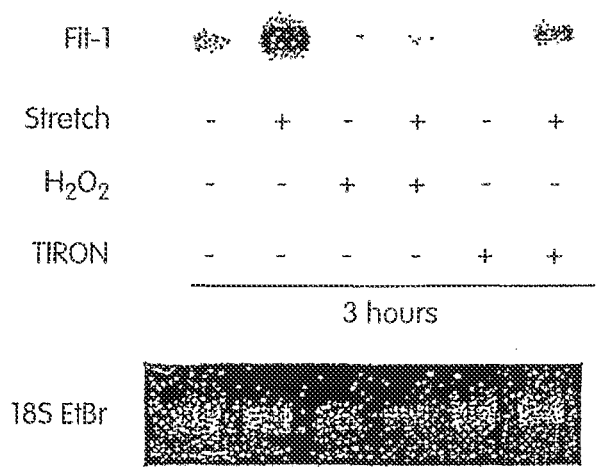
FIG. 3 depicts by a Northern Blot the effects of 8% cyclic mechanical strain, hydrogen peroxide, and TIRON, on the expression of IL1RL-1 in cultured cardiac myocytes over the course of time.

FIG. 3 shows the effects of 8% mechanical strain, hydrogen peroxide ($H_2O_2$, 100 uM) and the antioxidant, TIRON (10 mM) on the induction of IL1RL-1 mRNA expression. Unlike the mRNA expression of the mechanically induced Tenascin-C gene which is induced by $H_2O_2$ in the absence of mechanical strain and blocked by TIRON, $H_2O_2$ does not induce IL1RL-1 in the absence of strain and blocks the strain-induced induction of IL1RL-1. TIRON slightly attenuated the mRNA expression of IL1RL-1 in the absence and presence of strain.

Figure 4:
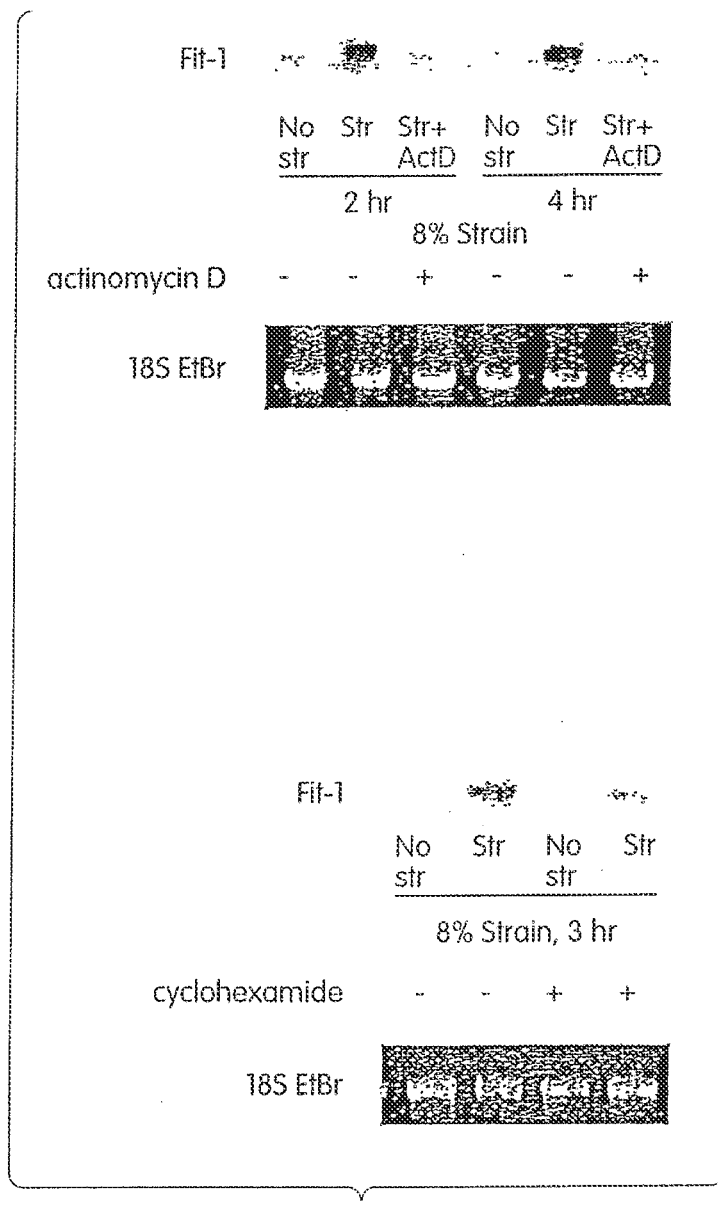
FIG. 4 depicts by a Northern Blot the effects of actinomycin D and cyclohexamide on the induction of IL1RL-1 expression during an 8% cyclic mechanical strain on cardiac myocytes over the course of time.

FIG. 4 shows the effects of actinomycin D (5 μg/ml, left) and cyclohexamide (10 μg/ml, right) on the induction of IL1RL-1 mRNA expression by 8% mechanical strain. Actinomycin D and cyclohexamide were applied during mechanical strain. Actinomycin D blocked the induction of IL1RL-1 mRNA expression at both 2 and 4 hours suggesting that the induction of IL1RL-1 in response to strain is due to increased transcription of IL1RL-1. The protein synthesis inhibitor, cyclohexamide blocked the induction of IL1RL-1 mRNA expression in response to strain suggesting that new protein synthesis is required for the induction of IL1RL-1 mRNA expression.

Figure 5:
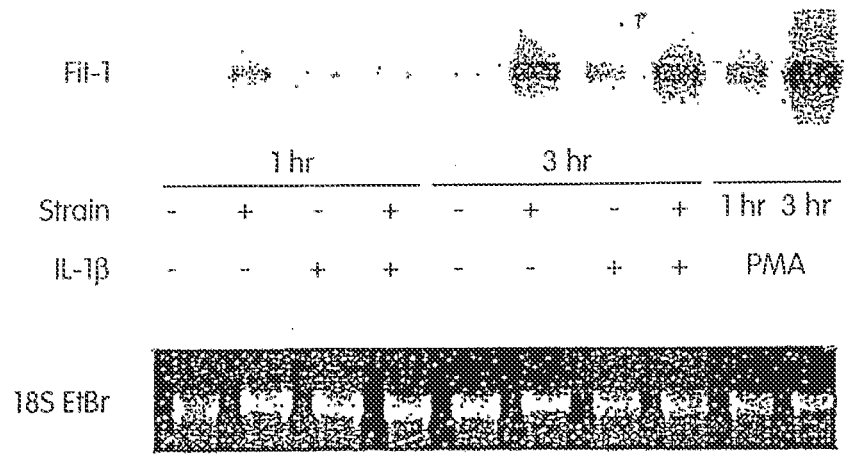
FIG. 5 depicts by a Northern Blot the effects of 8% cyclic mechanical strain alone and in combination with IL-1b, and phorbol ester in the absence of strain, on the expression of IL1RL-1 in cultured cardiac myocytes over the course of time.

FIG. 5 shows the effects of 8% mechanical strain alone and in combination with interleukin-1β (IL-1β, 10 ng/ml), and phorbol ester in the absence of strain (PMA, 100 ng/ml) on IL1RL-1 mRNA expression in cultured neonatal cardiac myocytes. Both IL-1β and mechanical strain alone induced IL1RL-1 mRNA expression but the induction of IL1RL-1 by mechanical strain in the presence of IL-1β was not further increased suggesting that mechanical strain and IL-1β do not act in a synergistic or additive manner on the induction of IL1RL-1. The strongest induction of IL1RL-1 mRNA expression is seen with PMA. The rank order potency for the induction of IL1RL-1 mRNA expression is PMA>strain>IL-1β.

Figure 6:
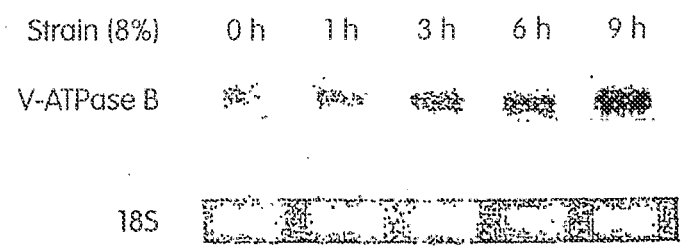
FIG. 6 depicts by a Northern Blot the effects of an 8% cyclic mechanical strain on the expression of vacuolar ATPase in cultured cardiac myocytes over the course of time.

FIG. 6 shows neonatal rat cardiac myocytes were exposed to 8% strain for 0, 1, 3, 6, 9 hours. Total RNA was isolated using a RNeasy kit. Five μg of total RNA were size-separated on 1% agarose-formaldehyde gel and transferred to nylon membrane. After cross-linking with UV light, membrane was hybridized with $^{32}$P-labeled probe specific for V-ATPase B subunit. The membrane was then exposed to x-ray film for 3 hours at −80° C. with an intensifying screen.

Example 2

Introduction

Cytokines and Cardiac Injury. Stress-activated cytokines participate in many forms of cardiac injury and pathophysiological conditions, the most characterized ones being tumor necrosis factor-α, interleukin-1 and interleukin-6. These molecules are not constitutively expressed in the normal heart but are rapidly induced during ischemia and reperfusion or upon hemodynamic overloading, suggesting that they play an important role in the initial myocardial response to stress, injury or growth stimuli (Mann D L, *Cytokine and Growth Factor Reviews.* 1996; 7:341-354; St. John Sutton M G, et al. *Circulation.* 2000; 101:2981-2988). However, cytokines have also been shown to be stably expressed in pathologic myocardial conditions including ischemic heart disease and heart failure and are associated with a poor prognosis (Pulkki K J, et al. *Annals of Medicine.* 1997; 29:339-343; Kubota T, et al *Proc Natl Acad Sci.* 1998; 95:6930-6935; Aukrust P, et al. *Am J Cardiol* 1999; 83:376-382; MacGowan G A, et al. *Am J Cardiol* 1997; 79:1128-1132; Roig E, et al. *Am J Cardiol* 1998; 688-690; Tsutamoto T, et al. *J Am Coll Cardiol* 1998; 31:391-398; Prabhu S D, et al. *Circulation.* 2000; 101:2103-2109; Murray D R, et al. *Annu Rev Immunol.* 2000; 18:451-494).

Interleukin-1 signaling through the interleukin-1 receptor is an early event in inflammatory cytokine signaling in many different systems (Trehu E G., *Clin Cancer Res.* 1996; 8:1341-51). In cardiac injury, interleukin-6 is produced by cardiac myocytes secondary to stimulation with interleukin-1, tumor necrosis factor-α, or lipopolysaccharide and has been detected in the post-ischemic lymph during reperfusion of ischemic myocardium (Gwechenberger M, et al. *Circulation* 1999; 99:546-551). Recently recognized is the potential expression of counteracting anti-inflammatory cytokines in cardiac disease secondary to interleukin-1 signaling. Interleukin-4 and interleukin-10 can suppress the synthesis of tumor necrosis factor-α and enhance the release of soluble tumor necrosis factor receptors, which are ligand sinks for tumor necrosis factor (Joyce D A., 1994; *Eur. J. Immunol.* 11:2699-705). Interleukin-10 is increased in patients with heart failure (Yamaoka M, et al. *Jpn Circ J.* 1999; 63:951-956) and interleukin-10 serum levels are increased when tumor necrosis factor-α serum levels are increased in patients with dilated cardiomyopathy (Ohtsuka T, et al. *J Am Coll Cardiol.* 2001; 37:412-417).

T1/ST2 (IL1RL-1): A Novel Mechanically Induced Receptor. We have identified a novel potential stress-activated signaling pathway in the heart: regulation of the induction of an interleukin-1 family member gene, T1/ST2. Little is known of the induction, signaling and function of T1/ST2 in any cell type and T1/ST2 was shown in separate areas of investigation to have two seemingly unrelated functions. One of these is growth regulation and the other is immune modulation. Both compensatory hypertrophic growth and immune/inflammatory modulation are involved in the pathophysiology of cardiovascular diseases.

Growth. The T1/ST2 gene was first identified by its induction following serum stimulation of resting mouse 3T3 fibroblasts, suggesting that the T1/ST2 gene participates in growth regulation (Tominaga S., *FEBS Letters* 1989; 258:301-304). The same group later identified a longer transcript consisting of transmembrane and cytoplasmic domains homologous to the full-length interleukin-1 receptor (Yanagisawa K, et al. *FEBS Letters.* 1993; 318:83-87).

Immunity. T1/ST2 is expressed on T helper-2, but not T helper-1, cells of the adaptive immune system, which produce interleukin-4, interleukin-5 and interleukin-10 (Yanagisawa K I, et al. *J Biochem.* 1997; 121:95-103; Coyle A J, et al. *J Exp Med.* 1999; 190:895-902). T helper-2 cells mediate beneficial responses to infection, but are detrimental in the development of allergy and asthma. There is a strong correlation between expression of T1/ST2 and interleukin-4 production on T helper-2 cells (Coyle A J, et al. *J Exp Med.* 1999; 190:895-902). T1/ST2 plays a critical role in differentiation to and activation of T helper-2 but not T helper-1 cells (O'Neill L A J, et al. *Immunology Today.* 2000; 21:206-209).

Inhibition of T1/ST2 signaling attenuated T helper 2-mediated induction of eosinophil inflammatory responses in lung and inhibited cytokine secretion from T helper-2 cells without modifying interferon-gamma secretion from T helper-1 cells (Coyle A J, et al. *J Exp Med.* 1999; 190:895-902). These studies indicate that expression of T1/ST2 can alter the cytokine profile in favor of expression of interleukin-4, interleukin-5 and interleukin-10. Interleukin-10 has recently been shown to have anti-inflammatory effects in the setting of cardiac injury (Ohtsuka T, et al. *J Am Coll Cardiol.* 2001; 37:412-417). Similarly, the absence of T1/ST2 expression could result in a shift towards interferon-gamma expression, which may be deleterious following myocardial injury.

Taken together, the involvement of T1/ST2 in growth responses and immune function coupled with the clinical recognition of the role of cytokines in the inflammatory response to ischemia/reperfusion are suggestive that T1/ST2 activation is a growth- or stress-activated signaling pathway that contributes to myocardial growth and remodeling.

Phenotype of T1/ST2 Null Mice. (Townsend M J, et al. *J Exp Med.* 2000; 191:1069-1075). The absence of T1/ST2 in T1/ST2 null mice does not compromise their basal immune function in the absence of immune challenge. However, T1/ST2 null mice have an impaired ability to generate IL-4, IL-5, and IL-10, but not IFN-γ (a Th1 cytokine) and to generate a T helper-2 inflammatory response during eosinophilic infiltration in the lung (a Th2 response).

We have begun to study the induction of T1/ST2 in cardiac myocytes and its involvement in survival/death signaling within the context of the myocyte signaling pathways. Preliminary studies presented below show that T1/ST2 is induced in cardiac myocytes in response to interleukin-1 and mechanical strain and that the induction of T1/ST2 by interleukin-1 may be dependent on NF-κB activation. T1/ST2 mRNA is also induced in human adult vascular smooth muscle cells in response to interleukin-1. T1/ST2 protein is expressed in the mouse heart early after myocardial ischemia in vivo as well as in human aorta tissue from patients with unstable plaque.

Figure 8:
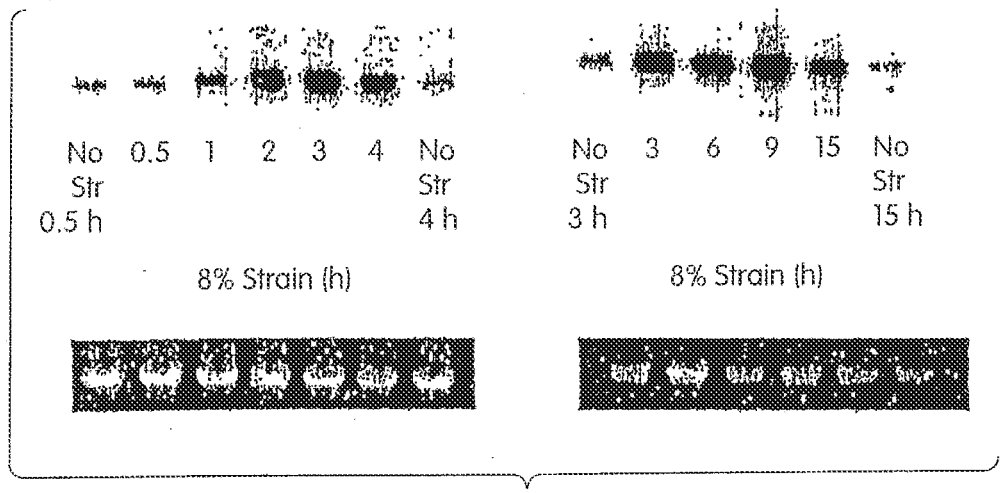
FIG. 8 depicts early (left) and late (right) time course of the mRNA induction of T2/ST2 by mechanical strain in cardiac myocytes. Maximal induction occurs at 3 hours, is sustained for 9 hours and declines by 15 hours. Top panels, T1/ST2 RNA; bottom panels, ethidium bromide. No str, no strain.

Results:

IN VITRO STUDIES. The following studies demonstrate the induction of T1/ST2 by mechanical strain and interleukin-1, possibly through activation of NF-κB. Both transcripts of T1/ST2 (that is, IL1RL-1S-soluble- and IL1RL-1M-membrane-) are induced by strain in cardiac myocytes although the more abundant transcript was the soluble isoform. T1/ST2 mRNA is induced by mechanical strain in cultured neonatal cardiac myocytes (FIG. 8).

T1/ST2 mRNA is induced by mechanical strain in cultured neonatal cardiac myocytes. Neonatal rat ventricular myocytes were isolated by collagenase digestion, plated on fibronectin-coated silicone membrane dishes at a density of 3.5 million cells/dish in 13 ml media as previously described (Yamamoto K, et al. *J Biol. Chem.* 1999; 274:21840-21846). This technique yields cultures with ≥95% myocytes. Mechanical deformation was applied using a device that provides uniform biaxial cyclic strain as previously described (Yamamoto K, et al. *J Biol. Chem.* 1999; 274:21840-21846). RNA was extracted (Qiagen) and Northern blotting was performed using as a probe a $^{32}$P-labelled 600 bp PCR fragment specific to rat T1/ST2. Maximal induction occurs at 3 hours, is sustained for 9 hours and declines by 15 hours.

Figure 9:
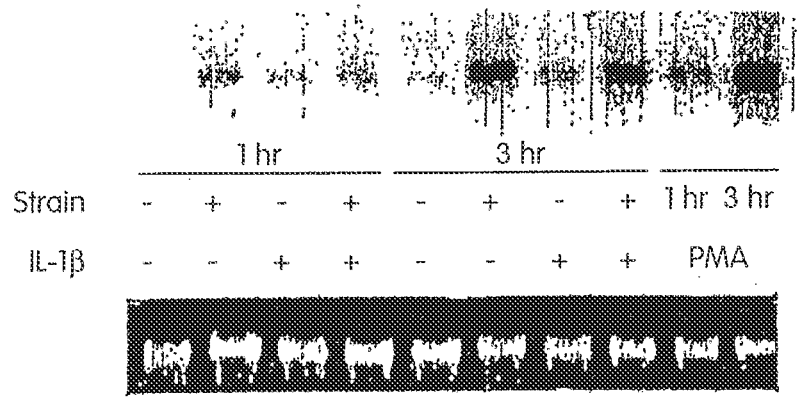
FIG. 9 depicts mRNA induction of T1/ST2 by mechanical strain (8%), interleukin-1 (10 ng/ml) and phorbol ester (PMA, 200 nM) at 1 and 3 hours. PMA>strain>IL-1. Top panel, T1/ST2 mRNA, bottom panel, ethidium bromide.

Both interleukin-1β and mechanical strain each induce T1/ST2 RNA in cardiac myocytes (FIG. 9). Shown is the induction of T1/ST2 by interleukin-1 and strain. We also found that the induction of T1/ST2 by mechanical strain in the presence of interleukin-1β was not further increased suggesting that interleukin-1 does not sensitize myocytes to the effects of mechanical strain (or vice versa) on the induction of T1/ST2. The 1 hour time point was included in the event that induction by strain is saturated at 3 hours and therefore masks an additive effect of interleukin-1β. Shown in the two right lanes are the effects of phorbol ester (PMA) at 1 and 3 hours. The rank order potency for the induction of T1/ST2 mRNA expression is PMA>strain>interleukin-1β. Since interleukin-1β signals through NF-κB and PMA through PKC these results suggest that NF-κB and PKC activation both participate in the induction of T1/ST2.

Figure 10:
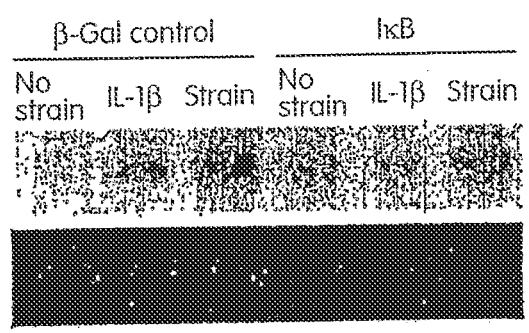
FIG. 10 shows that T1/ST2 may be a gene induced by NF-κB activation during IL-1/IL-receptor signaling in cardiac myocytes. IL-1 and strain induced T1/ST2 mRNA in the presence of infection with control adenovirus (left). With infection of IκB adenovirus (right), which decreases NF-κB DNA binding activity, the IL-1 induction of T1/ST2 was blocked. The strain induction of T1/ST2 was partially blocked by IκB adenovirus infection suggesting another pathway for induction of T1/ST2 by strain. Top panel, T1/ST2 mRNA; bottom panel, ethidium bromide.

T1/ST2 may be a NF-κB target gene in cardiac myocytes through interleukin-1/interleukin-1 receptor signaling (FIG. 10). Previously reported by us (Yamamoto K, et al. *J Biol. Chem.* 1999; 274:21840-21846), mechanical strain of cardiac myocytes activates NF-κB. To investigate the role of NF-κB in interleukin-1β and strain induction of T1/ST2 RNA, we overexpressed IκBα, which decreases NF-κB DNA binding activity. Cultured cardiac myocytes were infected with IκBα overexpression adenovirus vector or with β-galactosidase control vector and exposed for 4 hours to 8% cyclic mechanical strain or interleukin-1 (10 ng/ml). RNA was analyzed by Northern blotting with $^{32}$P-labeled IL1RL-1 cDNA probe. Ectopic expression of IκBα blocked interleukin-1β induction of T1/ST2-1 mRNA and partially blocked strain induction of T1/ST2 mRNA expression when compared with T1/ST2 induction in cells treated with the β-galactosidase control vector. These results suggest that T1/ST2 is an early, NF-κB target gene through interleukin-1/interleukin-1 receptor signaling. In contrast, pathways in addition to NF-κB activation may be involved in the induction of T1/ST2 RNA by mechanical strain. T1/ST2 mRNA is also induced by interleukin-1 but not PMA or tumor necrosis factor (TNF) in human adult vascular smooth muscle cells.

In addition to the above-noted results, we have shown that T1/ST2 is induced secondary to NF-κB activation by interleukin-1 and NF-κB is linked to cardiac myocyte survival. Further in vitro studies are performed to confirm that T1/ST2 activation is linked to cell growth and survival.

IN VIVO STUDIES

Materials and Methods

Experimental myocardial infarction in mice. Experimental procedures on mice were approved by the Harvard Medical School Standing Committee on Animals. Experimental myocardial infarction was created in mice by coronary artery ligation as previously described (13). Hearts were harvested from mice 1 and 3 days after coronary artery ligation followed by perfusion fixation of the heart with Z-Fix (Anatech LTD). Hearts were then immersion fixed in Z-Fix overnight at 4° C. After dehydration in graded ethanol solutions, hearts were placed in Histo-Clear (National Diagnostics) and paraffin-embedded. Five micron tissue sections were deparaffinized, rehydrated, incubated with 3% hydrogen peroxide, rinsed in water followed by phosphate buffered saline. Sections were blocked, incubated in 1:50 anti-mouse ST2 primary antibody (Morwell Diagnostics) and 1:100 anti-rat HRP conjugated secondary antibody (Vector Laboratories). Slides were counterstained with hemotoxylin and eosin.

Patient studies and ELISA for ST2.

HEART study The Healing and Early Afterload Reducing Therapy (HEART) study was a randomized, double-blind, placebo-controlled trial that enrolled 352 patients with acute myocardial infarction (MI) from 36 centers in the United States and Canada. Men and women over the age of 21 years who had experienced an MI within 24 hours were eligible. Inclusion and exclusion criteria, and details of the trial design have been previously described (Pfeffer M. A., et al., *Circu-* lation, 1997, 95:2643-2651; Greaves S. C., et al., *Am. J. Cardiol*, 1997, 80:442-448; Solomon S. D., et al., *Ann. Intern. Med.*, 2001, 134:451-458; Aikawa Y., et al., *Am. Heart J*, 2001, 141:234-242). Serial blood samples from days 1, 14, and 90 after myocardial infarction from 69 randomly chosen patients in the HEART trial were available for this study. Soluble T1/ST2 was assayed with a double monoclonal sandwich ELISA assay that has been previously described (Kuroiwa K., et al., *Hybridoma*, 2000, 19:151-159). The assay is commercially available (MBL International, Watertown, Mass.).

PRAISE study The Prospective Randomized Amlodipine Survival Trial (PRAISE) study was a prospective large-scale study of amlodipine in patients with heart failure due to coronary artery disease. The results of this trial were null for a benefit of Amlodipine in severe heart failure. Blood samples were drawn at the beginning of this study before therapy and then twice more during the study. Soluble T1/ST2 was assayed as described above. One of the key current blood tests for heart failure is brain natriuretic peptide (BNP). We examined whether T1/ST2 levels in heart failure patients were altered and whether T1/ST2 levels correlated with BNP levels in these patients.

Statistics. Each in vitro experiment shown was performed a minimum of three times. Values are means±SEM. Data were analyzed by one-way ANOVA, or ANOVA for repeated measures, with post hoc Bonferroni multiple comparison analyses where appropriate. Linear regression was performed on serum values with log transformed values due to non-normal parameter distributions. P values <0.05 were considered statistically significant.

Figure 11:
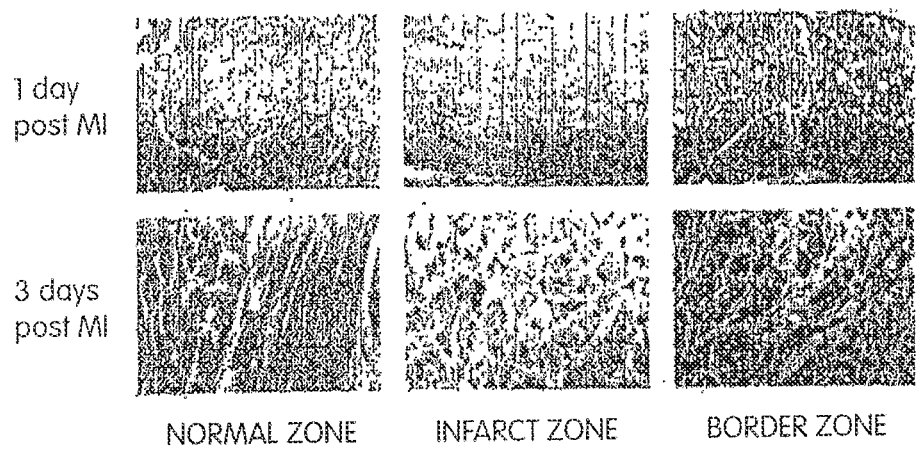
FIG. 11 shows expression of T1/ST2 protein following myocardial infarction in mice by immunohistochemistry at 1 day but not 3 days after infarction. 40× magnification.

Results:

In vivo Expression of T1/ST2 Protein in Myocardial Infarction in Mice. To evaluate expression of T1/ST2 in injured myocardium, mice were subjected to experimental myocardial infarction through coronary artery ligation. FIG. 11 shows protein expression of T1/ST2 using immunohistochemistry in mouse hearts 1 and 3 days post myocardial infarction. Positive staining was seen 1 day post myocardial infarction (post-MI) in all regions of the left ventricle, normal, infarct and border zones, but not at 3 days post myocardial infarction. No staining for T1/ST2 was observed in 1 and 3 day sham-operated controls. These results suggest that T1/ST2 protein is expressed in response to acute injury during the early phase of post-infarction remodeling before the migration of macrophages into the infarct and border zones seen at 3 days. The monoclonal antibody used for these studies does not distinguish between soluble and membrane forms of T1/ST2.

Soluble T1/ST2 is increased in the systemic circulation of patients one day after myocardial infarction. Since soluble T1/ST2 is highly induced in cardiac myocytes, and T1/ST2 protein is highly expressed in mouse myocardium following experimental myocardial infarction, we hypothesized that soluble T1/ST2 is increased in the systemic circulation of patients following myocardial infarction.

Figure 12A:
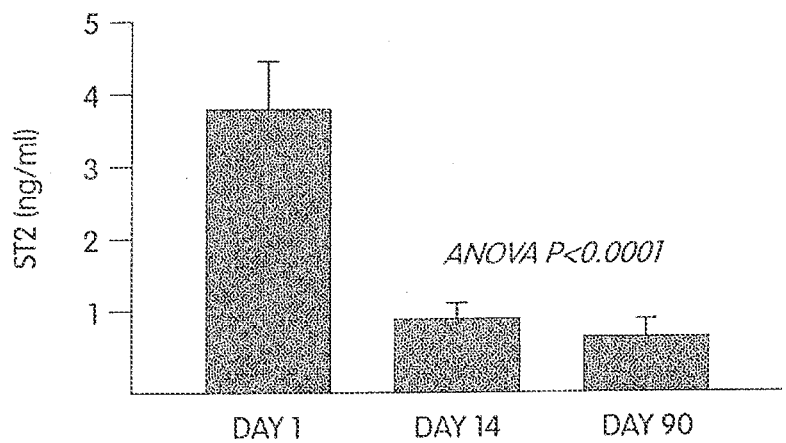
FIG. 12 shows in graphical form ST2 protein levels in the systemic circulation of human patients post myocardial infarction; a. ST2 protein was significantly increased on day 1 post myocardial infarction compared to day 14 and day 90; b. Linear regression analysis demonstrating a significant positive relationship (p<0.001) between circulating ST2 protein and creatine kinase 1 day post myocardial infarction. Log ST2=0.454(log CK)−1.07; c. Quartile analysis of circulating ST2 protein levels day 1 post myocardial infarction and ejection fraction. Low ejection fraction is associated with high ST2 protein levels; d. Linear regression analysis demonstrating the relationship between ST2 and ejection fraction.
Figure 12B:
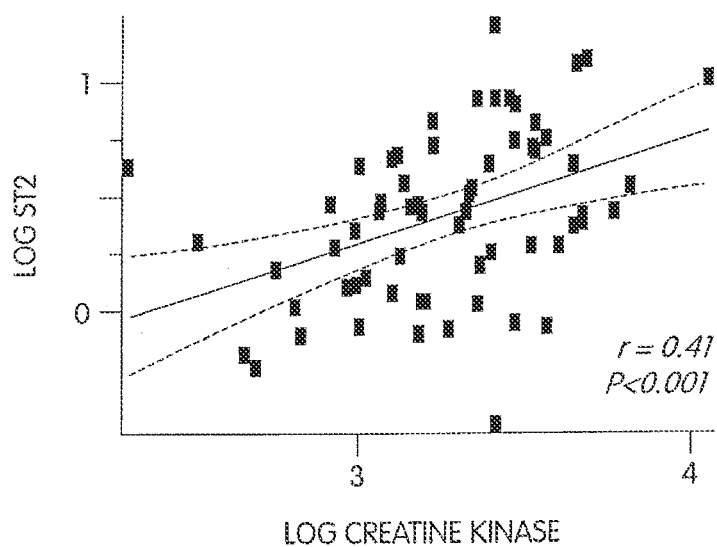
Figure 12C:
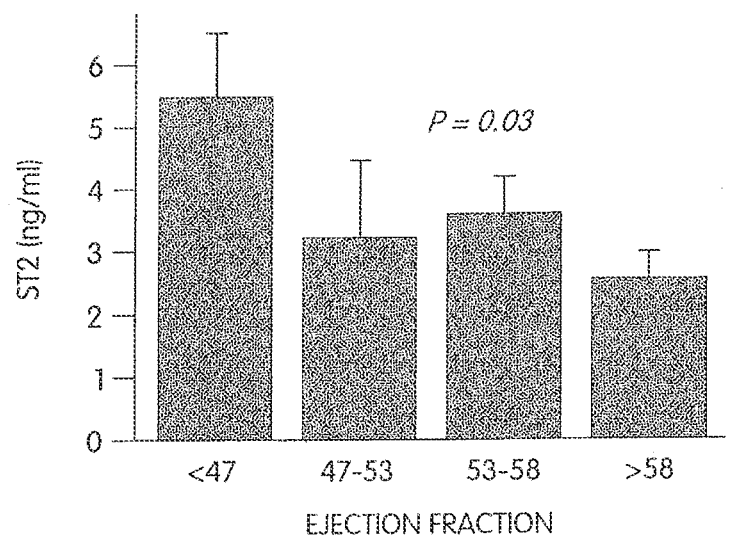
Figure 12D:
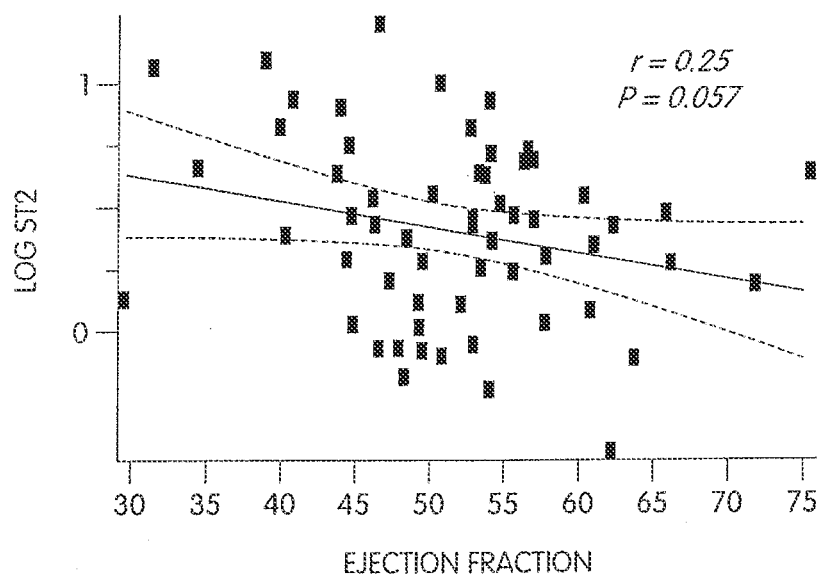

Methods and Results: Using a double monoclonal sandwich ELISA assay, we assayed blood samples from 69 participants of the HEART Study on the day of myocardial infarction (day 1), as well as day 14 and day 90 after infarction. As shown in FIG. 12*a*, systemic T1/ST2 protein was significantly increased one day after myocardial infarction (mean±SEM, 3.8±0.4 ng/ml, p<0.001; range, 0.32 to 17.42 ng/ml) compared to day 14 (mean±SEM, 0.98±0.06 ng/ml; range, 0.25 to 3.42 ng/ml) and day 90 (mean±SEM, 0.79±0.07 ng/ml; range, 0.02 to 3.53 ng/ml; day 14 vs. day 90, P=NS). Mean values at day 90 were similar to published mean values for healthy controls (Kuroiwa K., et al., *Hybridoma*, 2000, 19:151-159). Systemic T1/ST2 protein levels correlated positively with peak creatine kinase levels (r=0.41, p<0.001), shown in FIG. 12*b*. High systemic ST2 protein levels were also associated with low ejection fraction one day after myocardial infarction as shown in quartile analysis (p=0.03) in FIG. 12*c*.

Conclusions: These results suggest a coordinated regulation between the extent of myocardial injury and synthesis and secretion of soluble T1/ST2 into the systemic circulation in the clinical setting of myocardial infarction.

Soluble T1/ST2 is increased in the systemic circulation of patients with severe chronic heart failure. This study tested the hypothesis that soluble T1/ST2 levels in the serum of patients with severe chronic heart failure are associated with levels of BNP, ProANP and norepinephrine, neurohormones that are increased in heart failure.

Methods and Results: Serum samples, clinical variables and neurohormone levels from the neurohormone substudy of the Prospective Randomized Amlodipine Survival Evaluation 2 study (PRAISE-2) heart failure trial (New York Heart Association functional class III or IV, end point: mortality or transplantation) were used. The PRAISE-2 study was a multicenter, randomized, double blinded, parallel group, placebo-controlled study to evaluate the effects of amlodipine 10 mg/day on survival in patients with congestive heart failure of a non-ischemic etiology. The trial consisted of—patients recruited from 240 sites in the United States and Canada. The neurohormone substudy consisted of 181 patients recruited from 26 centers participating in the main study. Both the main PRAISE-2 and the neurohormonal substudy were approved by the institutional review boards of the participating institutions. Patients were eligible if they were at least 18 years of age, had heart failure of a non-ischemic etiology, symptoms at rest or upon minimal exertion (New York Heart Association functional class III or IV) and a left ventricular ejection fraction lower than 30%. All patients were on treatment with ACE inhibitors and digoxin for at least 3 months. Patients were excluded if they had a recent or remote history of angina.

Assays for T1/ST2, Neurohormones and Measurement of Oxidative Stress. Blood samples were evaluated at baseline and 2 weeks (Table 1). Soluble T1/ST2 was measured with a sandwich double monoclonal antibody ELISA method (Medical & Biological Laboratories Co., Ltd., Nagoya, Japan) according to the manufacturer's instruction. In brief, serum samples or standards were incubated in the microwells coated with anti-human T1/ST2 antibody. After washing, peroxidase-conjugated anti-human T1/ST2 antibody was added into the microwell and incubated. After another washing, the peroxidase substrate was added and the optical density at 450 nm was determined. Circulating catecholamines (norepinephrine, epinephrine, dopamine), angiotensin II, natriuretic peptides (pro-atrial natriuretic peptide (Pro-ANP), brain natriuretic peptide (BNP)) and indices of oxidative stress (malondialdehyde, adrenolutin) were measured as previously described (Dhalla K S, et al., *Mol Cell Biochem*, 1989; 87:85-92; Moe G W, et al., *Am Heart J*, 2000; 139:587-95). T1/ST2 serum measurements were performed on samples from 162 patients obtained at trial enrollment and from 135 of the same patients obtained 2 weeks after trial enrollment. Baseline T1/ST2 levels correlated with baseline BNP levels (r=0.3511, p<0.0001), baseline ProANP levels (r=0.3598, p<0.0001) and baseline norepinephrine levels (r=0.3854, p<0.0001) (Table 2). The change in T1/ST2 (T1/ST2 levels at 2 weeks minus T1/ST2 levels at trial enrollment) was significant as a univariate predictor of mortality or transplantation (p=0.048) as was baseline BNP (p<0.0001) and baseline ProANP ($p<0.0001$) (Table 3). In multivariate models including BNP and ProANP, the change in T1/ST2 remained significant as an independent predictor of mortality or transplantation independent of BNP and ProANP (Table 4).

TABLE 1

Baseline Characteristics

|  | N | Median | 5th Percentile | 95th Percentile |
|---|---|---|---|---|
| A. All Patients | | | | |
| Baseline ST2 (ng/mL) | 161 | 0.24 | 0.16 | 0.70 |
| Baseline BNP (pmol/L) | 162 | 56.0 | 3.70 | 264.30 |
| Baseline ProANP (pg/L) | 162 | 1778.50 | 531.00 | 5615.00 |
| Norepinephrine (pg/mL) | 158 | 401.58 | 165.90 | 1096.00 |
| Dopamine (pg/mL) | 158 | 39.06 | 4.22 | 398.40 |
| Epinephrine (pg/mL) | 158 | 54.92 | 11.64 | 139.90 |
| Angiotensin II (pg/mL) | 157 | 22.60 | 7.00 | 67.30 |
| Adrenolutin (ng/mL) | 156 | 22.84 | 4.31 | 369.31 |
| Creatinine (mmol/L) | 158 | 1.10 | 0.80 | 1.90 |
| Age (years) | 157 | 59.9 | 32.5 | 78.2 |
| Body Mass Index (kg/mm2) | 157 | 27.6 | 20.4 | 39.7 |
| LV Ejection Fraction | 158 | 22.0 | 11.0 | 30.0 |
| B. Patients With Blood Samples at Baseline and Week 2 | | | | |
| Baseline ST2 (ng/mL) | 135 | 0.24 | 0.15 | 0.81 |
| Baseline BNP (pmol/L) | 135 | 54.90 | 3.30 | 264.30 |
| Baseline ProANP (pg/L) | 135 | 1788.00 | 488.00 | 4788.00 |
| Norepinephrine (pg/mL) | 130 | 395.05 | 171.70 | 1118.00 |
| Dopamine (pg/mL) | 130 | 64.02 | 4.32 | 405.50 |
| Epinephrine (pg/mL) | 130 | 56.07 | 12.24 | 134.80 |
| Angiotensin II (pg/mL) | 131 | 21.70 | 7.00 | 58.30 |
| Adrenolutin (ng/mL) | 130 | 24.41 | 4.43 | 369.31 |
| Creatinine (mmol/L) | 135 | 1.10 | 0.80 | 2.00 |
| Age (years) | 134 | 60.5 | 34.4 | 78.2 |
| Body Mass Index (kg/mm2) | 134 | 27.4 | 20.5 | 39.7 |
| LV Ejection Fraction | 135 | 22.0 | 11.0 | 30.0 |

TABLE 2

Relation of ST2 to Clinical Variables and Neurohormones: Spearman Correlations

|  |  | Baseline ST2 | Change in ST2 |
|---|---|---|---|
| Baseline BNP (pmol/L) | R | 0.3511 | −0.11327 |
|  | p value | <0.0001 | 0.1843 |
|  | N | 161 | 139 |
| Baseline ProANP (pmol/L) | R | 0.35979 | −0.10967 |
|  | p value | <0.0001 | 0.1987 |
|  | N | 161 | 139 |
| Change in BNP* (pmol/L) | R | −0.10184 | 0.21497 |
|  | p value | 0.2329 | 0.0110 |
|  | N | 139 | 139 |
| Change in ProANP* (pmol/L) | R | 0.05584 | 0.28847 |
|  | p value | 0.5138 | 0.0006 |
|  | N | 139 | 139 |
| Norepinephrine (pg/ml) | R | 0.38535 | −0.25253 |
|  | p value | <0.0001 | 0.0032 |
|  | N | 156 | 134 |
| Dopamine (pg/mL) | R | 0.07879 | 0.22127 |
|  | p value | 0.3283 | 0.0102 |
|  | N | 156 | 134 |
| Epinephrine (pg/mL) | R | 0.08043 | −0.12110 |
|  | p value | 0.3182 | 0.1634 |
|  | N | 156 | 134 |
| Angiotensin II (pg/mL) | R | 0.00374 | −0.00725 |
|  | p value | 0.9630 | 0.9335 |
|  | N | 156 | 135 |
| Adrenolutin (ng/mL) | R | 0.00544 | −0.10422 |
|  | p value | 0.9464 | 0.2308 |
|  | N | 155 | 134 |
| Creatinine (units) | R | 0.16567 | 0.02513 |
|  | p value | 0.0388 | 0.7724 |
|  | N | 156 | 135 |
| LV Ejection Fraction | R | −0.08006 | 0.03651 |
|  | p value | 0.3205 | 0.6742 |
|  | N | 156 | 135 |
| Age (years) | R | −0.11768 | 0.19260 |
|  | p value | 0.1447 | 0.0274 |
|  | N | 155 | 134 |
| Body Mass Index (units) | R | 0.04561 | −0.05410 |
|  | p value | 0.5731 | 0.5347 |
|  | N | 155 | 134 |

R, Spearman correlation coefficient;
N, sample number.
Baseline, values at trial enrollment;
*Change, values at week 2 minus values at trial enrollment.

TABLE 3

Univariate Predictors of Mortality and Transplantation (Endpoint)

| Variable | Odds Ratio | 95% confidence interval | p-value |
|---|---|---|---|
| Baseline ST2, per 0.1 ng/mL | 1.114 | 0.961-1.300 | 0.1509 |
| Baseline BNP, per 10 pmol/L | 1.106 | 1.060-1.161 | <0.0001 |
| Baseline ProANP, per 10 pg/L | 1.007 | 1.005-1.010 | <0.0001 |
| Change in ST2*, per change of 0.1 ng/mL | 1.320 | 1.042-1.827 | 0.0482 |
| Change in BNP*, per change of 10 pmol/L | 1.033 | 0.966-1.110 | 0.3401 |
| Change in ProANP*, per change of 10 pg/L | 1.003 | 0.997-1.009 | 0.3413 |
| Norepinephrine, per 1 pg/mL | 1.001 | 1.000-1.002 | 0.0562 |
| Dopamine, per 10 pg/mL | 1.029 | 1.006-1.059 | 0.0433 |
| Epinephrine, per 1 pg/mL | 0.999 | 0.995-1.001 | 0.6645 |
| Angiotensin II, per 1 pg/mL | 0.997 | 0.977-1.017 | 0.7921 |
| Adrenolutin, per 10 ng/mL | 0.985 | 0.943-1.017 | 0.4167 |
| Creatinine, per 1 mmol/L | 2.487 | 0.997-6.417 | 0.0526 |
| LV Ejection Fraction | 0.952 | 0.897-1.007 | 0.0906 |
| Race | 1.947 | 0.946-4.192 | 0.0776 |
| Gender | 1.225 | 0.576-2.728 | 0.6061 |
| Age | 1.435 | 1.099-1.914 | 0.0104 |
| Etiology | 1.543 | 0.744-3.336 | 0.2543 |
| Body Mass Index, per 1 $kg/mm^2$ | 0.972 | 0.919-1.021 | 0.2876 |

Baseline, values at trial enrollment;
*Change, values at week 2 minus values at trial enrollment.

TABLE 4

Multivariate Predictors of Mortality and Transplantation (Endpoint): Predictive Value of ST2

| Variables | p |
|---|---|
| Baseline ST2 and Baseline BNP | |
| Baseline BNP | 0.0003 |
| Baseline Dopamine | 0.0906 |
| Baseline ST2 | 0.6368 |
| Baseline ST2 and Baseline ProANP | |
| Baseline ProANP | <0.0001 |
| Baseline Dopamine | 0.0944 |
| Baseline ST2 | 0.3306 |

TABLE 4-continued

Multivariate Predictors of Mortality and Transplantation (Endpoint): Predictive Value of ST2

| Variables | p |
|---|---|
| Change in ST2* and Baseline BNP | |
| Baseline BNP | 0.0001 |
| Change in ST2 | 0.0392 |
| Change in ST2* and Baseline ProANP | |
| Baseline ProANP | <0.0001 |
| Change in ST2 | 0.0274 |

Baseline, values at trial enrollment;
*Change, values at week 2 minus values at trial enrollment.

Example 3

Methods

Study populations. The Thrombolysis in Myocardial Infarction (TIMI) 14 trial was a randomized, open-label, dose-ranging study of combination reperfusion therapy for patients with ST-segment elevation MI conducted between March 1997 and July 1998. Specifically, this study was an angiographic trial comparing 4 different thrombolytic combinations: abciximab alone, alteplase alone, abciximab with reduced dose of alteplase, and abciximab with reduced dose of streptokinase (Antman E M et al., Circulation, 1999; 99:2720-32; Antman E M et al., Eur Heart J, 2000; 21:1944-53). The ENTIRE-TIMI 23 trial was an open-label, dose-ranging, multicenter study conducted between February 2000 and September 2001 to evaluate enoxaparin as adjunctive antithrombin therapy with various forms of pharmacological reperfusion, including full-dose tenecteplase and half-dose tenecteplase plus abciximab (Antman E M et al., Circulation. 2002; 105:1642-9). In both studies, patients were eligible for inclusion if they had a qualifying episode of ischemic discomfort of at least 30 min within 6 hr (ENTIRE) or 12 hr (TIMI 14), and exhibited at least 0.1 mV ST-segment elevation in 2 contiguous precordial electrocardiographic leads. Exclusion criteria for both trials included increased risk of hemorrhage, severe renal insufficiency, and cardiogenic shock.

Laboratory analyses. Serum samples collected at baseline, 1, 3, 12, and 24 hr after enrollment in TIMI 14 were evaluated. Serum samples from the ENTIRE trial were available only at baseline. Serum was isolated within 60 min of sample collection and stored at −20° C. or colder until shipped to the TIMI Biomarker Core Lab (Boston, Mass.), where samples were maintained at −70° C. Soluble ST2 was measured with a sandwich double monoclonal antibody ELISA method (Medical & Biological Laboratories Co., Ltd., Nagoya, Japan). Serum samples or standards were incubated in microwells coated with anti-human ST2 antibody. After washing, peroxidase-conjugated anti-human ST2 antibody was added into the microwell and incubated. After washing again, the peroxidase substrate was added and the optical density at 450 nm was determined High sensitivity C-reactive protein (hs-CRP, Dade-Behring Inc, Deerfield, Ill.), creatine kinase MB isoenzyme (CK-MB), B-type natriuretic peptide (SHIONORIA BNP, Shionogi, Osaka, Japan). and cardiac troponin I (ACS:180, Bayer Diagnostics, Tarrytown, N.Y.) were measured using previously described methods (Morrow D A et al., *J Am Coll Cardiol.* 1998; 31:1460-5; Morrow D A et al., *Clin Chem.* 2000; 46:453-460). Creatine kinase isoenzyme levels were measured locally at the site on admission, at 3 hours, and at 6 to 8 hour intervals for the first 24 hours. Due to sample availability, BNP levels were measured in samples from ENTIRE-TIMI 23, but not TIMI 14.

Statistical analysis. Patients were divided into quartiles on the basis of their ST2 serum levels at the time of enrollment into the studies. ST2 levels are described using the median and $25^{th}$-$75^{th}$ percentiles. The association between baseline clinical characteristics and quartiles of ST2 were analyzed using the Kruskal-Wallis test for continuous variables and the $\chi^2$ test for categorical variables. Correlations between ST2 and other continuous baseline variables were studied with a non-parametric (Spearman's) correlation coefficient. For evaluation of association with clinical outcomes, ST2 was compared between patients who met a study end point and those who did not using the Wilcoxon rank-sum test. Multivariable analysis of the association of ST2 with outcomes was performed using logistic regression including terms for established predictors of mortality in ST-elevation myocardial infarction (STEMI) (Morrow, D A et al., Circulation 2000; October 24; 102(17):2031-7). Except where stated, results presented are for the combined TIMI 14 and ENTIRE-TIMI 23 study population.

Results

Baseline ST2 and Clinical Variables. Most baseline clinical characteristics, including gender, age, weight, and extent of coronary artery disease did not correlate with baseline ST2 levels (Table 5). Few patients in this population had either a prior history or presented with clinical evidence of heart failure. Interestingly, heart rate correlated positively with ST2 levels (p<0.0001) and systolic blood pressure showed a modest correlation with ST2 levels (p=0.05), consistent with the theory that ST2 is secreted by cardiac myocytes under biomechanical stress. The biomarkers cardiac troponin I, BNP, and CRP—which have all been shown to predict outcome after myocardial infarction (de Lemos J A et al., N Engl J Med 2001; 345:1014-21; Antman E M et al, N Engl J Med 1996; 335:1342-9; Morrow D A et al., J Am Coll Cardiol 1998; 31:1460-5) were correlated with ST2 by quartile analysis and cardiac troponin I and CRP were statistically significant. When these biomarkers were evaluated as continuous variables, quantitatively weak correlations were observed (Table 6).

TABLE 5

Baseline Clinical Characteristics According to Quartiles of ST2 (ng/mL)

| | Quartile 1 | Quartile 2 | Quartile 3 | Quartile 4 | p trend | p Q4 vs Q1 |
|---|---|---|---|---|---|---|
| Range, ng/mL | 0.085-0.179 | 0.180-0.235 | 0.236-0.346 | 0.347-6.88 | | |
| n | 204 | 202 | 202 | 202 | | |
| Time CP to randomization (hrs) | 2.8 ± 1.6 | 3.1 ± 1.5 | 3.2 ± 1.4 | 4.0 ± 1.9 | <0.0001 | <0.0001 |
| Age (years) | 58 ± 10 | 58 ± 10 | 58 ± 11 | 58 ± 10 | 0.9 | 1.0 |
| Male | 74% | 77% | 85% | 81% | 0.03 | 0.09 |
| White | 88% | 89% | 90% | 88% | 0.9 | 1.0 |

TABLE 5-continued

Baseline Clinical Characteristics According to Quartiles of ST2 (ng/mL)

|  | Quartile 1 | Quartile 2 | Quartile 3 | Quartile 4 | p trend | p Q4 vs Q1 |
|---|---|---|---|---|---|---|
| Past Medical History |  |  |  |  |  |  |
| Hypertension | 25% | 24% | 36% | 33% | 0.02 | 0.09 |
| Congestive Heart Failure | 0% | 0% | 1.5% | 1.0% | 0.1 | 0.2 |
| Angina | 26% | 24% | 26% | 32% | 0.3 | 0.2 |
| Diabetes | 14% | 14% | 15% | 16% | 0.9 | 0.5 |
| Family history of CAD | 73% | 73% | 73% | 73% | 0.2 | 0.08 |
| Hypercholesterolemia | 22% | 21% | 21% | 29% | 0.2 | 0.1 |
| Smoking status: |  |  |  |  |  |  |
| Current smoker | 57% | 48% | 49% | 48% | 0.2 | 0.06 |
| Physical findings |  |  |  |  |  |  |
| Weight kg | 83 ± 16 | 81 ± 15 | 82 ± 14 | 83 ± 15 | 0.4 | 0.8 |
| Systolic BP (mm Hg) | 139 ± 21 | 138 ± 22 | 141 ± 23 | 143 ± 22 | 0.1 | 0.05 |
| HR (BPM) | 71 ± 17 | 75 ± 17 | 72 ± 16 | 80 ± 17 | 0.001 | <0.0001 |
| Killip Class II-IV | 2.0% | 1.5% | 3.6% | 4.5% | 0.3 | 0.2 |
| Diagnostic Testing |  |  |  |  |  |  |
| cTnI >0.1 ng/ml* | 61% | 69% | 77% | 84% | 0.001 | <0.0001 |
| BNP >80 pg/ml* | 1.8% | 5.4% | 7.2% | 14.4% | 0.003 | 0.001 |
| CRP >1.5 ng/ml | 2.1% | 8.8% | 8.1% | 11.4% | 0.006 | <0.0001 |
| Creatinine mg/dL | 1.0 ± 0.21 | 1.0 ± 0.20 | 1.0 ± 0.25 | 1.1 ± 0.28 | 0.1 | 0.03 |
| Extent CAD (50% stenosis) |  |  |  |  | 0.3 | 0.2 |
| 1 vessel | 48% | 55% | 45% | 50% |  |  |
| 2 vessel | 38% | 28% | 34% | 30% |  |  |
| 3 vessel | 15% | 18% | 20% | 20% |  |  |
| EF (%)** | 58 ± 15 | 58 ± 15 | 57 ± 15 | 57 ± 15 | 1.0 | 0.9 |

CP = Chest Pain;
HR = Heart Rate;
cTnI = Cardiac Troponin I;
BNP = B type Natriuretic Peptide;
CRP = C Reactive Protein;
CAD = Coronary Artery Disease;
EF = Ejection Fraction
*Measured in the ENTIRE-TIMI 23 population only;
N = 448 except ** (N = 469)

TABLE 6

Correlation between ST2 and Continuous Variables

| Variable | Spearmans rho | P value |
|---|---|---|
| Time CP to randomization | 0.29 | <0.0001 |
| Age | −0.003 | 0.9 |
| Weight (kg) | 0.01 | 0.8 |
| CKMB peak | 0.08 | 0.02 |
| cTnI* | 0.26 | <0.0001 |
| CRP | 0.10 | 0.007 |
| BNP* | 0.068 | 0.15 |
| Creatinine | 0.09 | 0.01 |
| LVEF** | −0.005 | 0.9 |

CP = Chest Pain;
CKMB = MB isoenzyme of creatine kinase;
cTnI = Cardiac Troponin I;
BNP = B type Natriuretic Peptide;
CRP = C Reactive Protein;
CAD = Coronary Artery Disease;
EF = Ejection Fraction.
*Measured in the ENTIRE-TIMI 23 population only; N = 448 except
**(N = 469)

Figure 13:
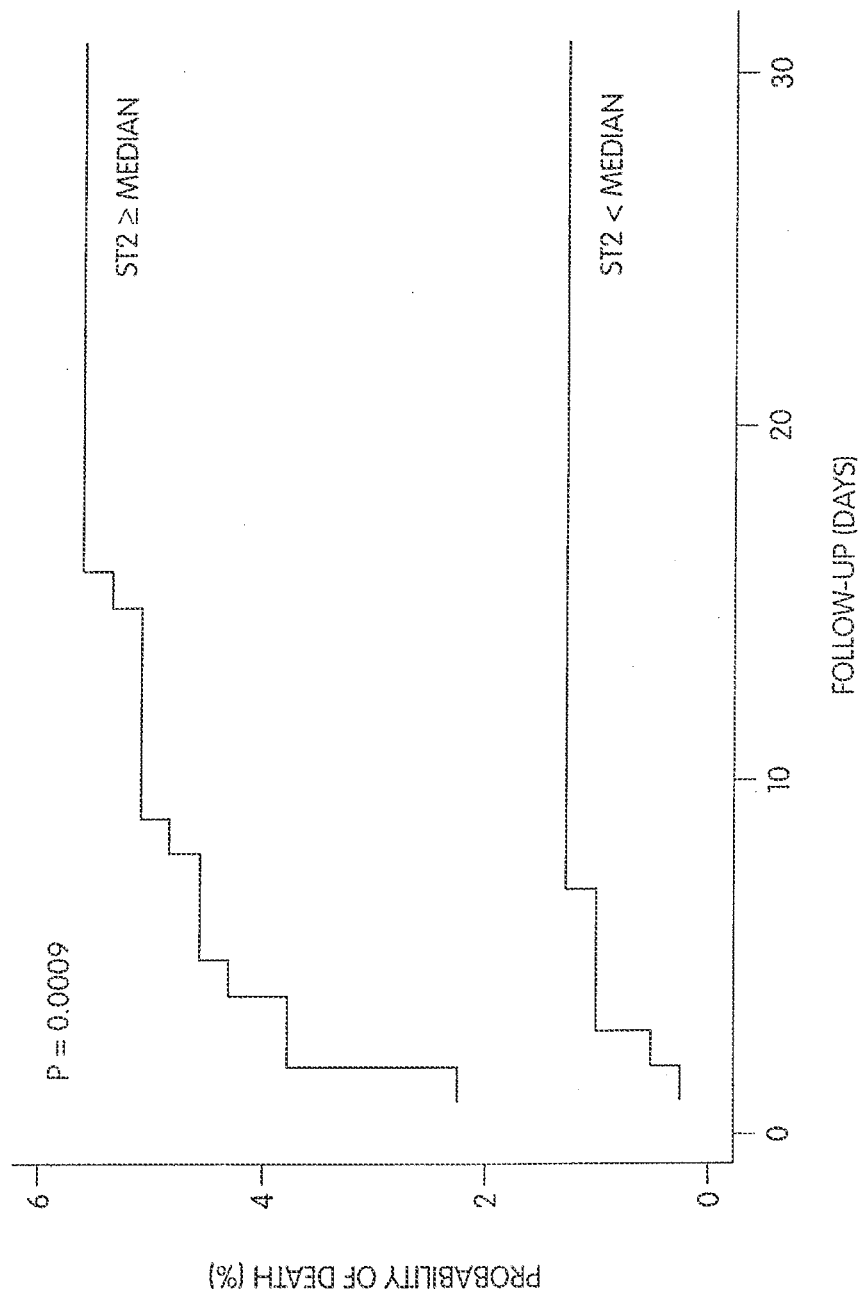
FIG. 13 shows that elevated baseline levels of ST2 were indicative of higher mortality through 30 days of follow-up (log-rank, p=0.0009).

ST2 and Clinical Outcomes. For the combined cohort of 810 patients, baseline ST2 was significantly associated with clinical outcomes at 30 days (Table 7). Specifically, levels of ST2 were significantly higher at presentation among patients who subsequently died (p=0.0001), or developed new or worsening CHF (p=0.009), by 30 days after enrollment. Dichotomized at the median, elevated baseline levels of ST2 were indicative of higher mortality through 30 days of follow-up (log-rank, p=0.0009, FIG. 13). Moreover, in an analysis by quartiles of ST2, the risk of both death (p=0.001) and the composite of death or CHF (p=0.001) increased in a graded, stepwise fashion with higher levels of ST2. This association between ST2 and clinical events was homogeneous between the two individual trials (TIMI 14 and ENTIRE-TIMI 23).

TABLE 7

Association between Baseline ST-2 Concentration (ng/ml) and Outcomes

| Outcome (30 days) | n | Median [25, 75] | p value |
|---|---|---|---|
| Dead | 28 | 0.379 [0.267, 0.611] | 0.0001 |
| Alive | 782 | 0.233 [0.178, 0.340] |  |
| MI | 29 | 0.213 [0.171, 0.259] | 0.11 |
| No MI | 781 | 0.237 [0.181, 0.348] |  |
| CHF | 21 | 0.287 [0.237, 0.470] | 0.009 |
| No CHF | 789 | 0.233 [0.178, 0.345] |  |
| Death/CHF | 47 | 0.317 [0.246, 0.590] | <0.0001 |
| No Death/CHF | 763 | 0.231 [0.177, 0.339] |  |

MI = Myocardial Infarction;
CHF = Congestive Heart Failure

Evolution of ST2 serum levels. Baseline ST2 levels analyzed by quartile were significantly correlated with the time to randomization (Tables 5 and 6). ST2 levels were anticipated to increase in the first day following coronary occlusion and return to normal over the next 14 days (6). Among the TIMI 14 patients, analysis of serial measurements of serum ST2 in 228 patients revealed an increase with time, with most patients reaching a peak ST2 level at 12 hours, although, a few patients had ST2 serum levels that continued to increase past this time point.

Multivariate analysis. After controlling for established clinical predictors in STEMI including age, heart rate, systolic blood pressure, location of myocardial infarction, Killip class, and time from onset of chest pain, increasing levels of ST2 remained an independent predictor of death at 30 days (OR1.77; 95% CI 1.01-3.12, p=0.047). This association was no longer significant when BNP was added to the clinical model (assessment was limited to ENTIRE). The predictive capacity of ST2 ascertained at later time points (3 and 12 hours in TIMI 14) was also evaluated; revealing a stronger association between ST2 and mortality risk.

Serum soluble T1/ST2, therefore is a novel biomarker for severe heart failure that parallels neurohormonal activation. In patients with severe chronic NYHA Class III-IV heart failure, the change in T1/ST2 levels is an independent predictor of the endpoint of mortality or transplantation.

In this study, we explored the potential role of serum measurement of a recently-identified receptor of the interleukin-1 family in acute myocardial infarction. The soluble form of this receptor is rapidly secreted by cardiac myocytes when the cells are biomechanically overloaded; this suggests that the receptor may play a role in conditions where the myocardium is rapidly overloaded, such as in myocardial infarction. To explore this, we measured serum ST2 levels at the time of presentation in a cohort of patients with acute myocardial infarction. The results demonstrate that ST2 levels at the time of presentation in these patients are associated with in-hospital and 30-day mortality. Furthermore, multivariate analysis indicated that ST2 level is independently associated with outcome after controlling for important clinical factors.

Thus, the significance of these data is twofold. Foremost, these data suggest that the interleukin receptor family, which participates in host defense and differentiation of T cells (Sims JE. IL-1 and IL-18 receptors, and their extended family. *Curr Opin Immunol.* 2002; 14:117-22), may participate in early events in acute myocardial infarction. These data implicate this receptor as a potential novel target for modifying prognosis in patients with myocardial infarction. Secondarily, ST2 represents a novel biomarker that offers prognostic information in patients with acute myocardial infarction; thus, extending upon our prior work demonstrating an association between ST2 and mortality among patients with non-ischemic congestive heart failure (Weinberg E O, Shimpo M, Hurwitz S, Tominaga S, Rouleau J L, Lee R T. Identification of serum soluble ST2 receptor as a novel heart failure biomarker. *Circulation.* 2003; 107:721-6), another condition of myocardial overload.

Although not excluded, it is unlikely that the relationship of ST2 and outcome after myocardial infarction is simply a reflection of the association of chronic elevations in inflammatory markers like CRP and risk of myocardial infarction. ST2, like BNP, may be synthesized by cardiac myocytes themselves and data from patients without apparent ischemic disease suggests that ST2 predicts prognosis in the absence of coronary artery disease. Furthermore, preliminary data suggest that ST2 levels in outpatients with stable coronary artery disease are unrelated to CRP levels. While our data support the complementary value of ST2 for risk assessment when added to a robust clinical model (REF TIMI Risk Score), ST2 did not contribute additional information to BNP in the smaller data set limited to ENTIRE-TIMI 23. There may also be prognostic value of ST2 in conjunction with other available biomarkers.

Although ST2 may be secreted by mechanically-overloaded cardiac myocytes, many cells can secrete ST2. It is therefore possible that elevations in serum ST2 are not completely specific for acute myocardial infarction. In addition to non-ischemic heart failure (Weinberg E O, Shimpo M, Hurwitz S, Tominaga S, Rouleau J L, Lee R T. Identification of serum soluble ST2 receptor as a novel heart failure biomarker. *Circulation.* 2003; 107:721-6), patients with asthma (Oshikawa K, Kuroiwa K, Tago K, Iwahana H, Yanagisawa K, Ohno S, Tominaga S I, Sugiyama Y. Elevated soluble ST2 protein levels in sera of patients with asthma with an acute exacerbation. *Am J Respir Crit Care Med.* 2001; 164:277-81) or autoimmune diseases like systemic lupus erythematosus (Kuroiwa K, Arai T, Okazaki H, Minota S, Tominaga S. Identification of human ST2 protein in the sera of patients with autoimmune diseases. *Biochem Biophys Res Commun.* 2001; 284:1104-8) may also have increased serum ST2 levels. Therefore, the usefulness of ST2 measurement in the initial diagnosis of acute myocardial infarction in such subjects is not unequivocal.

However, ST2 remains a possible target for therapy in patients with MI. These data demonstrate how genomic technology can reveal a new potential pathophysiological pathway in a common disease. ST2 was initially identified through studies of the interleukin-1 family, but its role in myocardial disease was only recently suggested by genomic studies with DNA microarrays. Studies with DNA microarrays allow identification of potential new disease pathways, but this is only an initial step in understanding the role of the pathway. The above data supports the role for ST2 in acute myocardial infarction, since the levels of ST2 predict outcome. Studies of the function of ST2 in myocardial infarction are possible. In addition, identifying the ligand for the soluble and membrane ST2 receptors could help further the understanding of the potentially competing roles of the membrane and soluble receptors.

The results described establish that the T1/ST2 is secreted during a heart attack and/or heart failure, and can be easily measured, thereby supporting the asserted utilities of the invention.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is:

1. A method for selecting a treatment for a cardiovascular disorder for a subject, and treating the subject, the method comprising:
performing an assay to determine a level of soluble ST2 in a biological sample from a subject having or at risk of developing a cardiovascular disorder;
identifying a subject that has an elevated level of soluble ST2 relative to a control;
selecting a treatment for a cardiovascular disorder for the identified subject; and
administering a therapeutically effective amount of a treatment for a cardiovascular disorder to the identified subject.

2. The method of claim 1, wherein the biological sample is blood or serum.

3. The method of claim 1, wherein the assay is performed using an antibody or an antibody fragment that specifically binds to soluble ST2.

4. The method of claim 1, wherein the control is a predetermined value.

5. The method of claim 1, wherein the control is a level of soluble ST2 in a healthy subject.

6. The method of claim 1, wherein the treatment is acute treatment.

7. The method of claim 1, wherein the treatment is prophylactic treatment.

8. The method of claim 1, wherein the treatment comprises an agent selected from the group consisting of: anti-inflammatory agents, anti-thrombotic agents, anti-coagulants, anti-platelet agents, fibrinolytic agents, lipid-reducing agents, direct thrombin inhibitors, glycoprotein IIb/IIIb receptor inhibitors, calcium channel blockers, beta-adrenergic receptor blockers, cyclooxygenase-2 inhibitors, renin-angiotensin (RAS) system inhibitors, and anti-hypertensive agents.

9. The method of claim 8, wherein the renin-angiotensin system inhibitor is selected from the group consisting of: an angiotensin-converting enzyme (ACE) inhibitor, an angiotensin II receptor blocker (ARB), an agent that activates that catabolism of angiotensin II, and an agent that prevents the synthesis of angiotensin I.

10. The method of claim 1, wherein the subject is human.

11. The method of claim 10, wherein the subject is hypercholesterolemic, hypertriglyceridemic, hyperlipidemic, a smoker, or hypertensive.

12. The method of claim 1, wherein the subject is free of symptoms calling for treatment for a cardiovascular disorder.

13. A method of selecting a subject for treatment for a cardiovascular disorder and treating the subject, the method comprising:
performing an assay to determine a level of soluble ST2 in a biological sample from a subject having or at risk of developing a cardiovascular disorder;
identifying a subject that has an elevated level of soluble ST2 relative to a control;
selecting the identified subject for treatment for a cardiovascular disorder; and
administering a therapeutically effective amount of a treatment for a cardiovascular disorder to the selected subject.

14. The method of claim 13, wherein the biological sample is blood or serum.

15. The method of claim 13, wherein the assay is performed using an antibody or an antibody fragment that specifically binds to soluble ST2.

16. The method of claim 13, wherein the control is a predetermined value.

17. The method of claim 13, wherein the control is a level of soluble ST2 in a healthy subject.

18. The method of claim 13, wherein the treatment is acute treatment.

19. The method of claim 13, wherein the treatment is prophylactic treatment.

20. The method of claim 13, wherein the treatment comprises an agent selected from the group consisting of: anti-inflammatory agents, anti-thrombotic agents, anti-coagulants, anti-platelet agents, fibrinolytic agents, lipid-reducing agents, direct thrombin inhibitors, glycoprotein IIb/IIIb receptor inhibitors, calcium channel blockers, beta-adrenergic receptor blockers, cyclooxygenase-2 inhibitors, renin-angiotensin- system (RAS) inhibitors, and anti-hypertensive agents.

21. The method of claim 20, wherein the renin-angiotensin system inhibitor is selected from the group consisting of: an angiotensin-converting enzyme (ACE) inhibitor, an angiotensin II receptor blocker (ARB), an agent that activates that catabolism of angiotensin II, and an agent that prevents the synthesis of angiotensin I.

22. The method of claim 13, wherein the subject is human.

23. The method of claim 22, wherein the subject is hypercholesterolemic, hypertriglyceridemic, hyperlipidemic, a smoker, or hypertensive.

24. The method of claim 13, wherein the subject is free of symptoms calling for treatment for a cardiovascular disorder.

25. A method of selecting a subject for participation in a clinical trial for a treatment for a cardiovascular disorder, the method comprising:
performing an assay to determine a level of soluble ST2 in a biological sample from a subject having or at risk of developing a cardiovascular disorder;
identifying a subject that has an elevated level of soluble ST2 relative to a control;
selecting the identified subject for participation in a clinical trial for a treatment for a cardiovascular disorder; and
administering a treatment for a cardiovascular disorder to the selected subject during the clinical trial.

26. The method of claim 25, wherein the biological sample is blood or serum.

27. The method of claim 25, wherein the control is a predetermined value.

28. The method of claim 25, wherein the control is a level of soluble ST2 in a healthy subject.

29. The method of claim 25, wherein the subject has diabetes, hyperinsulinemia, congestive heart failure, angina, abdominal obesity, a family history of coronary artery disease, or a personal history of cerebrovascular disease or occlusive peripheral vascular disease.

30. The method of claim 25, wherein the subject is hypercholesterolemic, hypertriglyceridemic, hyperlipidemic, a smoker, or hypertensive.

31. The method of claim 25, further comprising:
performing an assay to determine a level of cardiac troponin I (cTnI), B type natriuretic peptide (BNP), or C-reactive protein (CRP) in the biological sample;
further identifying a subject with an elevated level of soluble ST2 and an elevated level of cTnI, BNP, or C-reactive protein relative to a control; and
further selecting the identified subject for participation in the clinical study.

32. The method of claim 25, wherein the subject is free of symptoms calling for treatment for a cardiovascular disorder.

33. The method of claim 25, wherein the assay is performed using an antibody or an antibody fragment that specifically binds to soluble ST2.

* * * * *

UNITED STATES PATENT AND TRADEMARK OFFICE
CERTIFICATE OF CORRECTION

PATENT NO.       : 8,597,958 B2
APPLICATION NO.  : 13/150749
DATED            : December 3, 2013
INVENTOR(S)      : Richard T. Lee Page 1 of 1

It is certified that error appears in the above-identified patent and that said Letters Patent is hereby corrected as shown below:

Title Page 2, Col. 2, Line 24 Item 56 (Other Publications), delete "Dyspenea" and insert -- Dyspnea --, therefor.

Title Page 2, Col. 2, Line 43 Item 56 (Other Publications), delete "syspnea" and insert -- dyspnea --, therefor.

Title Page 3, Col. 2, Line 34 Item 56 (Other Publications), delete "Millenium" and insert -- Millennium --, therefor.

Title Page 3, Col. 2, Line 34 Item 56 (Other Publications), delete "Millenium" and insert -- Millennium --, therefor.

In the Claims

Claim 8, Col. 85, Lines 46-47, delete "renin-angiotensin (RAS) system" and insert -- renin-angiotensin system (RAS) --, therefor.

Claim 20, Col. 86, Lines 37-38, delete "renin-angiotensin- system (RAS)" and insert -- renin-angiotensin system (RAS) --, therefor.

Signed and Sealed this
First Day of April, 2014

Michelle K. Lee
*Deputy Director of the United States Patent and Trademark Office*